United States Patent [19]

Sessler et al.

[11] Patent Number: 5,256,399
[45] Date of Patent: Oct. 26, 1993

[54] AROMATIC PENTADENTATE EXPANDED PORPHYRINS IN MAGNETIC RESONANCE IMAGING

[75] Inventors: Jonathan L. Sessler; Gregory W. Hemmi, both of Austin, Tex.; Toshiaki Murai, Gifu, Japan

[73] Assignee: Board of Regents, The University of Texas System, Austin, Tex.

[21] Appl. No.: 880,078

[22] Filed: May 7, 1992

Related U.S. Application Data

[62] Division of Ser. No. 539,975, Jun. 18, 1990, Pat. No. 5,162,509, which is a division of Ser. No. 320,293, Mar. 6, 1989, Pat. No. 4,935,498.

[51] Int. Cl.$^5$ .................. G01N 24/08; A61K 31/555; C07D 487/22
[52] U.S. Cl. ........................ 424/9; 436/173; 436/806; 128/653.4; 534/15; 540/145; 514/185; 514/836
[58] Field of Search .............. 424/9; 436/173, 806; 128/653.4, 654; 534/15; 540/145; 514/836, 185

[56] References Cited

U.S. PATENT DOCUMENTS

| | | | |
|---|---|---|---|
| 4,647,447 | 3/1987 | Gries et al. | 424/9 |
| 4,883,790 | 11/1989 | Levy et al. | 540/145 |
| 4,915,683 | 4/1990 | Sieber | 604/4 |
| 4,935,498 | 6/1990 | Sessler et al. | 534/15 |

FOREIGN PATENT DOCUMENTS

| | | |
|---|---|---|
| 0111418 | 6/1984 | European Pat. Off. |
| 0196515 | 10/1986 | European Pat. Off. |
| 0233701 | 8/1987 | European Pat. Off. |

OTHER PUBLICATIONS

Abid et al., Inorg. Chim. Acta, vol. 95 (1984) 119–125.
Acholla et al., J. Am. Chem. Soc., vol. 107 (1985) 6902–6908.
Acholla et al., Tetrahedron Lett., vol. 25 (1984) 3269–3270.
Ansell, J. Chem. Soc., Chem. Commun. (1982) 546–547.
Bauer et al., J. Am. Chem. Soc., vol. 105, (1983) 6429–6436.
Broadhurst et al., J. Chem. Soc., Chem. Commun. (1970) 807–809.
Broadhurst et al., J. Chem. Soc., Chem. Commun. (1969) 1480–1482.
Broadhurst et al., J. Chem. Soc., Chem. Commun. (1969) 23–24.
Broadhurst et al., J. Chem. Soc. Perkin Trans. 1 (1972) 2111–2116.

(List continued on next page.)

Primary Examiner—Glennon H. Hollrah
Assistant Examiner—Gary E. Hollinden
Attorney, Agent, or Firm—Arnold, White & Durkee

[57] ABSTRACT

The present invention involves a novel tripyrrole dimethine-derived "expanded porphyrin" (texaphyrin), the synthesis of such compounds, their analogs or derivatives and their uses. These expanded porphyrin-like macrocycles are efficient chelators of divalent and trivalent metal ions. Metal complexes of these compounds are active as photosensitizers for the generation of singlet oxygen and thus potentially for inactivation or destruction of human immunodeficiency virus (HIV-1), mononuclear or other cells infected with such virus and tumor cells as well. A variety of texaphyrin derivatives have been produced and many more are readily obtainable. Various metal (e.g., transition, main group, and lanthanide) complexes with the texaphyrin and texaphyrin derivatives of the present invention have unusual water solubility and stability which render them particularly useful. These metallotexaphyrin complexes have optical properties making them unique as compared to existing porphyrin-like or other macrocycles. For example, they absorb light strongly in a physiologically important region (i.e. 690–880 nm). These complexes also form long-lived triplet states in high yield and act as efficient photosensitizers for the formation of singlet oxygen. These properties, coupled with their high chemical stability and appreciable solubility in polar media such as water, add to their usefulness.

6 Claims, 27 Drawing Sheets

OTHER PUBLICATIONS

Cuellar et al., Inorg. Chem., vol. 20 (1981) 3766–3770.
Day et al., J. Am. Chem. Soc., vol. 97 (1975) 4519–4527.
De Cola et al., Inorg. Chem., vol. 25 (1986) 1729–1732.
Dougherty, Photochem. Photobiol., vol. 45 (1987) 879–889.
Gosmann et al., Angew. Chem. Int. Ed. Engl., vol. 25 (1986) 1100–1101.
Gossauer, Bull. Soc. Chim. Belg., vol. 92 (1983) 793–795.
Knubel et al., Angew Chem. Int. Ed. Engl., vol. 27 (1988) 1170–1172.
Lauffer, Chem. Rev., vol. 87 (1987) 901–927.
LeGoff et al., J. Org. Chem. vol. 52 (1987) 710–711.
Marks et al., J. Am. Chem. Soc., vol. 100 (1978) 1695–1705.
Rexhausen et al., J. Chem. Soc., Chem. Commun. (1983) 275.
Sessler et al., J. Org. Chem., vol. 52 (1987) 4394–4397.
Sessler et al., Comm., Inorg. Chem., vol. 7 (1988) 333–350.
Sessler et al., J. Am. Chem. Soc., vol. 110 (1988) 5586–5588.
Tweedle et al. in "Magnetic Resonance Imaging," 2nd ed., Partain, et al., Eds., W. B. Saunders: Philadelphia, vol. I (1988) 793–809.
Vogel et al., Angew. Chem. Int. Ed. Engl., vol. 25 (1986) 257–259.
Sessler et al., Inorg. Chem., vol. 28 (1989) 3390–3393.
Sessler et al., Inorg. Chem., vol. 28 (1989) 1333–1341.
Harriman et al., J. Chem. Soc. Commun., (1989) 314–316.
Sessler et al., J. Coord. Chem., vol 18 (1988) 99–104.
J. Chem. Soc., Chem. Commun., (1989) 314–316 Harriman, A. et al.
Chem. Absts., vol. 111:125716e (Oct. 2, 1989), p. 720 Sessler, A. J. et al.

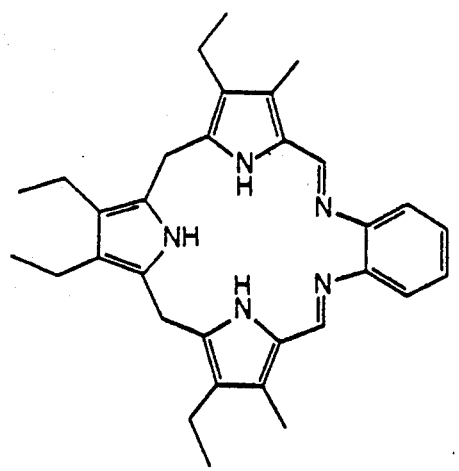
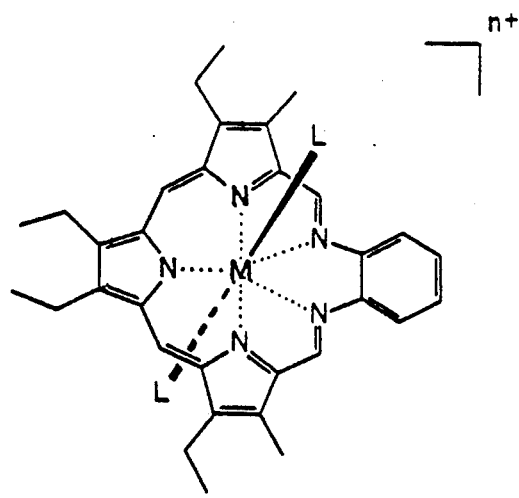
1
2 M=H, n=0
3 M=Cd, n=1
4 M=Cd, n=1, L=pyr
FIG. 1
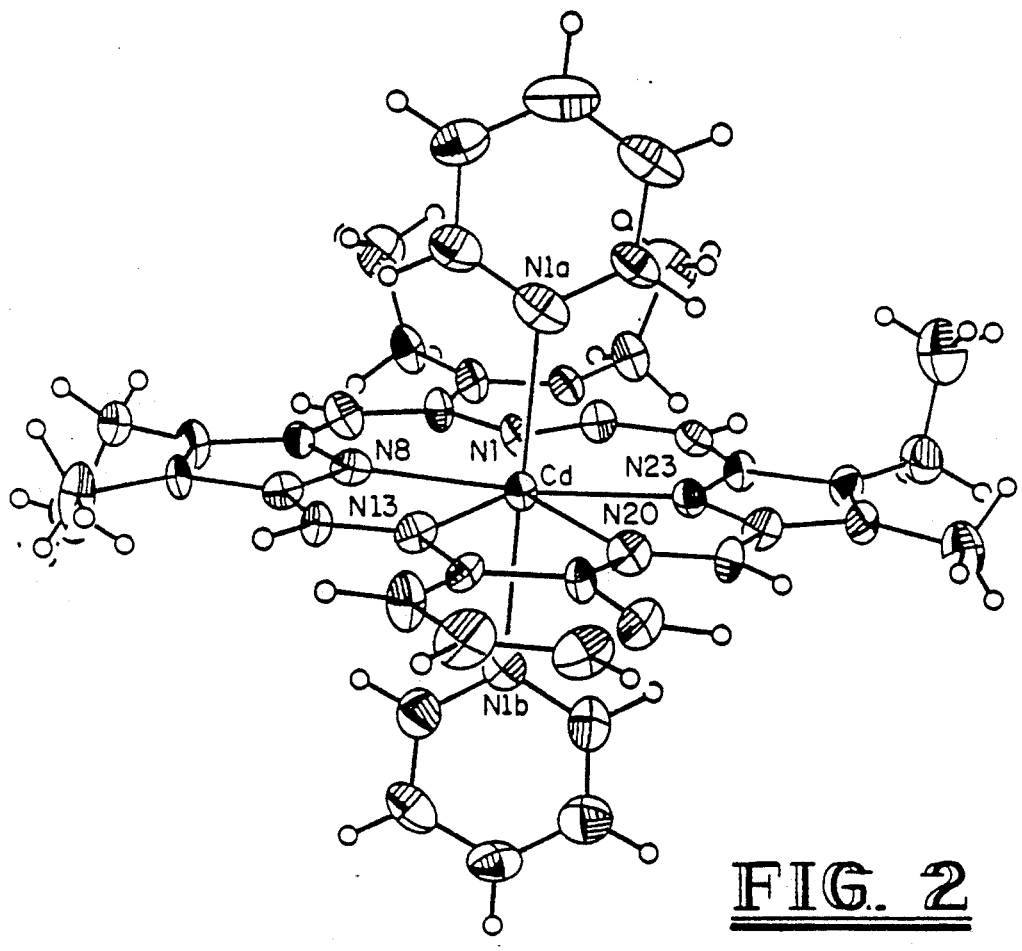
FIG. 2

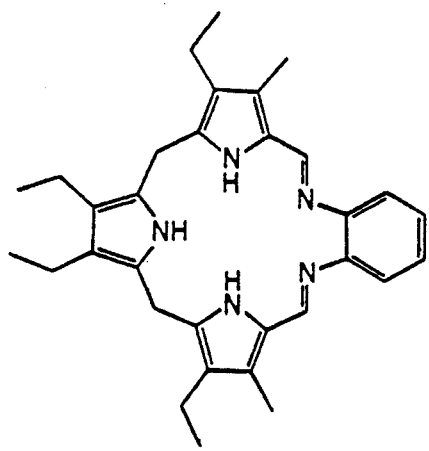
1<sub>A</sub>
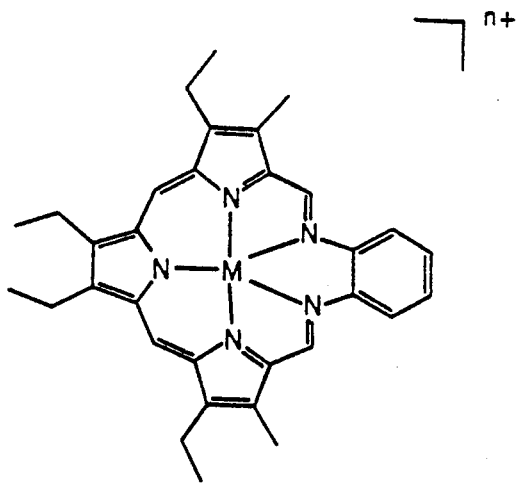
2$_A$. M = H, n = 0
3$_A$. M = Cd, n = 1
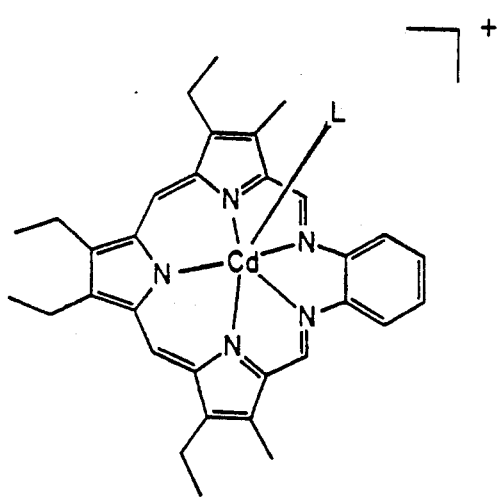
4a$_A$. L = pyr
4b$_A$. L = Bzlm
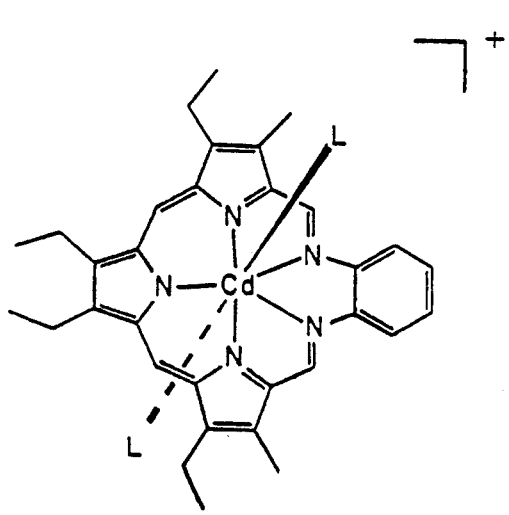
5a$_A$. L = pyr
5b$_A$. L = Bzlm
FIG. 4

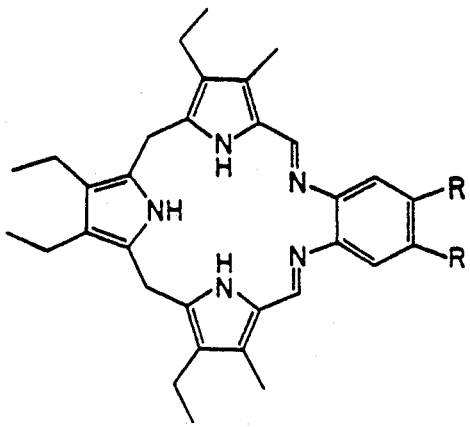
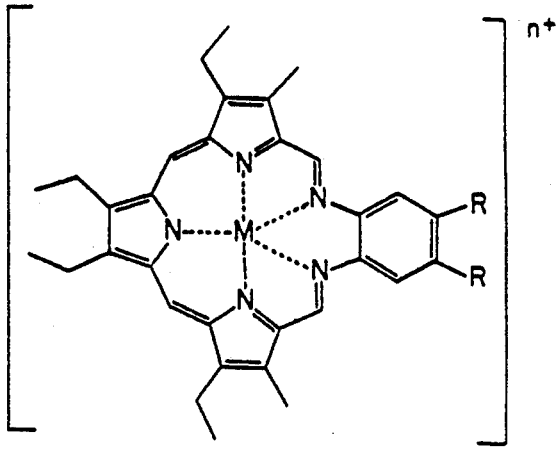
10B R = H
11B R = CH₃
| | | | |
|---|---|---|---|
| 1B | M = H, | R = H, | n = 0 |
| 2B | M = Cd, | R = H, | n = 1 |
| 3B | M = Nd, | R = H, | n = 2 |
| 4B | M = Sm, | R = H, | n = 2 |
| 5B | M = Eu, | R = H, | n = 2 |
| 6B | M = H, | R = CH₃, | n = 2 |
| 7B | M = Gd, | R = CH₃, | n = 2 |
| 8B | M = Eu, | R = CH₃, | n = 2 |
| 9B | M = Sm, | R = CH₃, | n = 2 |
FIG. 17
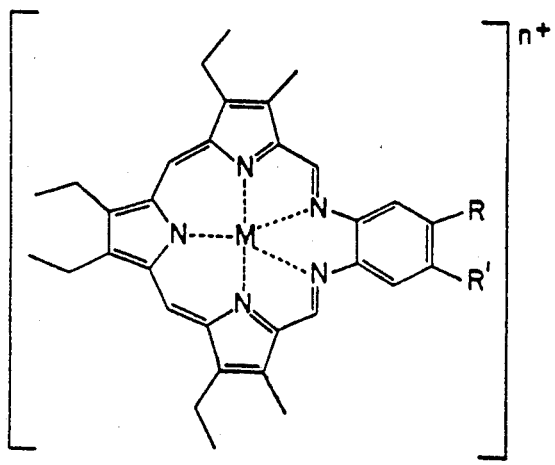
| | | | |
|---|---|---|---|
| 1 | M = Zn, | R = R' = H, | n = 1 |
| 2 | M = Zn, | R = H, R' = Cl, | n = 1 |
| 3 | M = Cd, | R = R' = H, | n = 1 |
| 4 | M = Cd, | R = H, R' = Cl, | n = 1 |
| 5C | M = Mn, | R = R' = H, | n = 1 |
| 6C | M = Sm, | R = R = CH₃, | n = 2 |
| 7C | M = Eu, | R = R' = CH₃, | n = 2 |
| 8C | M = In, | R = R' = H, | n = 2 |
| 9C | M = In, | R = R' = CH₃, | n = 2 |
| 10C | M = Y, | R = R' = H, | n = 2 |
| 11C | M = Y, | R = R' = CH₃, | n = 2 |
FIG. 19

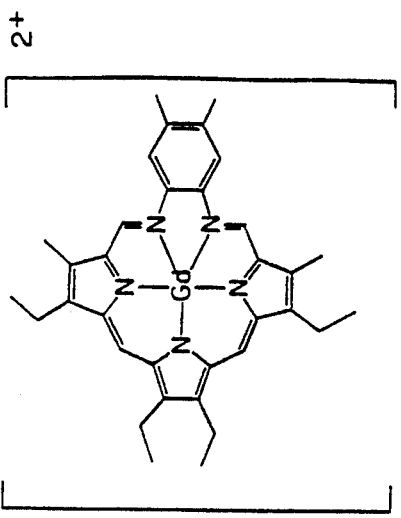
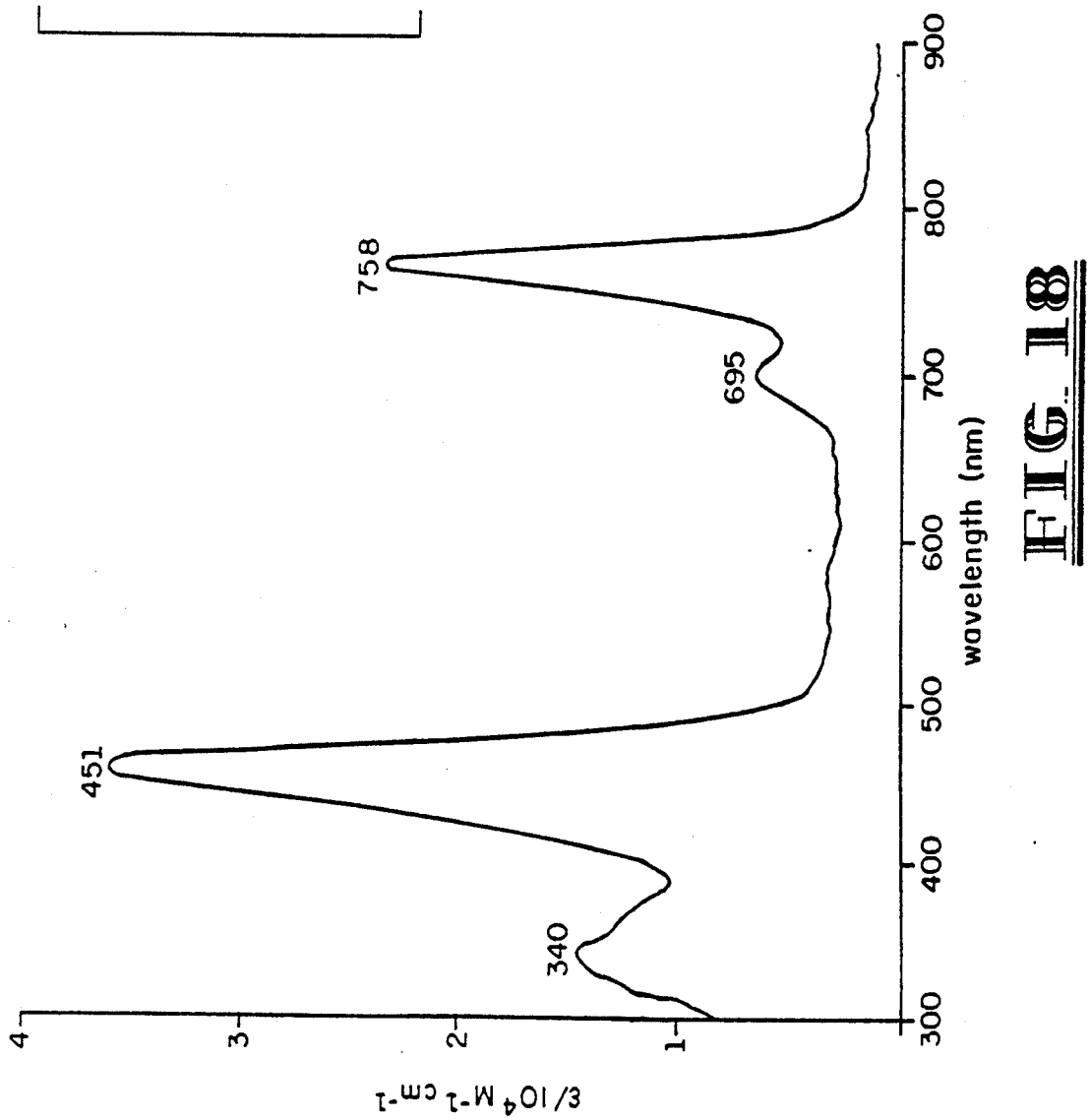
FIG. 18A
FIG. 18

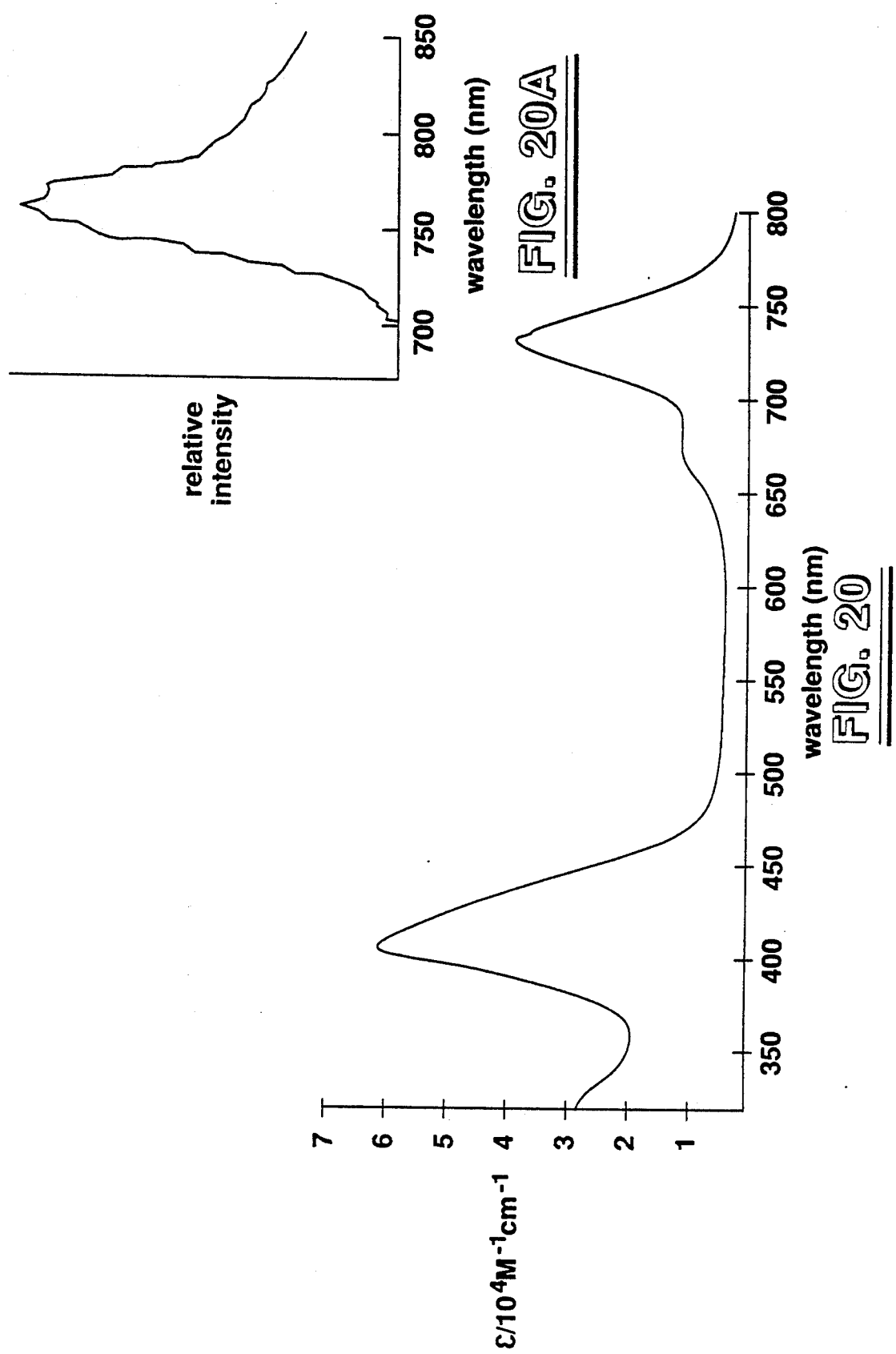

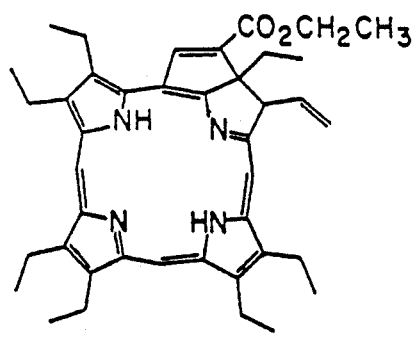 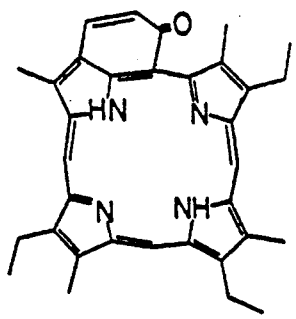
1_D
2_D
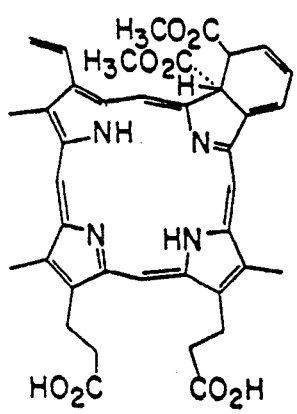 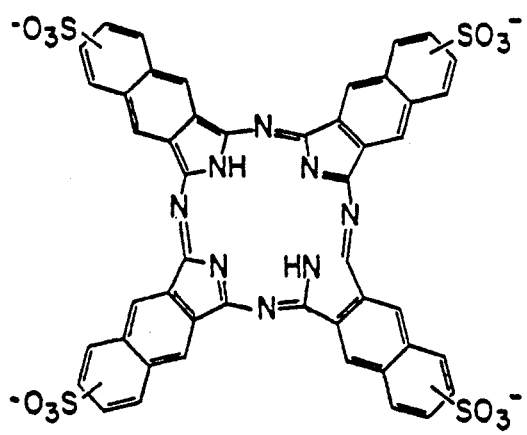
3_D
4_D
FIG. 23

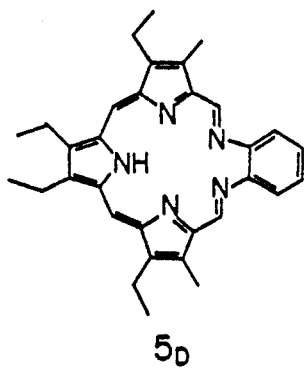
5D
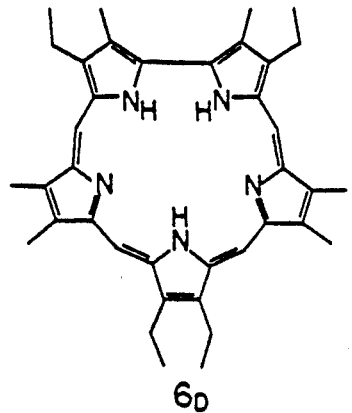
6D
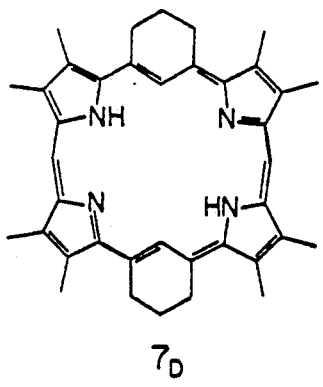
7D
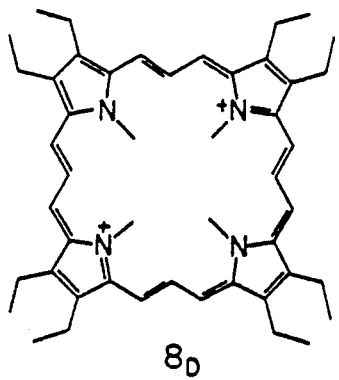
8D
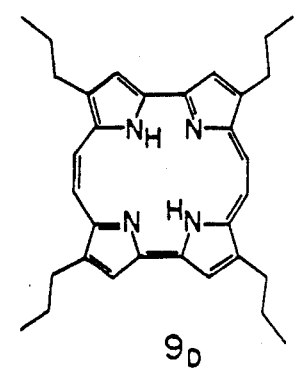
9D
FIG. 24

10D R=R'=CH₃
11D R=H,R'=OCH₃
12D R=H,R'=Cl
13D R=H,R'=NO₂
14D R=H,R'=CO₂H

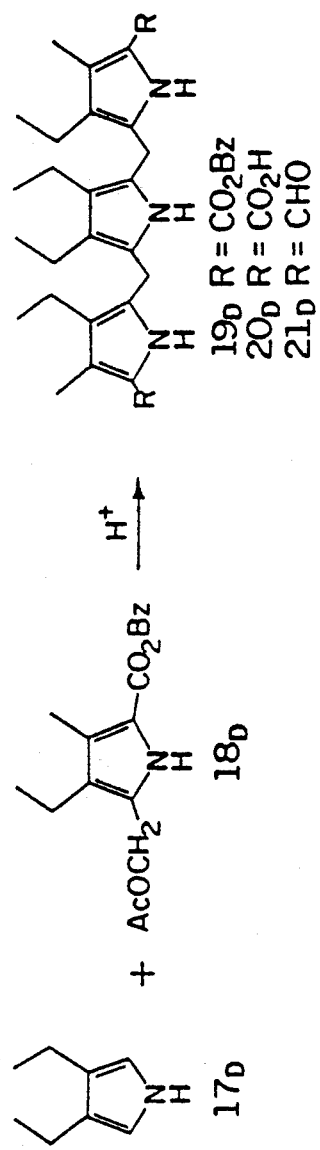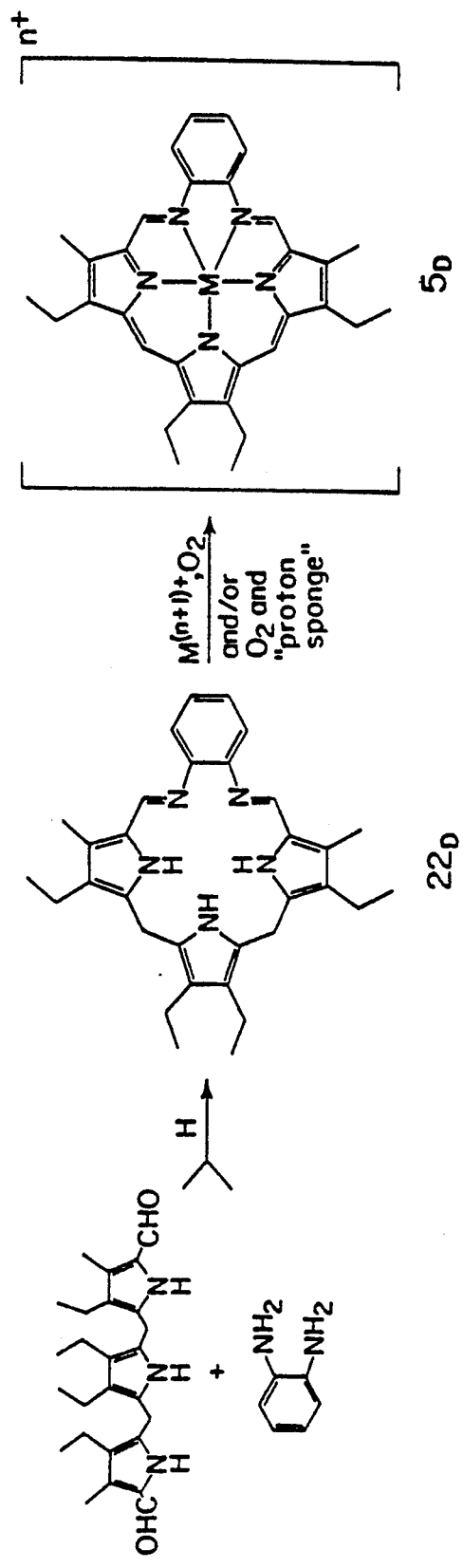
FIG. 26

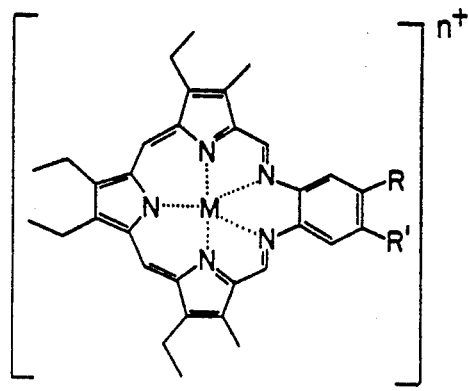
23D  R = R' = F
24D  R = H  R' = O(CH₂CH₂O)₂CH₃
25D  R = H  R' = SO₃⁻
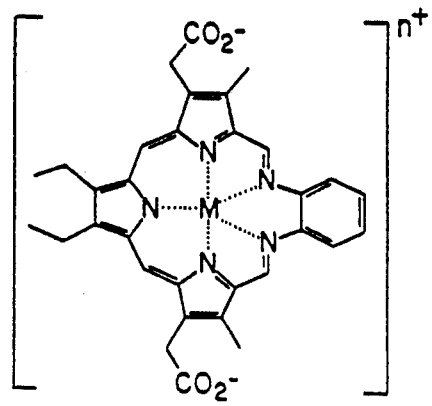
26D
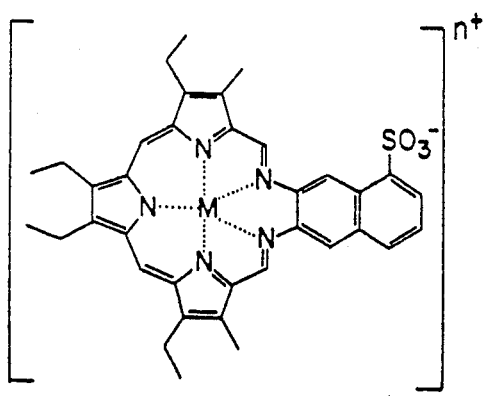
27D
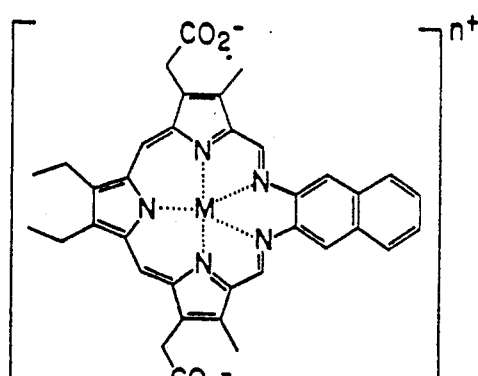
28D
FIG. 27

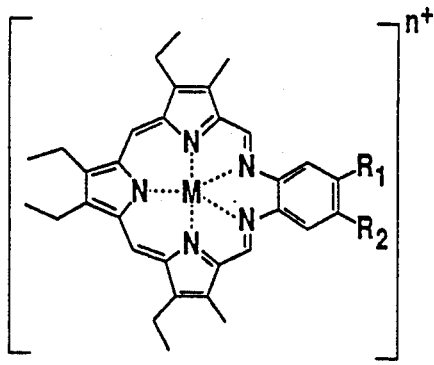

1E $R_1 = R_2 = H$*
2E $R_1 = R_2 = CH_3$*
3E $R_1 = H, R_2 =$ **
4E $R_1 = H, R_2 = B$ **
5E $R_1 = H, R_2 = NO_2$**
6E $R_1 = H, R_2 = OCH_3$**
7E $R_1 = H, R_2 = CO_2H$

\* all listed metals
\*\* Zn or Cd $M = H$ and $n = 0$
$M = Hg^{+2}, Cd^{+2}, Zn^{+2}, Co^{+2}, Sn^{+2}$, or $Mn^{+2}$ and $n = 1$
$M = Ln^{+3}, Gd^{+3}, Y^{+3}$, or $In^{+3}$ and $n = 2$

FIG. 31B

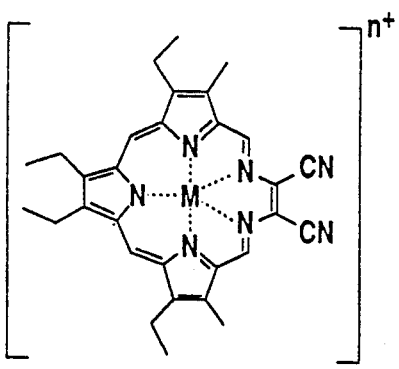

8E $M = Hg^{+2}, Cd^{+2}, Zn^{+2}, Co^{+2}, Sn^{+2}$, or $Mn^{+2}$ and $n = 1$
$M = Ln^{+3}, Gd^{+3}, Y^{+3}$, or $In^{+3}$ and $n = 2$

FIG. 31A

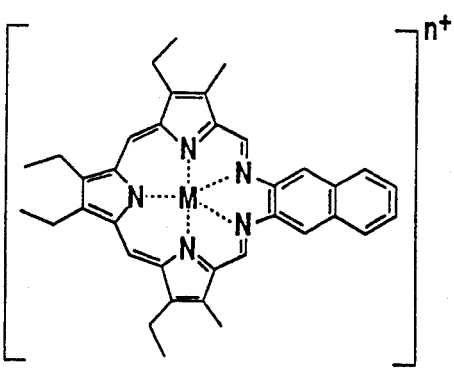

9E $M = Hg^{+2}, Cd^{+2}, Zn^{+2}, Co^{+2}, Sn^{+2}$, or $Mn^{+2}$ and $n = 1$
$M = Ln^{+3}, Gd^{+3}, Y^{+3}$, or $In^{+3}$ and $n = 2$

FIG. 31

AROMATIC PENTADENTATE EXPANDED PORPHYRINS IN MAGNETIC RESONANCE IMAGING

This invention was made in part with government support under the National Science Foundation Presidential Young Investigator Award (1986) to J. L. Sessler, grant CHE-8552768. The government has certain rights in the invention.

This is a division of copending application Ser. No. 539,975, filed Jun. 18, 1990 issued as U.S. Pat. No. 5,162,509 which is a division of Ser. No. 320,293 filed Mar. 6, 1989 and issued as U.S. Pat. No. 4,935,498 on Jun. 19, 1990. The copending application and the patent are incorporated by reference herein.

BACKGROUND OF THE INVENTION

The porphyrins and related tetrapyrrole macrocycles are among the most versatile of tetradentate ligands[1] (see Example 1 for the references in this paragraph). Attempts to stabilize higher coordination geometries, however, with larger porphyrin-like aromatic macrocycles have met with little success.[2-5] Indeed, to date, only the uranyl complex of "superphthalocyanine" has been isolated and characterized structurally,[2] although several other large porphyrin-like aromatic macrocycles, including the "sapphyrins",[3,6] "oxosapphyrins",[6,7] "platyrins",[8] "pentaphyrin",[9] and "[26]porphyrin",[10] have been prepared in their metal free forms.

Although the porphyrins and related tetrapyrrolic compounds remain among the most widely studied of all known macrocycles,[1] relatively little effort has been devoted to the development of larger conjugated pyrrole containing systems[2-12] (references cited in this paragraph are shown in Example 2). Large, or "expanded" porphyrin-like systems, however, are of interest for several reasons: They could serve as possible aromatic analogues of the better studied porphyrins[2-8] or serve as potential biomimetic models for these or other naturally occurring pyrrole-containing systems.[13,14] In addition, large pyrrole containing systems offer exciting possibilities as novel metal binding macrocycles.[2,9-12,15] For instance, suitably designed systems could act as versatile ligands capable of binding larger metal cations and/or stabilizing higher coordination geometries[2,16] than those routinely accommodated within the normally tetradentate ca. 2.0 Å radius porphyrin core.[17] The resulting complexes could have important application in the area of heavy metal chelation therapy, serve as contrast agents for magnetic resonanace imaging (MRI) applications, act as vehicles for radioimmunological labeling work, or serve as new systems for extending the range and scope of coordination chemistry.[15,18] In addition, the free-base (metal-free) and/or diamagnetic metal-containing materials could serve as useful photosensitizers for photodynamic therapeutic applications. In recent years a number of potentially pentadentate polypyrrolic aromatic systems, including the "sapphyrins",[3,4] "oxosapphyrins",[5] "smaragdyrins",[3,4] platyrins,[6] and "pentaphyrin"[7] have been prepared and studied as their metal-free forms. For the most part, however, little or no information is available for the corresponding metallated forms. Indeed, the uranyl complex of "superphthalocyanine" was the only metal-containing pentapyrrolic system which has been prepared and characterized structurally.[2] Unfortunately, the "superphthalocyanine" system is apparently not capable of existence in either its free-base or other metal-containing forms.[2] Thus, prior to the present invention, no versatile, structurally characterized, pentadentate aromatic ligands were available,[11] although a number of nonaromatic pyridine-derived pentadentate systems had previously been reported.[19,20]

Gadolinium(III) complexes derived from strongly binding anionic ligands, such as diethylenetriamine pentaacetic acid (DTPA),[1,2,3] 1,4,7,10-tetraazacyclododecane N,N',N'',N'''-tetraacetic acid (DOTA),[1,4,5] and 1,10-diaza-4,7,13,16-tetraoxacyclooctadecane-N,N'-diacetic acid (dacda),[1,6] are among the most promising of the paramagnetic contrast currently being developed for use in magnetic resonance imaging (MRI)[1] (references cited in this paragraph are shown in Example 3). Indeed, [Gd.DTPA]⁻ is now undergoing clinical trials in the United States for possible use in enhanced tumor detection protocols.[1] Nonetheless, the synthesis of other gadolinium(III) complexes remains of interest since such systems might have greater kinetic stability, superior relaxivity, or better biodistribution properties than the existing carboxylate-based contrast agents. One approach currently being pursued is based on using water-soluble porphyrin derivatives, such as tetrakis(4-sulfonatophenyl)porphyrin (TPPS).[7,8,9] Unfortunately, the large gadolinium(III) cation cannot be accommodated completely[10] within the relatively small prophyrin binding core ($r_\infty 2.0$ Å[11]), and, as a consequence, gadolinium prophyrin complexes are invariably hydrolytically unstable.[7,8,12,13] Larger porphyrin-like ligands, however, might offer a means of circumventing this problem.[14-22]

Acquired immunodeficiency syndrome (AIDS) and cancer are among the most serious public health problems facing our nation today. AIDS, first reported in 1981 as occurring among male homosexuals,[1] is a fatal human disease which has now reached pandemic proportions (the references in this and the following four paragraphs are shown in Example 5). Cancer, in spite of some very significant advances in diagnostics and treatment in recent years, remains the third leading cause of death in this country. Finding better ways to detect, treat, and reduce the transmission of these disorders are thus research objectives of the highest importance.

One of the more promising new modalities currently being explored for use in the control and treatment of tumors is photodynamic therapy (PDT).[1-5] This technique is based on the use of a photosensitizing dye, which localizes at, or near, the tumor site, and when irradiated in the presence of oxygen serves to produce cytotoxic materials, such as singlet oxygen ($O_2(^1\Delta_g)$), from otherwise benign precursors (e.g. $O_2(^3\Sigma_g-)$). Much of the current excitement associated with PDT derives from just this property: In marked contrast to current methods (e.g. conventional chemotherapy), in pDT the drugs themselves can (and should) be completely innocuous until "activated" with light by an attending physician. Thus a level of control and selectivity may be attained which is not otherwise possible.

At present, diamagnetic porphyrins and their derivatives are considered the dyes of choice for PDT. It has been known for decades that porphyrins, such as hematoporphyrin, localize selectively in rapidly growing tissues including sarcomas and carcinomas,[6] although the reasons for this selectivity remain recondite. Currently most attention is focusing on the so-called hematoporphyrin derivative (HPD),[2-5,7-21] an incompletely characterized mixture of monomeric and oligomeric porphyrins produced by treating hematoporphyrin dihydrochloride with acetic acid-sulfuric acid followed by dilute base.[22-27] Fractions rich in the oligomeric species, which are believed to have the best tumor-localizing ability,[23,26] are marketed under the trade name Photofirin II ® (PII) and are currently undergoing phase III clinical trials for obstructed endobronchial tumors and superficial bladder tumors. Here, the mechanism of action is thought to be largely, if not entirely, due to the photoproduction of singlet oxygen ($O_2(^1\Delta_g)$), although alternative mechanisms of action, including those involving superoxide anion or hydroxyl and/or porphyrin-based radicals cannot be entirely ruled out.[28-33] Promising as HPD is, it and other available photosensitizers (e.g., the phthalocyanines and napthapthalocynines) suffer from serious disadvantages.

While porphyrin derivatives have high triplet yields and long triplet lifetimes (and consequently transfer excitation energy efficiently to triplet oxygen),[3b,3g] their absorption in the Q-band region often parallels that of heme-containing tissues. phthalocyanines and naphthalocyanines absorb in a more convenient spectral range but have significantly lower triplet yields;[4] moreover, they tend to be quite insoluble in polar protic solvents, and are difficult to functionalize. Thus at present the development of more effective photochemotherapeutic agents appears to require the synthesis of compounds which absorb in the spectral region where living tissues are relatively transparent (i.e., 700-1000 nm),[1d] have high triplet quantum yields, and are minimally toxic. The present inventors have recently reported[5] (see Example 1) the synthesis of a new class of aromatic porphyrin-like macrocycles, the tripyrroledimethine-derived "texaphyrins", which absorb strongly in the tissue-transparent 730-770 nm range. The photophysical properties of metallotexaphyrins $2_C$-$7_C$ parallel those of the corresponding metallaporphyrins and the diamagnetic complexes $1_C$-$4_C$ sensitize the production of $^1O_2$ in high quantum yield. FIG. 19 shows the schematic structure, metal complexes and derivatives of compounds of the present invention ($1_C$-$7_C$).

Singlet oxygen is also believed to be the critical toxic species operative in experimental photsensitized blood purification procedures.[34-39] This very new application of photodynamic therapy is of tremendous potential importance: It shows promise of providing a safe and effective means of removing enveloped viruses such as HIV-1, herpes simplex (HSV), cytomegalovirus (CMV), various forms of hepatitis-inducing virus, as well as other opportunistic blood-borne infections (e.g. bacteria and malaria plasmodium) from transfused whole blood. Given that AIDS is currently a not effectively treated and usually fatal disease, the benefit of such a blood purification procedure would be of inestimable value.

At present, sexual relations and needle-sharing are the dominant mechanisms for the spread of AIDS.[1] An increasing percentage of AIDS infections, however, are now occurring as a result of blood transfusions.[1,40-43] Unfortunately, banked blood components are essential products for the practice of modern medicine and as a result this method of transmission is not likely to be precluded by simple changes in lifestyle. Rather, an absolutely fail-proof means must be developed to insure that all stored blood samples are free of the AIDS virus (and ideally all other blood-borne pathogens). To a certain extent this can be accomplished by screening the donors' histories and carrying out serologic tests. At present, however, the serologic tests for HIV-1 are insufficient to detect all infected blood samples, in particular, those derived from donors who have contacted the disease but not yet produced detectable antibodies.[42,43] In addition, new mutants of the AIDS virus have been detected; some or all of which may escape detection by current means.[1] Thus, an antiviral system is needed which removes any form of HIV-1 from stored blood. This is particularly important since a stored blood sample from one infected donor could potentially end up being administered to several different patients, in, for instance, the course of pediatric care.

SUMMARY OF THE INVENTION

The present invention involves a novel tripyrrole dimethine-derived "expanded porphyrin" (texaphyrin), the synthesis of such compounds, their analogs or derivatives and their uses. These expanded porphyrin-like macrocycles are efficient chelators of divalent and trivalent metal ions. Metal complexes of these compounds are effective as photosensitizers for the generation of singlet oxygen and thus potentially useful for the inactivation or destruction of tumors as well as for the prophylactic treatment and removal of human immunodeficiency virus (HIV-1), and other viral contaminants from blood. A variety of texaphyrin derivatives have been produced and many more are readily obtainable. Various metal (e.g., lanthanide) complexes with the texaphyrin and texaphyrin derivatives of the present invention have unusual water solubility and stability which render them particularly useful. These metallotexaphyrin complexes have optical properties making them unique as compared to existing porphyrin-like or other macrocycles. For example, they absorb light strongly in a physiologically important region (i.e. 690-880 nm). Certain diamagnetic complexes also form long-lived triplet states in high yield and act as efficient photosensitizers for the formation of singlet oxygen. These properties, coupled with their high chemical stability and appreciable solubility in polar media such as water, add to their usefulness.

The present invention relates to a class of compounds related to the basic compound having the structure:

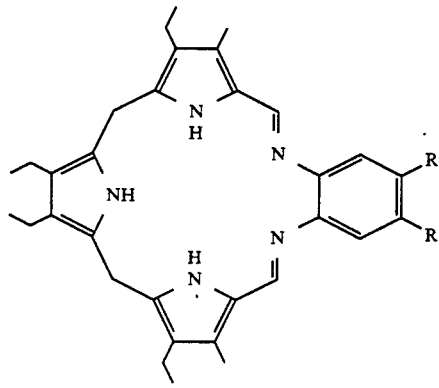

wherein R is H or $CH_3$. This compound has been prepared as one having the structure:

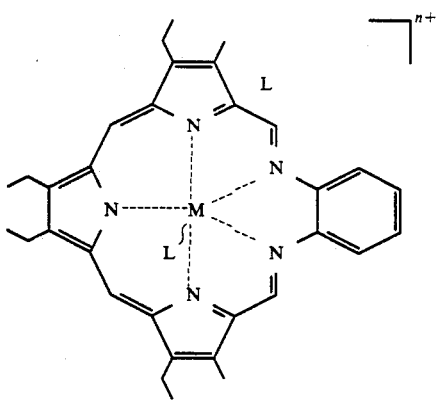

wherein M is H, L is absent and n is 0; or M is Cd, L is pyridine or benzimidazole and n is 1.

A preferred compound of this invention is a cadmiumtexaphyrin complex having the structure:

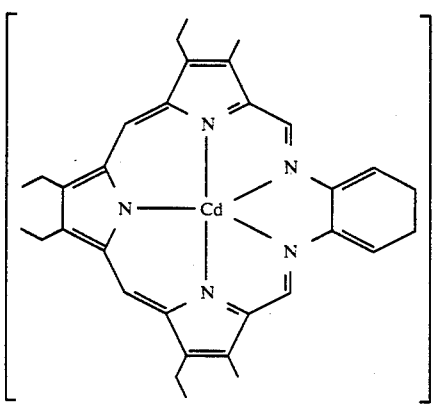

A variety of texaphyrin derivatives and their metal complexes have been prepared and may be characterized as having the structure:

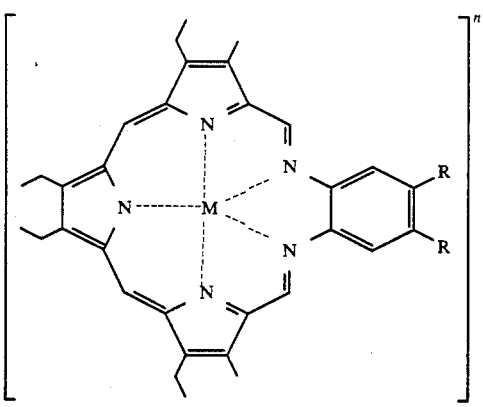

wherein M is H, R is H and n is 0;
M is $Cd^{+2}$, R is H and n is 1;
M is $Nd^{+3}$, R is H and n is 2;
M is $Sm^{+3}$, R is H and n is 2;
M is $Eu^{+3}$, R is H and n is 2;
M is $Gd^{+3}$, R is H, and n is 2;
M is $Y^{+3}$, R is H, and n is 2;

M is $In^{+3}$, R is H, and n is 2;
M is $Zn^{+2}$, R is H and n is 1;
M is $Hg^{+2}$, R is H, and n is 1.
M is H, R is $CH_3$ and n is O;
M is $Gd^{+3}$, R is $CH_3$ and n is 2;
M is $Eu^{+3}$, R is $CH_3$ and n is 2;
M is $Sm^{+3}$, R is $CH_3$ and n is 2;
M is $Y^{+3}$, R is $CH_3$ and n is 2; or
M is $In^{+3}$, R is $CH_3$ and n is 2.

The present invention also includes a compound which may be described as having the structure:

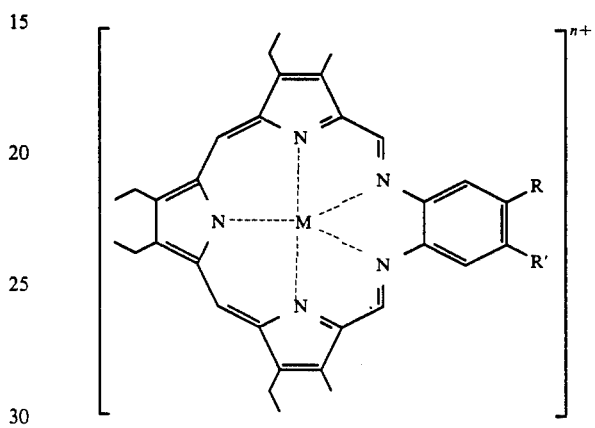

wherein M is $Zn^{+2}$, R and R' are H and n is 1;
M is Zn, R is H, R' is Cl and n is 1;
M is Cd, R and R' are H and n is 1;
M is Cd, R is H, R' is Cl and n is 1;
M is Mn, R and R' are H, and n is 1;
M is Sm, R and R' are $CH_3$ and n is 2;
M is Eu, R and R' are $CH_3$ and n is 2; or
M is Gd, R and R' are $CH_3$ and n is 2.

In a broader view, the present invention involves a compound having the structure:

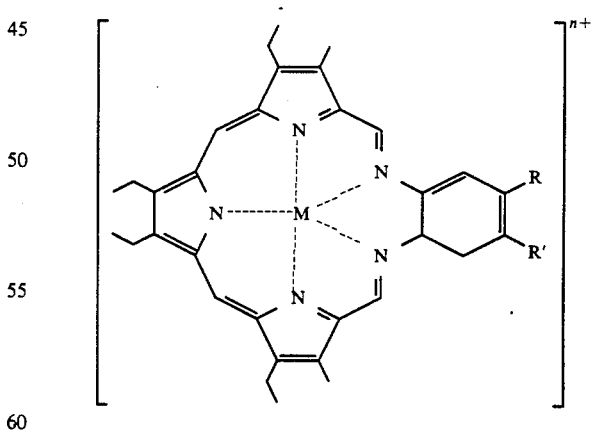

wherein R and R' are $CH_3$; R is H and R' is $OCH_3$; R is H and R' is Cl; R is H and R is COOH or R is H and R' is $NO_2$; and wherein M is a divalent metal ion and n is 1, or M is a trivalent metal ion and n is 2.

In another view the texaphyrin and its derivatives and complexes thereof of the present invention have the structure:

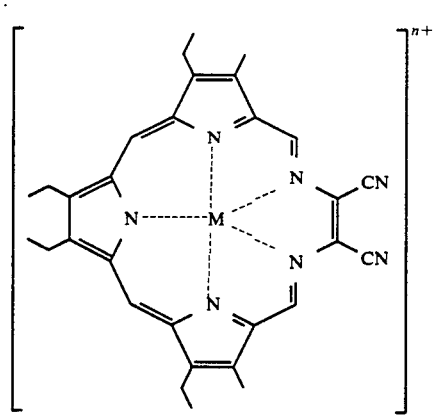

wherein M is a divalent metal ion and n is 1, or M is a trivalent metal ion and n is 2.

A particularly interesting texaphyrin analog of the present invention is one having the structure:

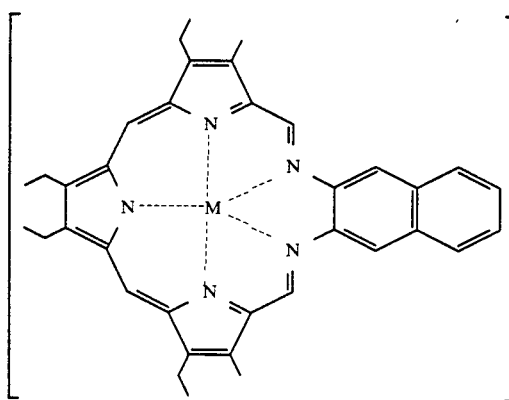

wherein M is a divalent metal ion and n is 1, or M is a trivalent metal ion and n is 2. In the above-described metallic complexes M may be a divalent metal ion selected from the group consisting of $Ca^{+2}$, $Mn^{+2}$, $Co^{+2}$, $Ni^{+2}$, $Zn^{+2}$, $Cd^{+2}$, $Hg^{+2}$, $Sm^{+2}$ and $UO_2^{+2}$, (and n is 1) In certain aspects M is preferably $Cd^{+2}$ or $Zn^{+2}$ or $Hg^{+2}$. When M is a trivalent metal ion, it is preferably selected from the group consisting of $Mn^{+3}$, $Co^{+3}$, $Mn^{+3}$, $Ni^{+3}$, $Y^{+3}$, $In^{+3}$, $Pr^{+3}$, $Nd^{+3}$, $Sm^{+3}$, $Eu^{+3}$, $Gd^{+3}$, $Tb^{+3}$, $Dy^{+3}$, $Er^{+3}$, $Tm^{+3}$, $Yb^{+3}$, $Lu^{+3}$, and $U^{+3}$; (and n is 2.) Most preferred trivalent metal ions are $In^{+3}$, $Y^{+3}$, $Nd^{+3}$, $Eu^{+3}$, $Sn^{+3}$ and $Gd^{+3}$.

Additionally, the compounds of the present invention may be described as having the structure:

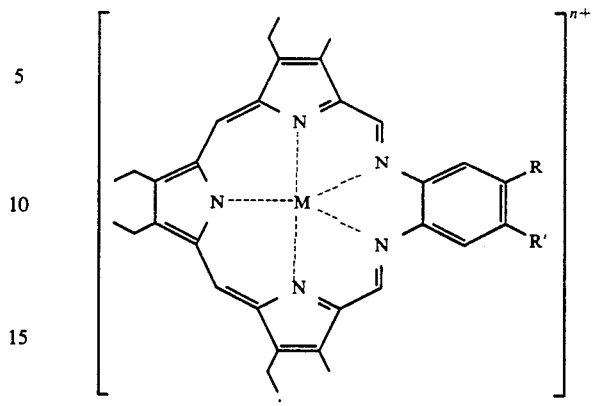

wherein R and R' are F; R is H and R' is $O(CH_2CH_2O)_2CH_3$; R is H and R' is $SO_3^-$; or R is H and R' is $CO_2^-$ and M is a divalent metal ion and n is 1 or M is trivalent metal ion and n is 2.

A particularly preferred texaphyrin-derived compound is one having the structure:

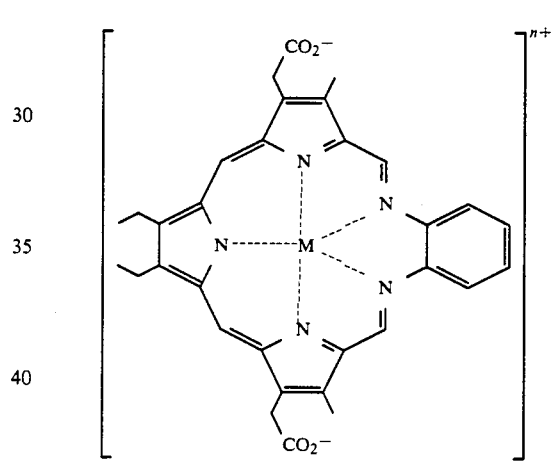

wherein M is a divalent metal ion and n is 1 or M is a trivalent metal ion and n is 2.

In another aspect, the present invention involves a compound having the structure:

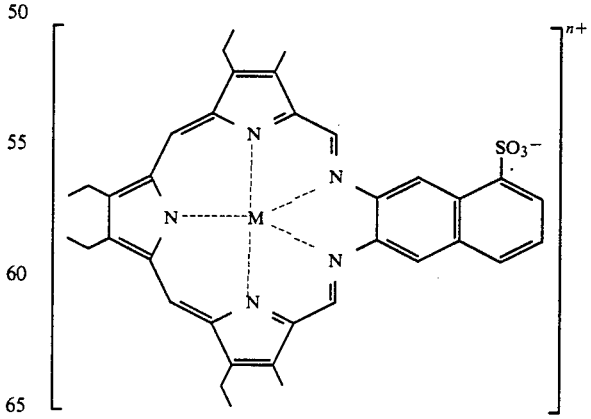

wherein M is a divalent metal ion and n is 1; or M is a trivalent metal ion and n is 2 is exemplary of the texaphyrin derivatives of the present invention. So also is a compound having the structure:

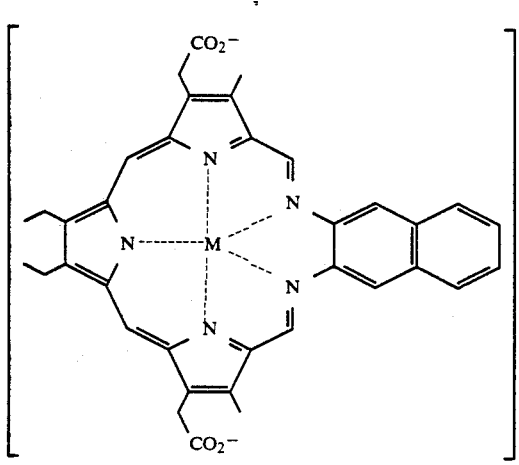

wherein M is a divalent metal ion and n is 1 or M is a trivalent metal ion and n is 2.

In yet another view, the present invention includes a compound having the structure:

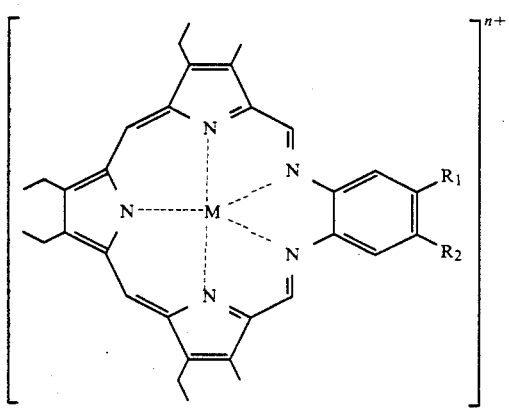

wherein $R_1$ and $R_2$ and H or $CH_3$ and M is $Hg^{+2}$, $Cd^{+2}$, $Co^{+2}$ or $Mn^{+2}$, and n is 1; or M is $Ln^{+3}$, $Gd^{+3}$, $Y^{+3}$ or $In^{+3}$ and n is 2; or $R_1$ is H, $R_2$ is Cl, Br, $NO_2$, $CO_2H$ or $OCH_3$, M is $Zn^{+2}$, $Hg^{+2}$, $Sn^{+2}$ or $Cd^{+2}$ and n is 1.

Absent metal ions, compounds of the present invention may have the structure:

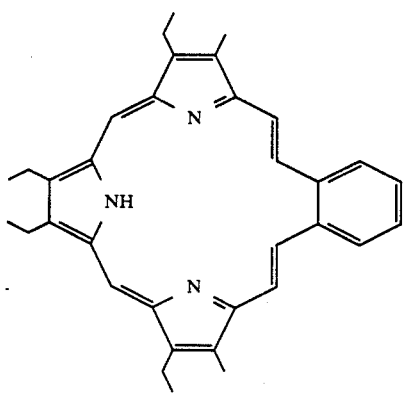

or the structure:

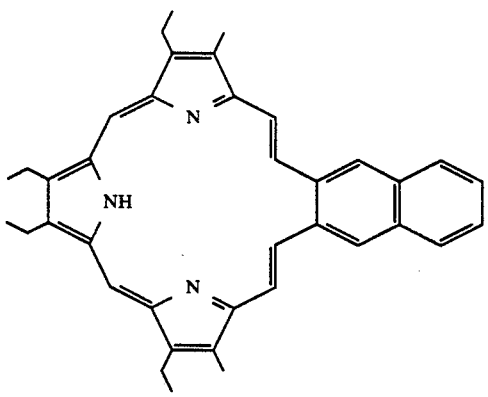

For example, a method for the synthesis of pentadentate expanded porphyrin compound is an aspect of the present invention. This method comprises synthesizing a diformyl tripyrrane; condensing said tripyrrane with an ortho aryldiamine 1,2-diaminoalkene or 1,2-diaminoalkane; and oxidizing the condensation product to form a pentadentate expanded porphyrin compound. A preferred 1,2-diaminoalkene is diamisomaleonitrile. The ortho aryldiamine is preferably ortho phenylenediamine or a substituted ortho phenylenediamine. Another preferred ortho aryldiamine is 2,3-diaminonapthalene. Such a pentadentate expanded porphyrin compound is complexed with a metal and wherein a metal complex is produced by reaction of the pentadentate expanded porphyrin compound with metal ions.

The present invention also involves a method of deactivating retroviruses and enveloped viruses in blood. This method comprises adding a pentadentate expanded porphyrin analog metal complex as described above to blood and exposing the mixture to light to facilitate the formation of singlet oxygen.

Photodynamic tumor therapy comprising administering a pentadentate expanded porphyrin analog complexed with a metal to a tumor host and irradiating the analog in proximity to the tumor is another aspect of the present invention.

A method for MRI enhancement comprising administering a diamagnetic metal ion (such as gadolinium, for example) complexed with texaphyrin or a texaphyrin derivative is also an aspect of the present invention.

BRIEF DESCRIPTION OF THE DRAWINGS

FIG. 1 shows a schematic structural view of Texaphyrin (1) and various complexes (2, 3 and 4).

FIG. 2 shows a view of complex 4 (from FIG. 1) showing pyridine and macrocycle coordination to Cd. Ellipsoids scaled to the 40% probability level. The Cd ion lies in the plane of the nearly planar macrocycle (maximum deviation from planarity 0.10 (1) Å). Relevant Cd-N bond lengths (Å) are as follows: 2.418(7), N1; 2.268(8), N8; 2.505(7), N13; 2.521(7), N20; 2.248(8), N23; 2.438(14), N1a: 2.473(12), N1b. Selected N-Cd-N bond angles (deg) are as follows: N1-Cd-N8, 78.9(2); N1-Cd-N23, 80.2(3); N8-Cd-N13, 68.4(2); N13-Cd-N20, 64.4(2); N20-Cd-N23, 68.2(3); N1a-Cd-N1b, 176.1(4).

FIG. 4 shows a schematic representation of the reduced ($1_A$) and oxidized ($2_A$) forms of the free-base "texaphyrin" and representative five, six, and seven coordinate cadmium complexes ($3_A$-$5_A$) derived from this "expanded porphyrin".

FIG. 17 shows metal complexes and derivatives ($1_B$-$11_B$) of compounds of the present invention.

FIG. 18 shows the electronic spectrum of $2_B.(OH)_2$ in $CHCl_3$.

FIG. 19 schematically shows the structure, metal complexes and derivatives of compounds of the present invention ($1_C$-$11_C$).

FIG. 20 shows the absorption spectrum of complex $1_C.Cl$ in deoxygenated methanol. The inset shows the fluorescence emission spectrum recorded in this same solvent.

FIG. 23 shows schematic structures of previously developed prophyrin derivatives potentially useful as photosensitizers. These include purpurins ($1_D$): verdins ($2_D$); benz-fused porphyrins ($3_D$); and sulfonated phthalocyanines and napthylocyanines ($4_D$).

FIG. 24 shows schematic structures of texaphyrin ($5_D$); sapphyrin ($6_D$); platyrin ($7_D$); vinylogous porphyrin ($8_D$); and porphycenes ($9_D$).

FIG. 26 schematically (scheme 1) summarizes the synthesis of texaphyrin ($5_D$).

FIG. 27 shows schematic structures of proposed texaphyrin derivatives ($23_D$-$28_D$).

FIG. 31 shows expanded porphyrin-like macrocycles on hand. Alternatively to the pyrrolic hydrogen, a dior trivalent cation such as $Cd^{2+}$, $Zn^{2+}$, $In^{3+}$, etc. may be bound. In this case, the complex could bear a net overall charge, i.e. +1 for $M^{+2}$ and +2 for $M^{+3}$.

DESCRIPTION OF THE PREFERRED EMBODIMENT

Figure 3:
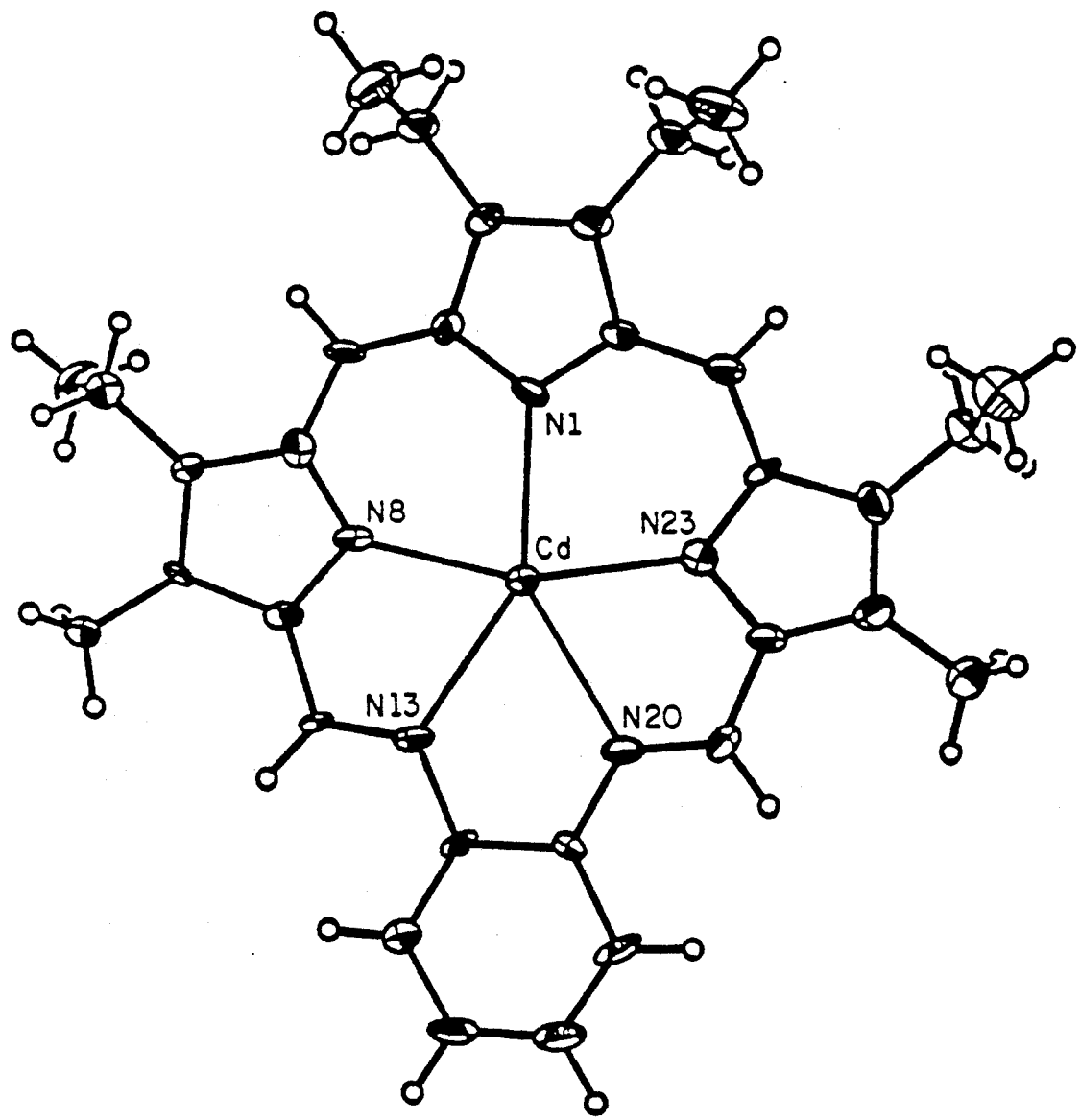
FIG. 3 shows a view of complex 4 perpendicular to the plane through the macrocycle. Pyridine rings (not shown) lie perpendicular to the macrocycle with dihedral angles of 88.5 (4)° for ring a and 89.1 (3)° for ring b.

The present invention involves the synthesis of a novel "expanded porphyrin" system, 1B (to which the trivial name "texaphyrin" has been assigned), and includes description of the structure of the bispyridine adduct of its cadmium(II) complex. The presence in this structure of a near circular pentadentate binding core which is roughly 20% larger than that of the porphyrins, coupled with the realization that almost identical ionic radii pertain for hexacoordinate $Cd^{2+}$ (r=0.92 Å) and $Gd^{3+}$ (r=0.94 Å),[25] prompted exploration of the general lanthanide binding properties of this new monoanionic porphyrin-like ligand. The synthesis and characterization of a water-stable gadolinium[III] complex derived formally from a new 6,17-dimethyl substituted analogue of the original "expanded porphyrin" system, as well as the preparation and characterization of the corresponding europium(III) and samarium(III) complexes.

The aromatic "expanded porphyrin" system described herein provides an important complement to the existing rich coordination chemistry of porphyrins. For instance, by using methods similar to those described, zinc(II), manganese(II), mercury(II), and neodymium(III) complexes have been prepared and characterized.

The photophysical properties of this new series of tripyrroledimethine-derived "expanded porphyrins" ("texaphyrins") are reported; these compounds show strong low energy optical absorptions in the 690–880 nm spectral range as well as a high triplet quantum yield, and act as efficient photosensitizers for the production of singlet oxygen, for example, in methanol solution.

The present invention involves a major breakthrough in the area of ligand design and synthesis namely synthesis of the first rationally designed aromatic pentadentate macrocyclic ligand, a tripyrroledimethine-derived "expanded porphyrin". This compound, to which the trivial name "texaphyrin" has been assigned, is capable of existing in both its free-base form and of supporting the formation of hydrolytically stable 1:1 complexes with a variety of metal cations, such as $Cd^{2+}$, $Hg^{2+}$, $In^{3+}$, $Y^{3+}$, $Nd^{3+}$, $Eu^{3+}$, $Sm^{3+}$, and $Gd^{3+}$, that are too large to be accommodated in a stable fashion within the 20% smaller tetradentate binding core of the well-studied porphyrins. In addition, since the free-base form of texaphrin is a monoanionic ligand, the texaphyrin complexes formed from divalent and trivalent metal cations remain positively charged at neutral pH. As a result, many of these complexes are quite water soluble—at least far more so than the analogous porphyrin complexes.

The results to date, some of which are summarized herein, indicate strongly that the expanded porphyrin-like macrocycles of the present invention should be efficient photosensitizers for the destruction of free HIV-1 and for the treatment of tumors in vivo and infected mononuclear cells in blood. Altering the polarity and electrical charges of side groups of these macrocycles is anticipated to alter markedly the degree, rate, and perhaps site(s) of binding to free enveloped viruses such as HIV-1 and to virally-infected peripheral mononuclear cells. These substituent changes are also expected to modulate photosensitizer take-up and photosensitization of leukemia or lymphoma cells contaminating bone-marrow as well as by normal cells of the marrow.

EXAMPLE 1

The porphyrins and related tetrapyrrole macrocycles are among the most versatile of tetradentate ligands.[1] Attempts to stabilize higher coordination geometries, however, with larger porphyrin-like aromatic macrocycles have met with little success.[2-5] Indeed, to date, only the uranyl complex of "superphthalocyanine" has been isolated and characterized structurally,[2] although several other large porphyrin-like aromatic macrocycles, including the "sapphyrins",[3,6] "oxosapphyrins",[6,7] "platyrins",[8] "pentaphyrin",[9] and "[26]porphyrin",[10] have been prepared in their metal free forms. This example describes one aspect of the development of a new type of "expanded porphyrin" capable of binding a variety of metal cations. Also described herein is the original synthesis of compound 2,[11] an unprecedented porphyrin-like aromatic pentadentate ligand,[2,12] and the structure of its cadmium (II) bispyridine complex 4. (See FIG. 1 for the structure of compound or complex 1–4)

The present involves preparation of the nonaromatic methylene-bridged macrocycle (compound 1) by the direct acid-catalyzed condensation of 2,5-bis[3-ethyl-5-formyl-4-methylpyrrol-2-yl)methyl]-3,4-diethyl-pyrrole and ortho-phenylenediamine[13] and determined it to be an ineffective cheland.[14] The present inventors have now found that stirring the reduced macrocyclic compound 1 with cadmium chloride for 24 hours in chloroform-methanol (1:2 v.v.) in the presence of air, followed by chromatographic purification on silica gel and recrystallization from chloroform-hexanes, gives the cadmium(II) complex 3.Cl in 24% yield as a dark green powder.[15] Under the reaction conditions both ligand oxidation and metal complexation take place spontaneously.

The structure of compound 3 suggests that it can be formulated as either an 18 π-electron benzannelated [18]annulene or as an overall 22 π-electron system; in either case an aromatic structure is defined. The proton NMR spectrum of complex 3.Cl is consistent with the proposed aromaticity. For the most part, complex 3 Cl shows ligand features which are qualitatively similar to those observed for compound 1. As would be expected in the presence of a strong diamagnetic ring current, however, the alkyl, imine, and aromatic peaks are all shifted to lower field. Furthermore, the bridging methylene signals of compound 1 (at $\delta \cong 4.0$)[13] are replaced by a sharp singlet, at 11.3 ppm, ascribable to the bridging methine protons. The chemical shift of this "meso" signal is greater than that observed for Cd(OEP)[16] ($\delta \cong 10.0$),[17] an appropriate 18 π-electron aromatic reference system, and is quite similar to that observed for the free-base form of decamethylsapphyrin ($\delta \cong 11.5–11.7$),[3] a 22 π-electron pyrrole-containing macrocycle.

The optical spectrum of complex 3.Cl bears some resemblance to those of other aromatic pyrrole-containing macrocycles[3,6,7,18] and provides further support for the proposed aromatic structure. The dominant transition is a Soret-like band at 424 nm ($\epsilon = 72{,}700$), which is considerably less intense than that seen for Cd(OEP)-(pyr)[16] $\lambda_{max} = 421$ nm, $\epsilon = 288{,}000$).[18] This peak is flanked by exceptionally strong N- and Q-like bands at higher and lower energies. As would be expected for a larger π system, both the lowest energy Q-like absorption ($\lambda_{max}$=767.5 nm, $\epsilon$=41,200) and emission ($\lambda_{max}$=792 nm)) bands of complex 3.Cl are substantially red-shifted (by ca. 200 nm) as compared to those of typical cadmium porphyrins.[18,19]

When the above metal insertion was repeated with cadmium nitrate, a complex was obtained in roughly 30% Yield, which, on the basis of microanalytical data,[15] was formulated as the protonated complex 3.NO$_3$.(HNO$_3$) Upon treatment with excess pyridine and recrystallization from chloroform-hexane, the bis-pyridine adduct complex 4-NO$_3$, with spectral properties essentially identical with 3 Cl, was isolated as dark green crystals.[15] The molecular structure of 4-NO$_3$, determined by X-ray diffraction analysis, confirms the aromatic nature of the ligand (FIG. 2).[20] The central five nitrogen donor atoms of complex 4 are essentially coplanar and define a near circular cavity with a center-to-nitrogen radius of ca. 2.39 Å (cf. FIG. 3), which is roughly 20% larger than that found in metalloporphyrins.[21] The Cd atom lies in the plane of the central N$_5$ binding core. The structure of the "expanded porphyrin" 4 thus differs dramatically from that of CdTPP[16,22] or CdTPP-(dioxane)$_2$,[23] in which the cadmium atom lies out of the porphyrin N$_4$ donor plane (by 0.58 and 0.32 Å, respectively). Moreover, in contrast to cadmium porphyrins, for which a five-coordinate square-pyramidal geometry is preferred and to which only a single pyridine molecule will bind,[24] in complex 4-NO$_3$ the cadmium atom is seven-coordinate, being complexed by two apical pyridine ligands. The configuration about the Cd atom is thus pentagonal bipyrimidal; a rare but not unknown geometry for cadmium(II) complexes.[25]

Under neutral conditions complexes 3 and 4 appear to be more stable than cadmium porphyrins: Whereas treatment of CdTPP or CdTPP(pyr) with aqueous Na$_2$S leads to cation loss and precipitation of CdS, in the case of complexes 3 and 4 no demetallation takes place. (Exposure to aqueous acid, however, leads to hydrolysis of the macrocyle.) Indeed, it has not been possible to prepare the free-base ligand 2 by demetallation. The tripyrroledimethine-derived free-base ligand 2 was synthesized directly from 1 by stirring in air-saturated chloroform-methanol containing N,N,N'-tetramethyl-1,8-diaminonaphthalene.[15] Although the yield is low ($\leq$12%),[26] once formed, compound 2 appears to be quite stable: It undergoes decomposition far more slowly than compound 1.[13] Presumably, this is a reflection of the aromatic stabilization present in compound 2. A further indication of the aromatic nature of the free-base "expanded porphyrin" 2 is the observation of an internal pyrrole NH signal at $\delta$=0.90, which is shifted upfield by over 10 ppm as compared to the pyrrolic protons present in the reduced macrocyle 1.[13] This shift parallels that seen when the sp$^3$-linked macrocycle, octaethylporphyrinogen ($\delta$(NH)=6.9),[27] is oxidized to the corresponding porphyrin, H$_2$OEP ($\delta$(NH)=−3.74).[17] This suggests that the diamagnetic ring current present in compound 2 is similar in strength to that of the porphyrins.

The aromatic "expanded porphyrin" system described herein provides an important complement to the existing rich coordination chemistry of porphyrins. For instance, by using methods similar to those described, zinc(II), manganese(II), mercury(II), and neodymium(III) complexes of compound 2[15] have been prepared and characterized.

Literature citations in the following list are incorporated by reference herein for the reasons cited.

REFERENCES

1. The Porphyrins; Dolphin, D., Ed.; Academic Press: New York, 1978–1979; Vols. I–VII.
2. "Superphthalocyanine", a pentaaza aromatic phthalocyanine-like system was prepared by a uranyl-medicated condensation: it is not obtainable as the free-base or in other metal-containing forms: (a) Day, V. W.; Marks, T. J.; Wachter, W. A. J. Am. Chem. Soc. 1975, 97, 4519–4527. (b) Marks, T. J.; Stojakovic, D. R. J. Am. Chem. Soc. 1978, 100, 1695–1705. (c) Cuellar, E. A.; Marks, T. J. Inorg. Chem. 1981, 208, 3766–3770.
3. Bauer, V. J.; Clive, D. R.; Dolphin, D.; Paine, J. B. III; Harris, F. L.; King, M. M.; Loder, J.; Wang, S.-W. C.; Woodward, R. B. J. Am. Chem. Soc. 1983, 105, 6429–6436. To date only tetracoordinated metal complexes have been prepared from these potentially pentadentate ligands.
4. For an example of a porphyrin-like system with a smaller central cavity, see: (a) Vogel, E; Kocher, M.; Schmickler, H.; Lex, J. Angew. Chem. 1986, 98, 262–263; Angew. Chem., Int. Ed. Engl. 1986, 25, 257–258. (b) Vogel, E.; Balci, M.; Pramod, K.; Koch, P.; Lex, J.; Ermer, O. Angew. Chem. 1987, 99,909–912; Angew. Chem., Int. Ed. Engl. 1987, 26, 928–931.
5. Mertes et al. have recently characterized a five-coordinate copper complex of an elegant (but nonaromatic) porphyrin-like "accordion" ligand derived from dipyrromethines: (a) Acholla, F. V.; Mertes, K. B. Tetrahedron Lett. 1984, 3269–3270. (b) Acholla, F. V.; Takusagawa, F.; Mertes, K. B. J. Am. Chem. Soc. 1985, 6902–6908. Four-coordinate copper complexes of other nonaromatic pyrrole-containing macrocycles have also been prepared recently: Adams, H.; Bailey, N. A.; Fenton, D. A.; Moss, S.; Rodriguez de Barbarin, C. 0.; Jones, G. J. Chem. Soc., Dalton Trans. 1986, 693–699.
6. Broadhurst, M. J.; Grigg, R; Johnson, A. W. J. Chem. Soc., Perkin Trans. 1 1972, 2111–2116.
7. (a) Broadhurst, M. J.; Grigg, R.; Johnson, A. W. J. Chem. Soc., Chem. Commun. 1969, 23–24. Broadhurst, M. J.; Grigg, R.; Johnson, A. W. J. Chem. Soc., Chem. Commun. 1969, 1480–1482. Broadhurst, M. J.; Grigg, R.; Johnson, A. W. J. Chem. Soc., Chem. Commun. 1970, 807–809.
8. (a) Berger, R. A.; LeGoff, E. Tetrahedron Lett. 1978, 4225–4228. (b) LeGoff. E.; Weaver, O. G. J. Org. Chem. 1987, 710–711.
9. (a) Rexhausen, H.; Gossauer, A. J. Chem. Soc. Chem. Commun. 1983, 275. (b) Gossauer, A. Bull. Soc. Chim. Belg. 1983, 92, 793–795.
10. Gosmann, M.; Franck, B. Angew. Chem. 1986, 98, 1107–1108; Angew. Chem., Int. Ed. Engl. 1986, 25, 1100–1101.
11. The systematic name for compounds 2 is 4,5,9,24-tetraethyl-10,23-dimethyl-13,20,25,26,27-pentaazapentacyclo[20.2.1.1$^{3,6}$,1$^{8,11}$,0$^{14,19}$]heptacosa-1,3,5,7,9,11(27),12,14,16,18,20,22(25),23-tridecaene.
12. Nonaromatic planar pentadentate pyridine-derived ligands are known. See, for instance: (a) Curtis, N. F. In Coordination Chemistry of Macrocyclic Compounds; Melson, G. A., Ed.; Plenum: New York, 1979; Chapter 4. (b) Nelson, S. M. Pure Appl. Chem. 1980, 52, 2461–2476. (c) Ansell, C. W. G.; Lewis, J.; Raithby, P. R.; Ramsden, J. N.; Schroder, M. J. Chem. Soc., Chem. Commun. 1982, 546–547. (d) Lewis, J.; O'Donoghue, T. D.; Raithby, P. R. J. Chem. Soc., Dalton Trans. 1980, 1383–1389. (e) Constable, E. C.; Chung, L.-Y.; Lewis, J.; Raithby, P. R. J. Chem. Soc., Chem. Commun. 1986, 1719–1720. (f) Constable, E. C.; Holmes, J. M.; McQueen, R. C. S. J. Chem. Soc., Dalton Trans. 1987, 5–8.

13. Sessler, J. L.; Johnson, M. R.; Lynch, V. J. Org. Chem. 1987, 52, 4394–4397.

14. Sessler, J. L.; Johnson, M. R.; Lynch, V.; Murai, T. J. Coord. Chem., in press.

15. Satisfactory spectroscopic, mass spectrometric, and/or analytical data were obtained for all new compounds.

16. OEP = octaethylporphyrin and TPP = tetraphenylporphyrin; the prefixes $H_2$ and Cd refer to the free-base and cadmium(II) forms, respectively; pyr = pyridine.

17. (a) Scheer, H.; Katz, J. J. In Porphyrins and Metalloporphyrins; Smith, K., Ed.; Elsevier: Amsterdam, 1975; Chapter 10. (b) Janson, T. R.; Katz, J. J.; in ref. 1, Vol. IV, Chapter 1.

18. Gouterman, M., in ref. 1, Vol. III, Chapter 1.

19. Becker, R. S.; Allison, J. B. J. Phys. Chem. 1963, 67, 2669.

20. Crystal data: 4.$NO_3$ crystallized from $CHCl_3$-hexanes in the triclinic space group, P1 (no. 1), with a = 9.650 (3) Å, b = 10.217 (4) Å, c = 11.295 (4) Å, $a = 98.16$ (3), $\beta = 107.05$ (2), $\gamma = 92.62$ (3)°, V = 1049.3 (6) Å$^3$, and $\alpha_c = 1.49$ g-cm$^{-3}$ for Z = 1. Unique reflections (5654)(4936 with $F \geq 6\sigma(F)$) using $\omega$ scans were collected at 193K on a Nicolet R3m/V with Mo K$\alpha$ radiation ($\lambda = 0.71069$ Å) out to $2\theta$ of 50°. Data corrected for decay, Lp effects, and absorption. Refined by conventional means to an R = 0.0534. All non-H atoms refined anisotropically. H atom positions calculated ($d_{C-H}$ 0.96 Å) and refined isotropically riding on the relevant C atom. The noncoordinated nitrate ion is within H-bonding distance of the $CHCl_3$ solvent molecule with O . . . C ($CHCl_3$) and O . . . H distances of 3.00(2) Å and 2.46(2) Å, respectively: For full details see Supplementary Material.

21. Hoard, J. L., in ref. 17a, Chapter 8.

22. Hazell, A. Acta Crystallogr., Sect. C: Cryst. Struct. Commun. 1986, C42, 296–299.

23. Rodesiler, P. F.; Griffith, E. H.; Ellis, P. O.; Amma, E. L. J. Chem. Soc. Chem. Commun. 1980, 492–493.

24. (a) Miller, J. R. Dorough, G. D. J. Am. Chem. Soc. 1952, 74, 3977–3981. (b) Kirksey, C. H.; Hambright, P. Inorg. Chem. 1970, 9, 958–960.

25. Compound 4 appears to be the first seven-coordinate cadmium complex derived from all nitrogen donors. For examples of other pentagonal bipyramidal cadmium complexes, see: (a) Cameron, A. F.; Taylor, D. W.; Nuttall, R. H. J. Chem. Soc., Dalton Trans. 1972, 1608–1614. (b) Liles, D. C.; McPartlin, M.; Tasker, P. A.; Lip, H. C.; Lindoy, L. F. J. Chem. Soc., Chem. Commun. 1976, 549–551. (c) Nelson, S. M.; McFall, S. G.; Drew, M. G. B.; Othman, A. H. B.; Mason, N. G. J. Chem. Soc. Chem. Commun. 1977, 167–168. (d) Drew, M. G. B. Othman, A. H. B.; McFall, S. G.; McIlroy, A. D. A.; Nelson, S. M. J. Chem. Soc., Dalton Trans. 1977, 1173–1180. (e) Charles, N. G. Griffith, E. A. H.; Rodesiler, P. F.; Amma, E. L. Inorg. Chem. 1983, 22, 2717–2723.

26. Other oxidants, including DDQ, $Ag_2O$, $I_2$, $PtO_2$, $PbO_2$, $SeO_2$, and $Ph_3CBF_4$, either failed to react or gave rise only to decomposition products.

27. Whitlock, H. W., Jr.; Buchanan, D. H. Tetrahedron Lett. 1969, 42, 3711–3714.

EXAMPLE 2

Although the porphyrins and related tetrapyrrolic compounds remain among the most widely studied of all known macrocycles,[1] relatively little effort has been devoted to the development of larger conjugated pyrrole containing systems.[2-12] Large, or "expanded" porphyrin-like systems, however, are of interest for several reasons: They could serve as possible aromatic analogues of the better studied porphyrins[2-8] or serve as potential biomimetic models for these or other naturally occurring pyrrole-containing systems.[13,14] In addition, large pyrrole containing systems offer exciting possibilities as novel metal binding macrocyles.[2,9-12,15] For instance, suitably designed systems could act as versatile ligands capable of binding larger metal cations and/or stabilizing higher coordination geometries[2,16] than those routinely accommodated within the normally tetradentate ca. 2.0 Å radius porphyrin core.[17] The resulting complexes could have important application in the area of heavy metal chelation therapy or as new vehicles for extending the range and scope of coordination chemistry.[15,18] In recent years a number of potentially pentadentate polypyrrolic aromatic systems, including the "sapphyrins",[3,4] "oxosapphyrins",[5] "smaragdyrins",[3,4] platyrins,[6] and "pentaphyrin"[7] have been prepared and studied as their metal-free forms. For the most part, however, little or no information is available for the corresponding metallated forms. Indeed, the uranyl complex of "superphthalocyanine" was the only metal-containing pentapyrrolic system which has been prepared and characterized structurally.[2] Unfortunately, the "superphthalocyanine" system is apparently not capable of existence in either its free-base or other metal-containing forms.[2] Thus, prior to the present invention, no versatile, structurally characterized, pentadentate aromatic ligands were available,[11] although a number of nonaromatic pyridine-derived pentadentate systems had previously been reported.[19,20] The aspect of this invention described here further shows development of a new class of pyrrole-derived aromatic "expanded porphyrins" capable of binding a variety of metal cations and stabilizing a range of unusual coordination geometries. The present inventors have recently communicated the synthesis of compound $2_A$,[11] (see Example 1) an unprecedented porphyrin-like monoanionic aromatic pentadentate ligand to which has been assigned the trivial name "texaphyrin" (for large Texas-style porphyrin),[18] and the structure of its seven coordinate cadmium(II) bispyridine pentagonal bipyramidal complex $5a_4$. Due to the importance of cadmium complexes in possible chelation based therapeutic applications[21,22] and as potential structural probes for natural metalloproteins (e.g. employing $^{113}$Cd NMR spectroscopy),[23] the coordination properties of the cadmium-containing "texaphyrin" system were investigated further. The present example reports the characterization by single crystal X-ray diffraction analysis of a monoligated six coordinate cadmium(II) benzimidazole pentagonal pyramidal cationic complex 4bA corresponding formally to a coordinatively unsaturated analogue of $5a_4$. The present description, which includes the results of solution base binding ($K_{eq}$) studies for both pyridine (pyr) and benzimidazole (BzIm), constitutes the first structurally documented instance wherein the same macrocyclic ligand has been used to support these two rare, but not unknown,[19] coordination geometries about the same metal cation.[24] See FIG. 4 for the schematic structure of compounds and complexes of the present invention referred to here as $1_A$, $2_A$, $3_A$, $4a_A$, $4b_A$, $5a_A$ and $5b_A$.

Figure 5:
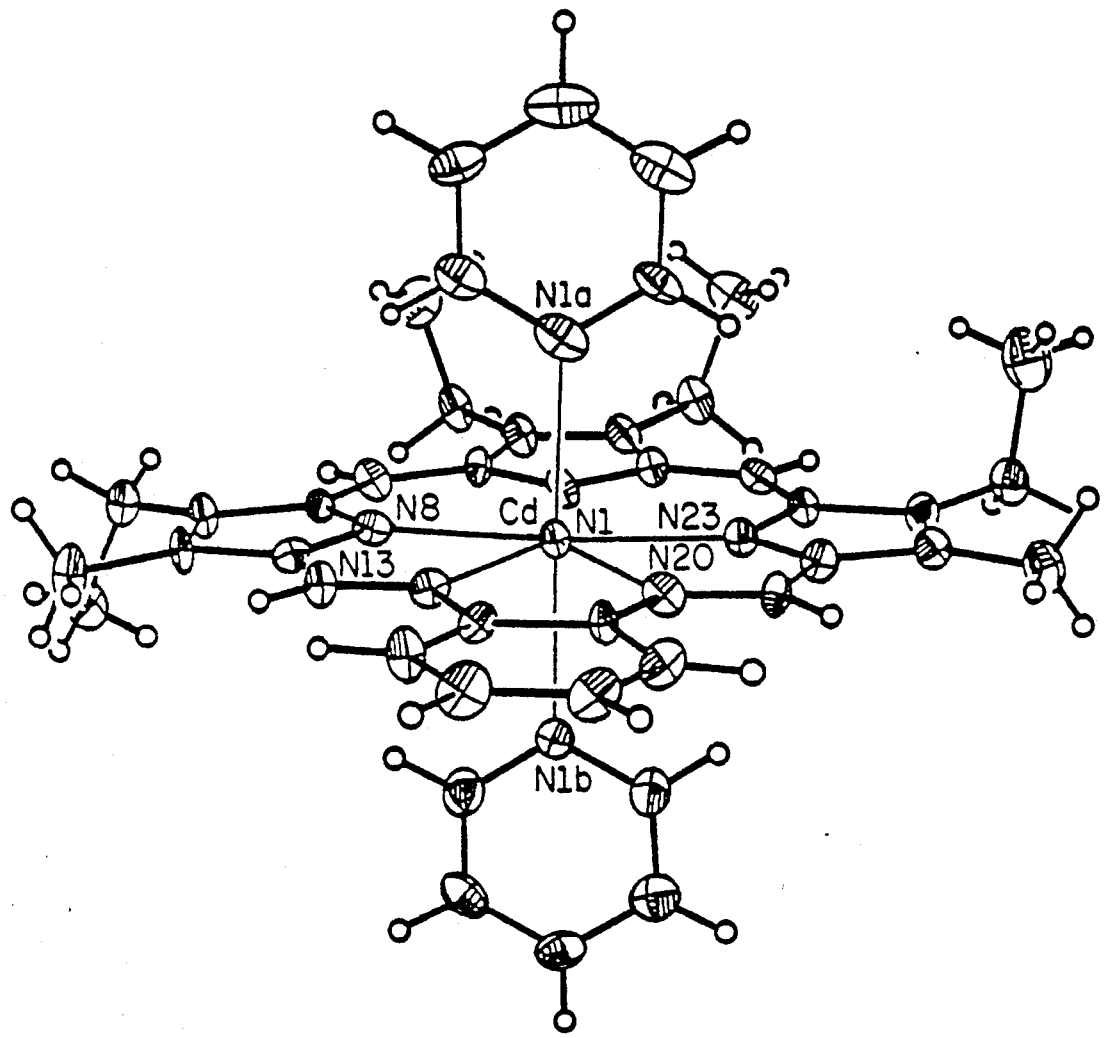
FIG. 5 shows a view of the cation $5_{aA}$ showing pyridine and macrocycle coordination to Cd. Ellipsoids are scaled to the 30% probability level. The cadmium (II) cation lies in the plane of the nearly planar macrocycle (max. deviation from planarity, 0.10(1) Å). Relevant Cd-N bond lengths (Å) are: 2.418(7) N1; 2.268(8) N8; 2.505(7) N13; 2.521(7) N20; 2.248(8) N23; 2.438(14) N1a; 2.473(12) N1b. Selected N-Cd-N bond angles (°) are: 78.9(2) N1-Cd-N8; 80.2(3) N1-Cd-N23; 68.4(2) N8-Cd-N13; 64.4(2) N13-Cd-N20; 68.2(3) N20-Cd-N23; 176.1(4) N1a-Cd-N1b. For further structural details, see ref. 11.

Treatment of the reduced, sp$^3$ form of the macrocyle $(1_A)$[14] with cadmium chloride or cadmium nitrate in air-saturated chloroform-methanol leads in both cases to the formation of green solutions. Following chromatographic purification on silica gel and recrystallization from chloroform-hexanes, the five-coordinate "texaphyrin" chloride or nitrate complexes $3_A$.Cl and $3_A$.NO$_3$ were obtained in analytically pure form (as the demihydrates) in roughly 25% yield. When, however, the metal insertion procedure was carried out (using cadmium nitrate) under reaction and purification conditions identical to those described above, with the exception that chromatography was effected on SEPHADEX, a mixture of crystalline and noncrystalline green solids was obtained. Treatment of this apparently inhomogeneous bulk material, which failed to analyze as a pure five coordinate complex, with excess pyridine and recrystallization from chloroform-hexanes produced the bispyridine complex $5a_A$-NO$_3$ as dark green crystals in essentially quantitative yield. As communicated earlier,[11] (see Example 1) an X-ray crystal diffraction analysis served to confirm the pentagonal bipyramidal coordination geometry postulated for this bisligated seven coordinate complex and the planar pentadentate nature of the macrocyclic "texaphyrin" ligand $2_A$ (c.f. FIG. 5).

Figure 6:
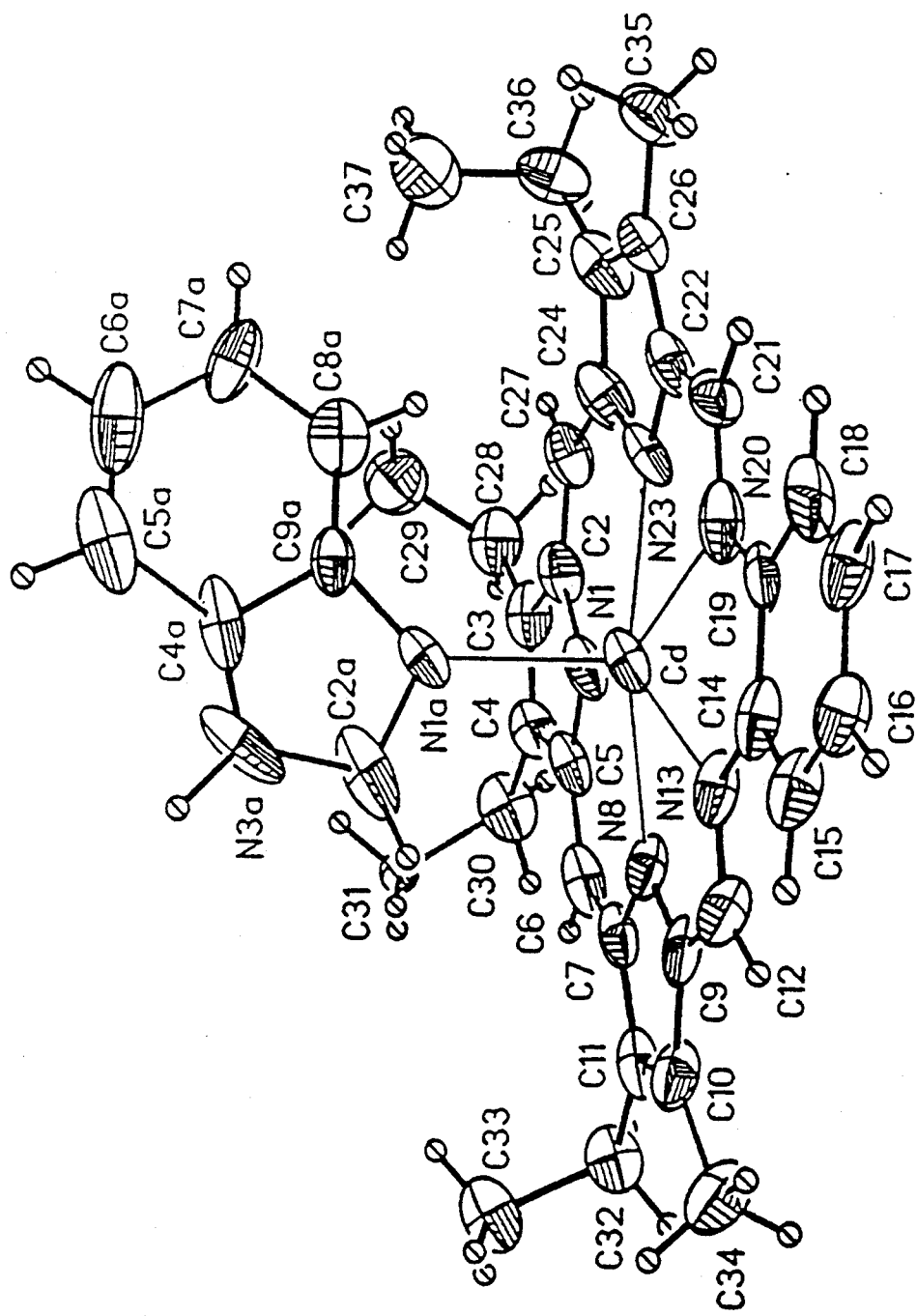
FIG. 6 shows a view of cation $4_{bA}$ showing the atom labelling scheme. Thermal ellipsoids are drawn to 30% probability level. Relevant Cd-N bond lengths (Å) N1 2.462(13); N8 2.254(9); N13 2.535(13); N20 2.526(12); N23 2.298(11); N1A 2.310(9). Selected N-Cd-N bond angles (°): N1-Cd-N8 78.3(4); N8-Cd-N13 67.8(4); N13-Cd-N20 64.1(4); N20-Cd-N23 67.3(4); N1A-Cd-macrocycle N angles range from 93.7(4) to 100.4(3)°. The nitrate counter anion (not shown) is not coordinated to the Cd atom.
Figure 7:
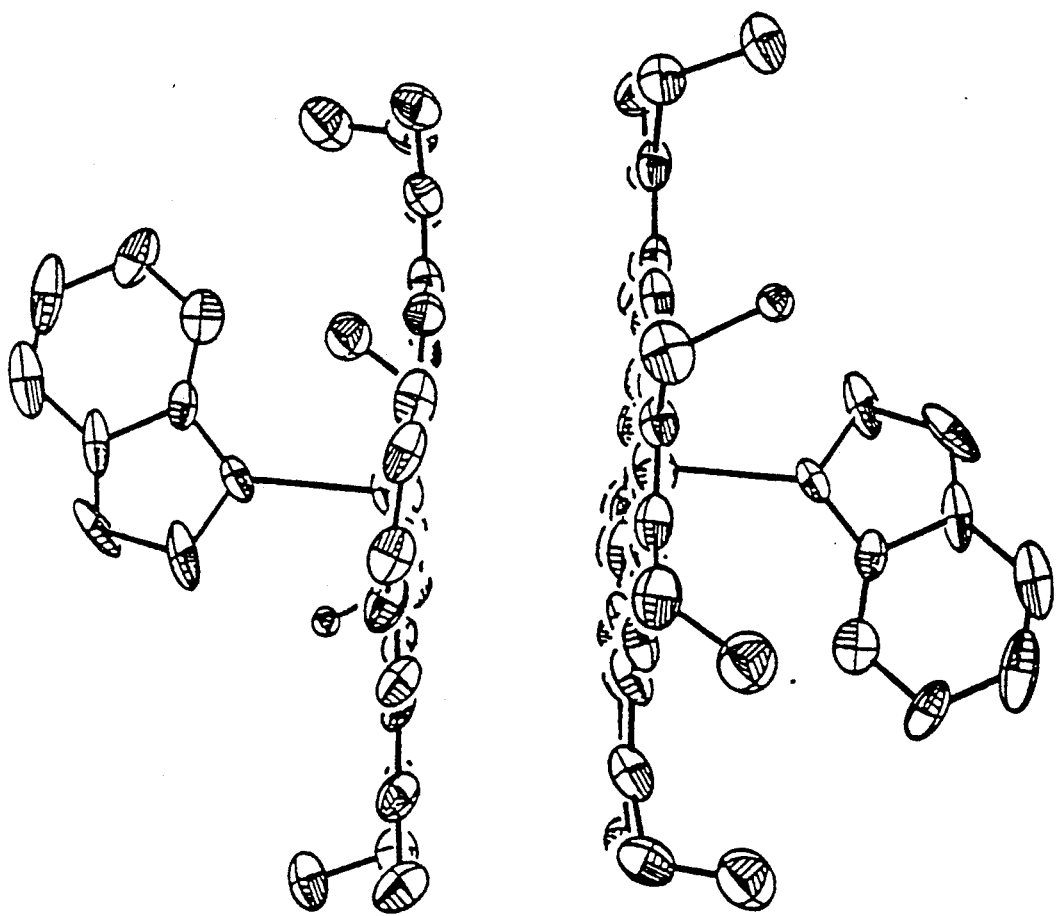
FIG. 7 shows a view along the plane through the macrocycle illustrating the face-to-face stacking of the cation $4_{bA}$ in the unit cell (macrocycle realted by 1-x,y,z). The macrocycle mean planes are separated by 3.38 Å while the Cd...Cd distance is 4.107(1) Å.
Figure 8:
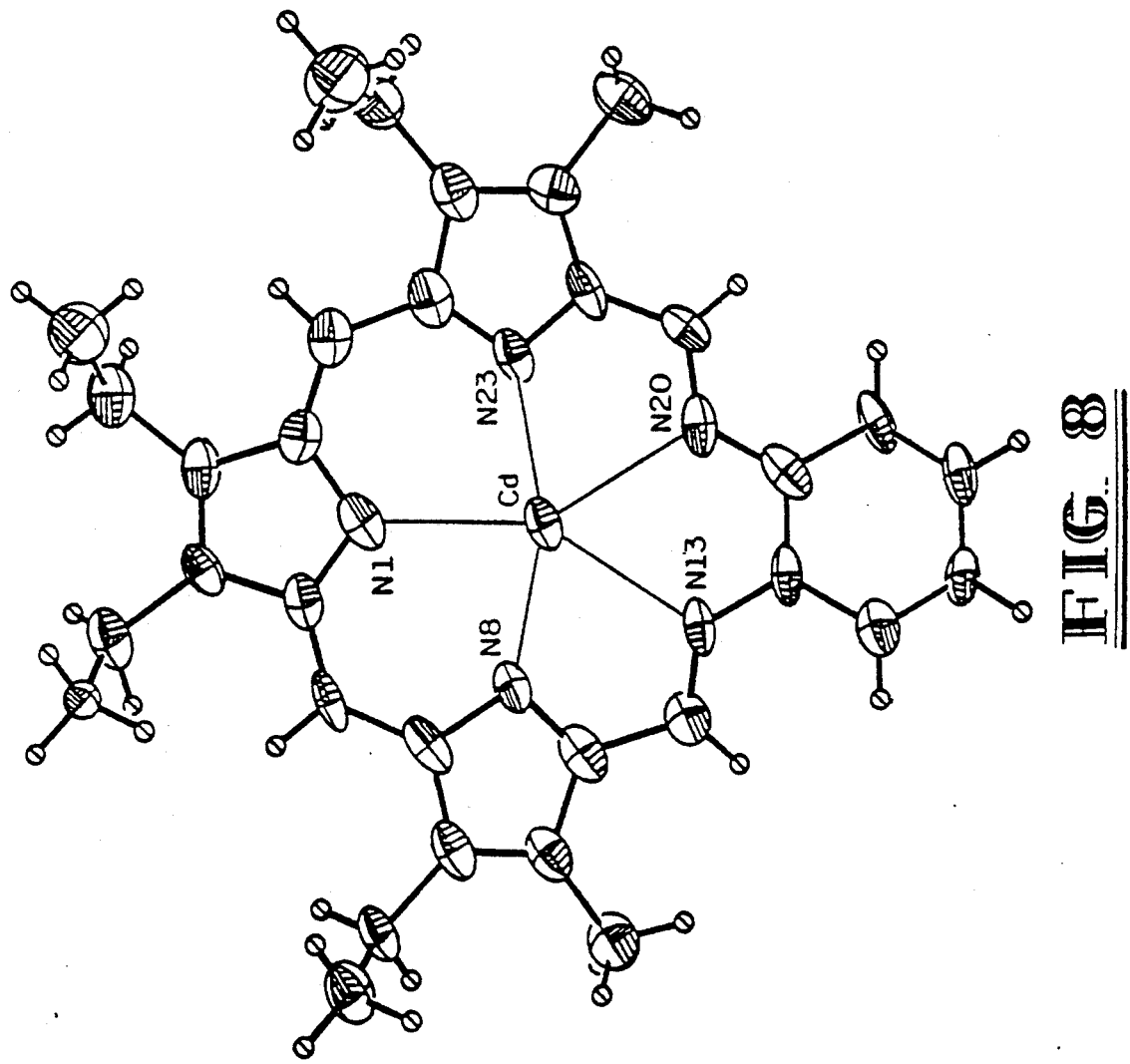
FIG. 8 shows a view of cation $4_{bA}$ perpendicular to the plane through the macrocycle (max. deviation 0.154(13) Å for C15). The Cd atom lies out this plane by 0.334(2) Å. BzIm (not shown) is oriented nearly perpendicular to the macrocycle (dihedral angle of 86.3(3)°) and lies over the pyrrole ring defined by C22, N23, C24, C25, and C26.

As a first step towards determining the nature of the above intermediate product, a single crystal was isolated from the inhomogeneous solid mixture and subject to an X-ray diffraction analysis. The structure so obtained (FIG. 6) was quite unexpected: It revealed a six coordinate pentagonal pyramidal cadmium(II) complex $(4b_A$.NO$_3)$ wherein one of the two possible axial ligation sites is occupied by a bound benzimidazole (BzIm) with the nitrate counter anion not being coordinated to the central Cd atom. The first donor nitrogens of the pentadentate "texaphyrin" macrocycle then serve to complete the coordination sphere about cadmium. As shown in FIG. 6, the 5 donor atoms of the ligand are bound to the Cd atom which lies out of the plane of the macrocycle being displaced by 0.338(4) Å from the N$_5$ donor plane towards the coordinated nitrogen of the benzimidazole ligand. This out of plane distance, which is similar to that seen in CdTPP-(dioxane)[25] (0.32 Å)[26] (but smaller than that observed in CdTPP[27]), is in marked contrast to that observed for the corresponding bispyridine pentagonal bipyramidal adduct $5a_A$-NO$_3$.[11] In this earlier structure, the cadmium(II) cation was found to lie essentially within the plane of macrocycle (c.f. FIG. 5) Cation $4b_A$ further differs from $5a_A$ in that, within the crystal lattice, two molecules stack on one another in a face-to-face fashion (FIG. 7) being separated by van der Waals' distances of ca. 3.38 Å. As a result, the alkyl groups in any given molecule are all displaced to the BzIm-bearing side of the macrocyclic plane. In common with the bispyridine structure,[11] however, in cation $4b_A$ the sp$^2$ atoms of the macrocycle are all essentially planar (FIG. 8) with the maximum deviation from planarity (0.154(13) Å) being found for Cl1. Also in common with complex $5a_A$-NO$_3$, the five ligand nitrogens define a near circular binding cavity with a center-to-nitrogen radius of ca. 2.42 Å, which is roughly 20% larger than that found in metalloporphyrins.[17]

The above structural results support the original formulation of "texaphyrin" $2_A$ as a large 22 $\pi$-electron (or benzannelated 18 x-electron) aromatic porphyrin-like ligand.[28] They also clearly demonstrate that this "expanded porphyrin" is capable of supporting more than one kind of "unusual" coordination geometry about cadmium.

The above structural results also provide insight into the nature of the inhomogeneous cadmium-containing intermediate obtained following metal insertion and sephadex-based purification: At least a portion of this material consists of the six-coordinate BzIm ligated complex $4b_A$. NO$_3$ Although it is certainly plausible to postulate that the coordinated BzIm in cation $4b_A$ derives from ligand degradation reactions associated with metal insertion and accompanying oxidation (presumably involving electrophilic aromatic deacylation of an tripyrrane α-carbon and subsequent condensation with ortho-phenylene diamine), the observation of this six-coordinate species does not establish unambiguously that such BzIm coordination is chemically reasonable. This point is of particular interest since in the presence of excess pyridine, it is the bisligated seven coordinate cationic species $5a_A$ which is favored in the solid state. It was believed to be of importance to determine the solution binding properties of compound $3_A$.NO$_3$ in the presence of both benzimidazole and pyridine. The objective was not only to probe the ligation differences (if any) of these two axial bases but also to define further the nature of the intermediate inhomogeneous solid material formed following Cd insertion and SEPHADEX-based purification, testing in particular the reasonable assumption that this material consists of a mixture of the five and six coordinate cations $3_A$ and $4b_A$.

For a rigorously five coordinate starting cadmium complex, such as that represented schematically by structure $3_A$, where neither the counter anion nor adventitious ligands serves to occupy an apical coordination site, base binding can be considered to occur in accord with equations (1) and (2) shown below. Under conditions where $K_1 \geq K_2$, these processes can be considered to occur sequentially, giving first a monoligated, presumably pentagonal pyramidal six coordinate species (such as $4b_A$), followed by a coordinatively saturated bisligated pentagonal bipyramidal product akin to $5a_A$. Where, however, $K_2 >> K_1$ this stepwise conceptual approach is invalid. Under these conditions, it becomes easier to analyze the base binding in terms of direct formation of the bisligated material as shown in equation (3).

$$L + B \rightleftharpoons LB \quad K_1 = [LB]/[L][B] \qquad (1)$$
$$LB + B \rightleftharpoons LB_2 \quad K_2 = [LB_2]/[LB][B] \qquad (2)$$
$$L + 2B \rightleftharpoons LB_2 \quad K_1K_2 = [LB_2]/[L][B]^2 \qquad (3)$$

In the context of the present study therefore the problem becomes one of finding a solution-based analytical method that will allow changes associated with mono and bis ligation to be probed, and using the accompanying changes to determine as appropriate $K_1$, $K_2$, or $K_1K_2$.

Optical spectroscopy is an important method of characterization for nonlabile metal complexes. In cases where absorption changes accompany ligand binding, optical spectroscopy also provides a convenient means of determining base binding constants.[29] In the case of cadmium tetraphenyl porphyrin (CdTPP), for instance, Miller and Dorough,[30] by monitoring the changes associated with the two low energy Q bands of the absorption spectrum, determined a value for the binding of a single pyridine axial ligand to the unligated four-coordinate starting metalloporphyrin in benzene at 29.9° ($K_1$) of roughly 2,700 $M^{-1}$. Interestingly, these[30] and later workers[31] obtained no evidence for the formation of a bisligated CdTPP-(pyr)$_2$[25] species. Thus, although a pseudo octahedral coordination geometry is defined in the solid state by the weakly bound axial ligands of CdTPP-(dioxane)$_2$,[26] there is no evidence that such a structure is attained in pyridine-containing benzene solution.

Figure 9:
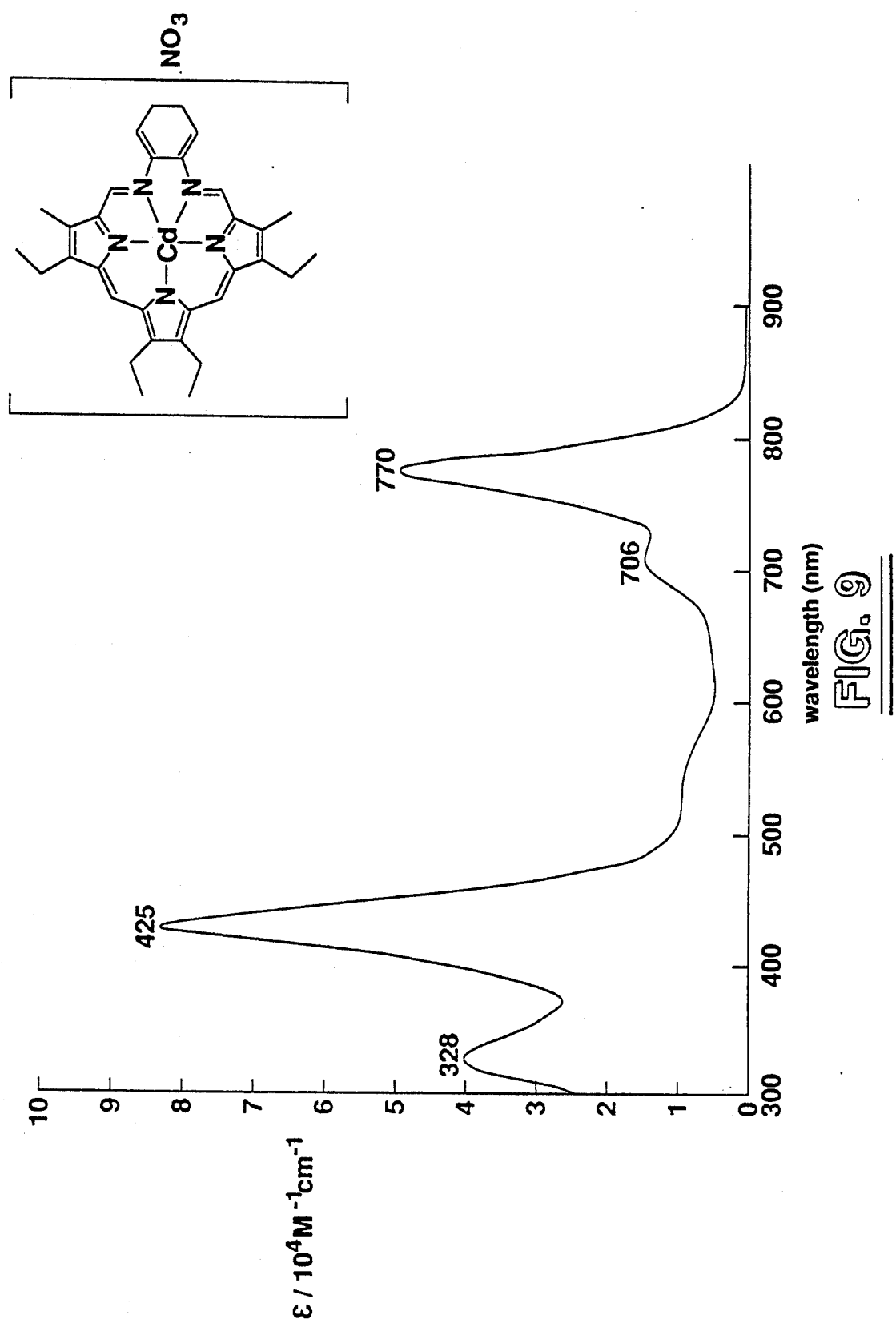
FIG. 9 shows a UV-visible spectrum of $3_A.NO_3$ $1.50 \times 10^{-5}$ M in $CHCl_3$.

The optical spectrum of purified complex $3_A$.NO$_3$ (FIG. 9) bears some elements in common with that of cadmium porphyrins.[30-34] For instance, complex 3A.NO$_3$ in CHCl$_3$ displays a strong Soret-like high energy transition at 425 nm ($\epsilon=82,800$) which is considerably less intense than that seen in cadmium porphyrins (e.g. CdOEP:[25] $\lambda_{max}$ (CHCl$_3$/MeOH v/v 19/1)=406 nm, $\epsilon=272,000$).[35] This complex also displays exceptionally strong flanking N- and Q-like bands at higher and lower energy. The lowest energy Q-like band ($\lambda_{max}=770$ nm, $\epsilon=49,800$) is particularly noteworthy: It is shifted to the red by ca. 200 nm and is almost a factor of four more intense than the lowest energy Q-type transition seen in typical cadmium porphyrins (e.g. CdOEP: $\lambda_{max}$ (CHCl$_3$/MeOH v/v 19/1)=571 nm, $\epsilon=15,400$).[35] We consider such behavior to be reflective of the larger delocalized aromatic system present in the overall 22 $\pi$-electron "texaphyrins" than in the 18 $\pi$-electron porphyrins. Interestingly, the lowest energy transition seen in the cadmium complex of 3,8,12,13,17,22-hexaethyl-2,7,18,23-decamethylsapphyrin in CHCl$_3$ is 701 nm,[35] whereas that seen for the uranyl complex of "superphthalocyanine" is 914 nm.[2b] Thus the lowest energy transition of $3_A$.NO$_3$ lies intermediate in energy between those observed for these two very different 22 $\pi$-electron pentapyrrolic reference systems.

Unfortunately, in spite of the gross qualitative resemblance between the optical spectrum of $3_A$.NO$_3$ and the other pyrrole-containing aromatic macrocycles described above, optical spectroscopy has proved to be an ineffective means of determining the axial ligation properties of cation $3_A$. For instance, addition of excess pyridine to a solution of $3_A$.NO$_3$ in CHCl$_3$ caused only a ca. 1.5 nm red shift in the Soret-like band and a 3.5 nm blue shift of the lowest energy Q-type band. (Similar insignificant changes are also observed upon BzIm addition.) Thus, at least in the case of the cadmium complexes, the optical properties of the "texaphyrin" expanded porphyrin system appear to be largely determined by the overall macrocyclic skeleton and relatively insensitive to changes in the electron environment of the bound cation.

Figure 10:
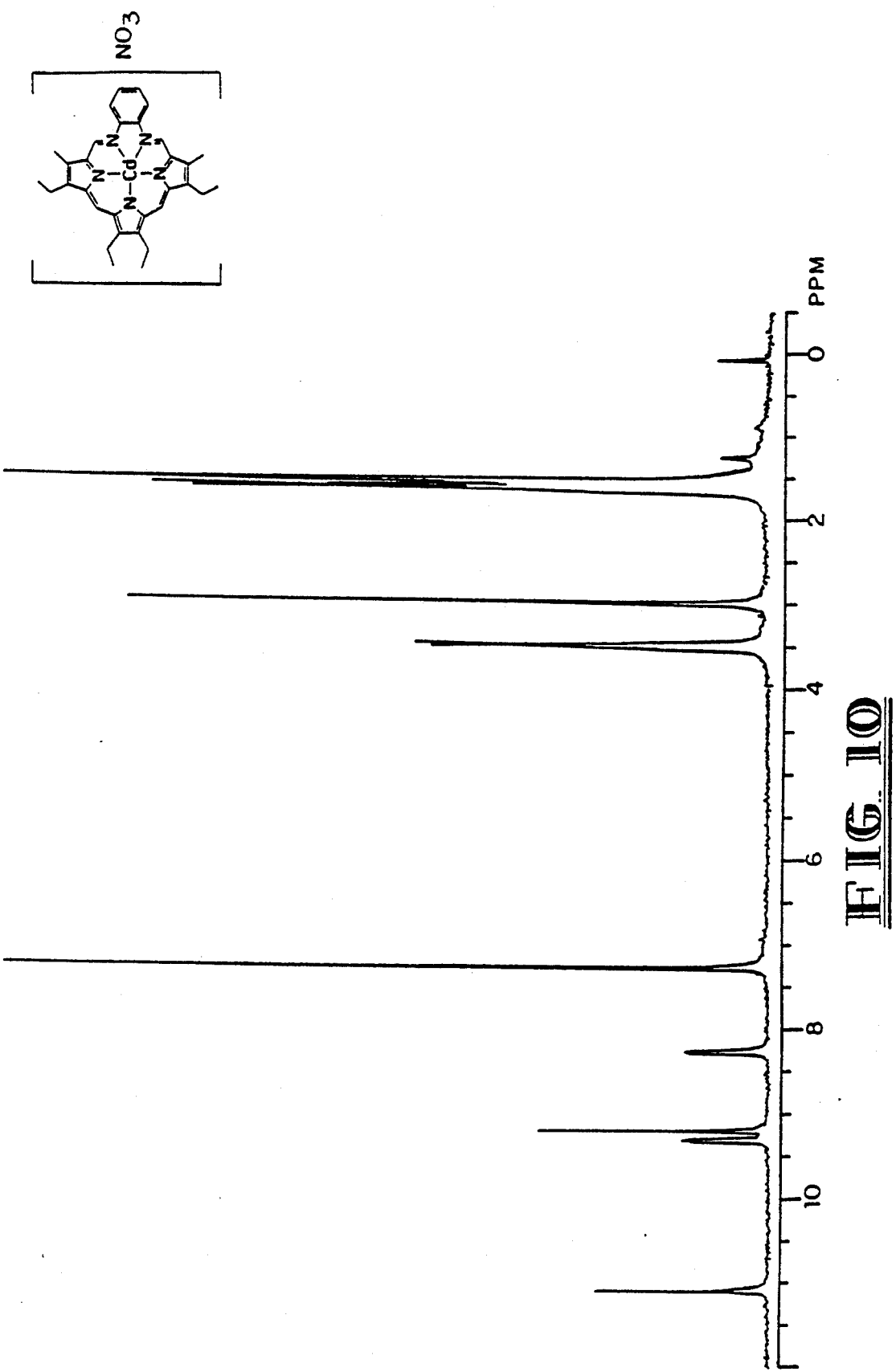
FIG. 10 shows $^1H$ NMR spectrum of $3_A.NO_3$ in $CDCl_3$. The signals at 1.5 and 7.26 ppm represent residual water and solvent peaks respectively.

Cadmium(II) complexes of "texaphyrin" $2_A$ are diamagnetic and hence readily susceptible to study by $^1$H NMR methods. As shown in FIG. 10, the $^1$H NMR of $3_A$.NO$_3$ shows general features which are typical of those expected for a large aromatic pyrrole-containing macrocycle.[36] For instance, as compared to the sp$^3$ form of the ligand (1).[14] the alkyl, imine, and aromatic peaks are all shifted to lower field. Even more diagnostic, however, are the presence of "meso" signals ascribable to the bridging sp$^2$ hybridized methine protons in both the free base "texaphyrin" 2 and its various cadmium containing derivatives 3-5. These bridging protons resonate at ca. 7 ppm lower field than the corresponding bridging methylene signals of the original sp$^3$ form of the ligand ($1_A$).[14] In fact, the "meso" signals of $3_A$.NO$_3$ is found roughly 1 ppm down field from those of typical 8-alkyl substituted cadmium porphyrins (e.g. Cd(O-EP),[25,36] $\delta \approx 10.0$) and approach in value the chemical shifts observed for diamagnetic sapphyrins (e.g., for free-base decamethylsapphyrine,[3] $\delta \approx 11.5$-11.7). Such observations are not unexpected in light of the highly delocalized $\pi$ character postulated for the 22 $\pi$-electron "texaphyrin" systems.

Figure 11:
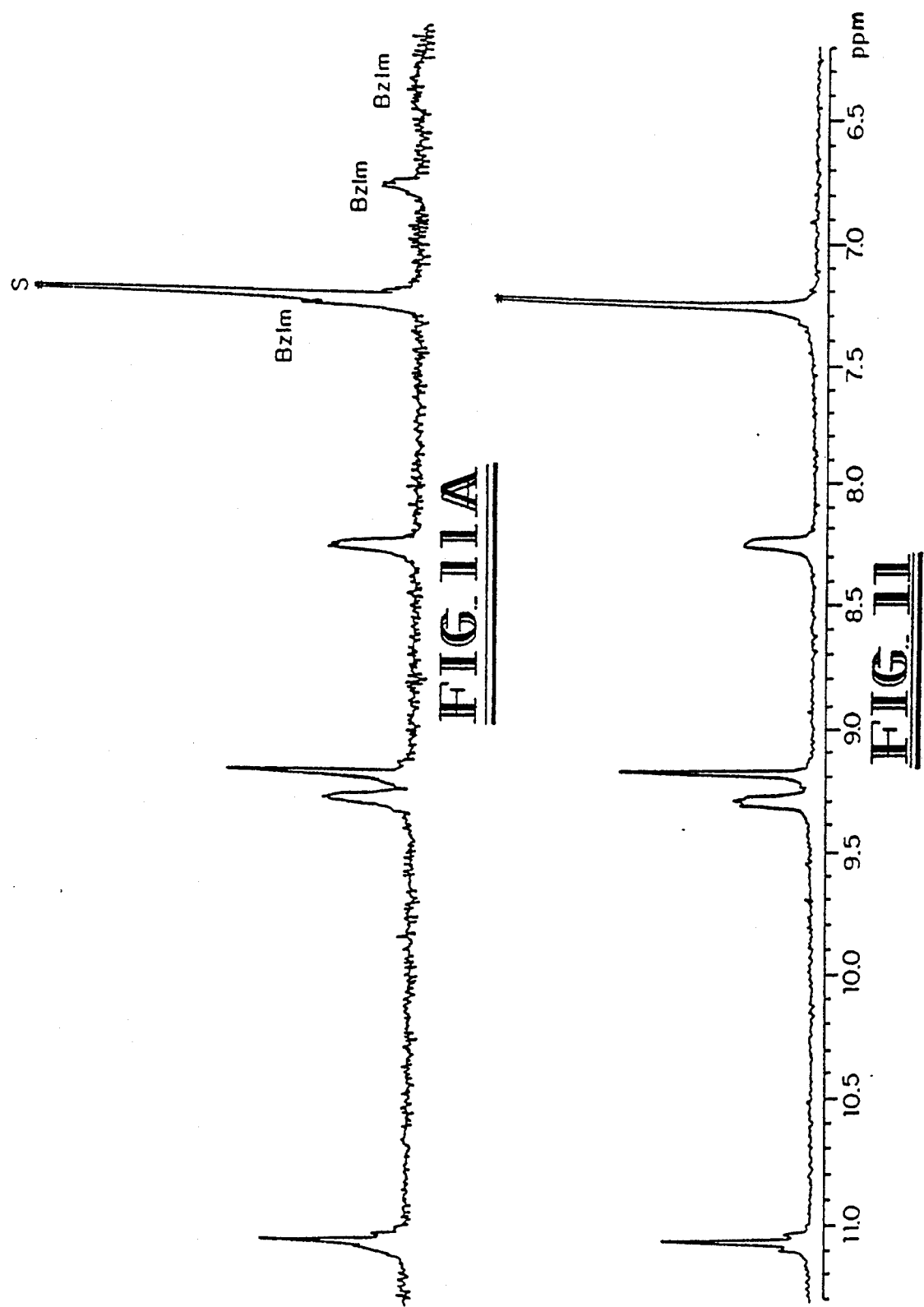
FIG. 11 shows a low field region of the $^1H$ NMR spectra (in $CDCl_3$) of $3_A.NO_3$ (spectrum A) and the bulk inhomogeneous material from which crystals of complex $4b_A.NO_3$ were isolated (spectrum B). The signals marked 'BzIm' ascribed to the bound benzimidazole ligand are observed at 6.4, 6.81, and 7.27 ppm; the signals marked 's' are due to residual solvent.

FIG. 11 provides a comparison of the low field region of the $^1$H NMR spectra of $3_A$.NO$_3$ and the crude material from which the crystals of cation $4b_A$ were obtained. The most striking difference between these two spectra is the presence of a small broad signal at ca. 6.4 ppm and two sharper, more pronounced peaks at 6.81 and 7.27 ppm in the spectrum of the bulk material (trace B in FIG. 11). Although it is tempting to assign these features as signals arising from bound BzIm present in cation $4b_A$, this conclusion is not necessarily obvious: The carbon-bound protons of free BzIm in CDCl$_3$ resonate at 7.25 (m, 2H), 7.75 (m, 2H), and 8.41 (s, 1H) ppm.[37] Although shifts to higher field is expected on binding to cation $3_A$, it is not clear that the expected changes would be as large as those actually observed. A complete spectral titration of complex $3_A$.NO$_3$ with BzIm was therefore undertaken in an effort to address this matter and to assign unambiguously the 6.4, 6.81, and 7.27 ppm signals. The results of these titrations are given in FIGS. 12 and 13.

Figure 12:
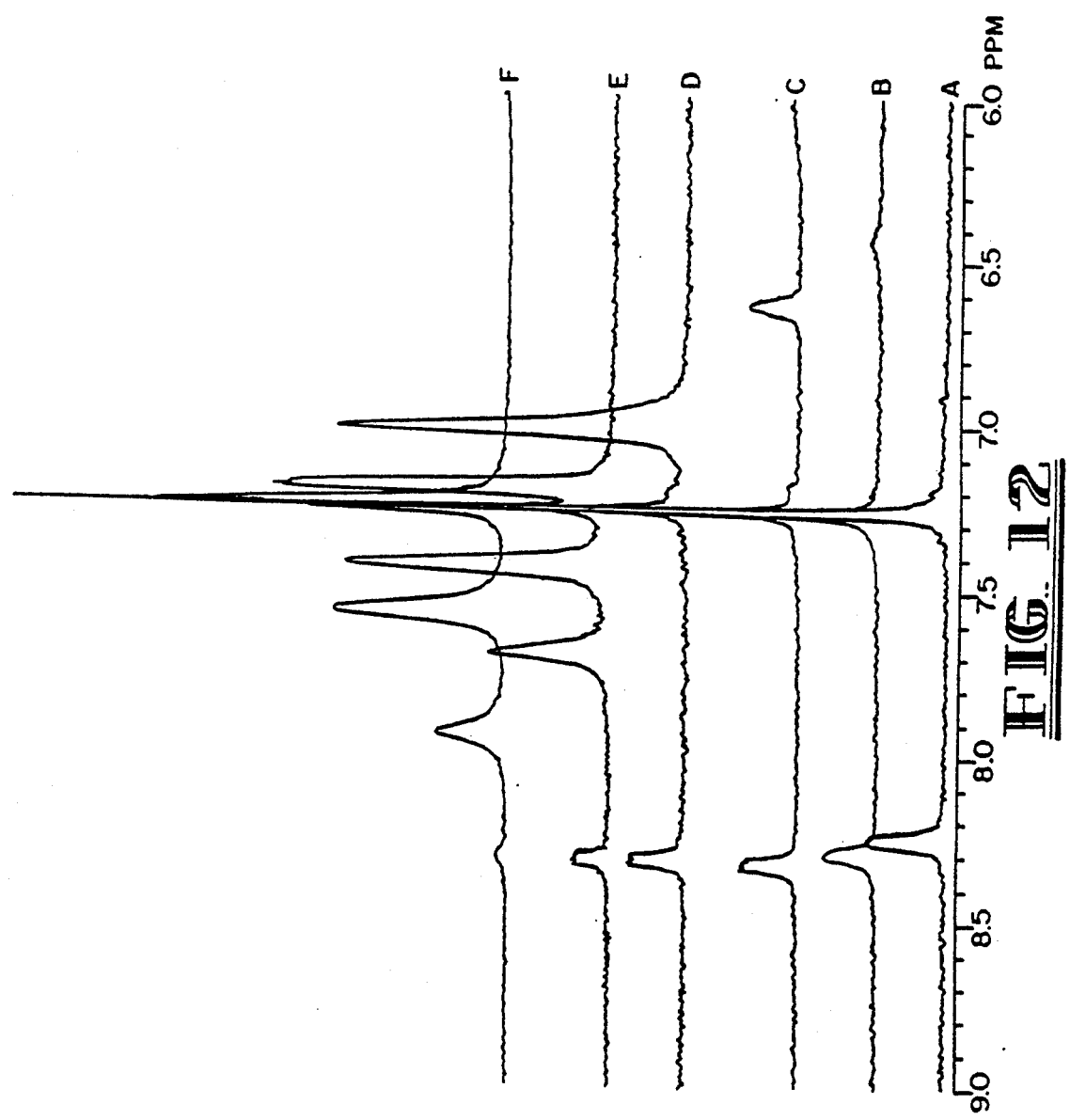
FIG. 12 shows $^1H$ NMR spectral titration of $3_A.NO_3$ (initially $6.85 \times 10^{-3}$ M in $CDCl_3$) with increasing quantities of BzIm showing moderate field region. The BzIm]/[ligand] ratios are 0, 0.2, 0.6, 2.8, 10, and 40 for traces A through F respectively, where [BzIm] and [ligand] represent the total molar concentration of added benzimidazole and starting five-coordinate complex $3_A.NO_3$. The chemical shifts for the BzIm signals in curve C (6.4, 6.62, 7.26 ppm) match well with those seen in the bulk sample from which the crystal of cation 4bA was isolated (c.f. spectrum B of FIG. 8).

A striking feature of the $^1$H NMR titration shown in FIG. 12 is the dramatic change in chemical shift that occurs for the BzIm signals upon complexation to cation $3_A$. Equally important, however, is the observation that the qualitative features of the bulk cadmium containing material discussed above (c.f. FIG. 11, spectrum B) are reproduced upon the addition of roughly 3/5 equivalents of BzIm to purified $3_A$.NO$_3$! This dramatic result provides, in our estimation, unambiguous support for the structural assignment of cation $4b_A$ made on the basis of X-ray diffraction analysis. It also confirms qualitatively the original supposition that the inhomogeneous material isolated after Cd insertion and Sephadex purification does indeed involve an admixture of five and six coordinated species (i.e. $3_A$.NO$_3$ and $4b_A$.NO$_3$).

Figure 13:
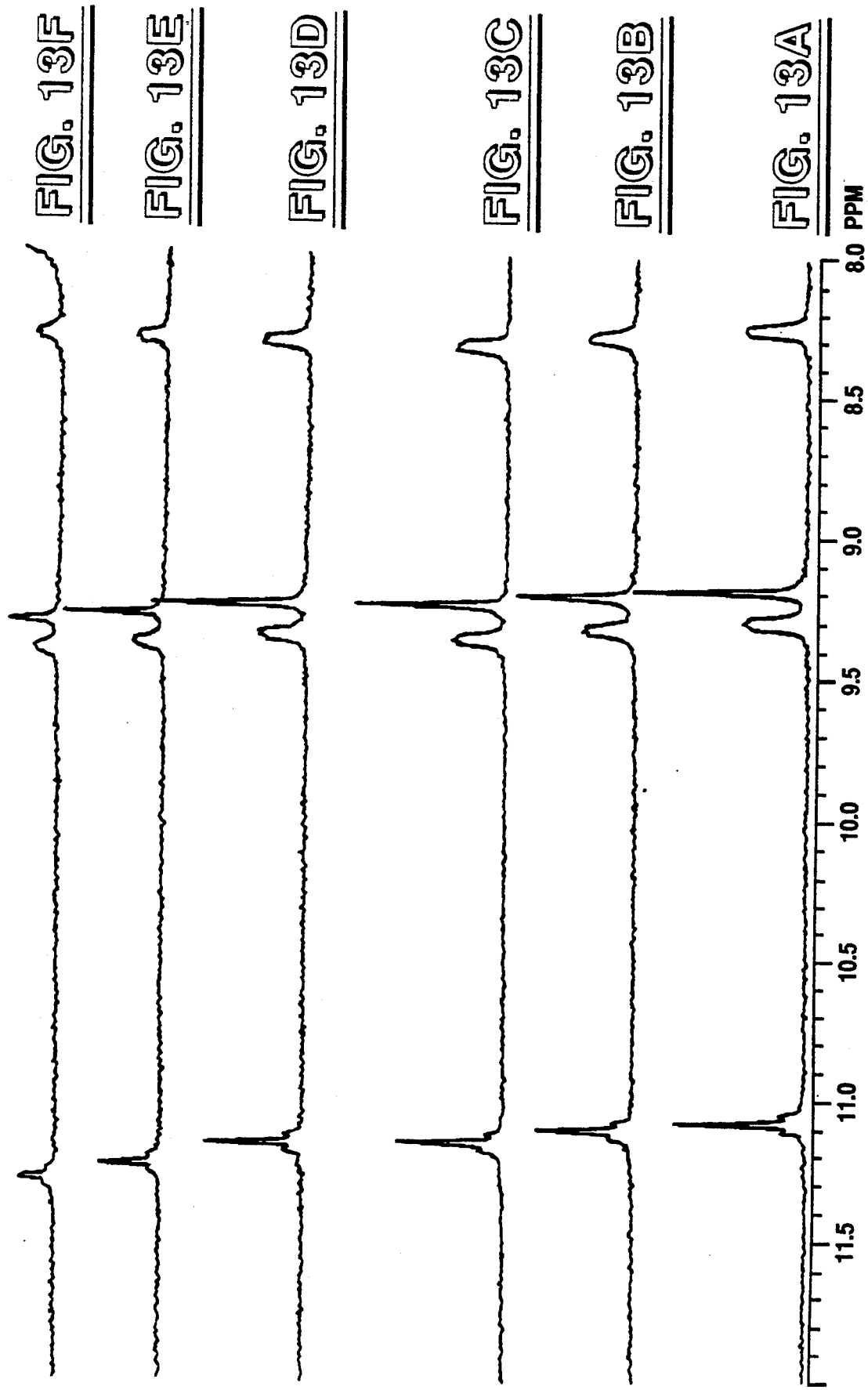
FIG. 13 shows the $^1H$ NMR spectral titration of $3_A.NO_3$ [initially $6.85 \times 10^{-3}$ M in $CDCl_3$) with increasing quantities of BzIm showing changes occurring in high field region. The [BzIm]/[ligand] ratios are 0, 0.2, 0.6, 2.8, 10, and 40 for traces A through F respectively, where BzIm] and [ligand] represent the total molar concentration of added benzimidazole and starting five-coordinate complex $3_A.NO_3$.
Figure 14:
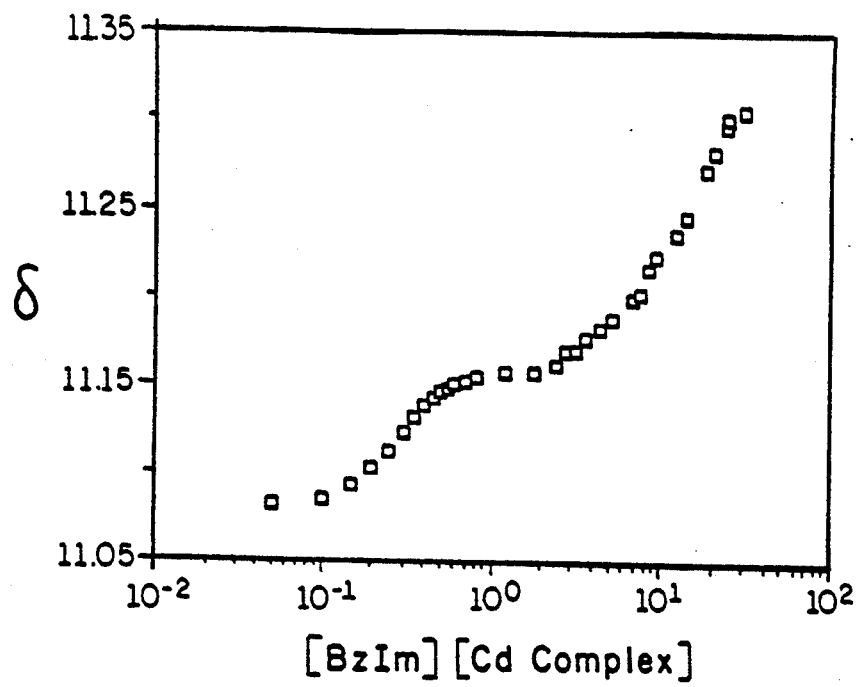
FIG. 14 shows changes in the $^1H$ NMR chemical shift of the "meso" signal for $3_A.NO_3$ plotted as a function of increasing [BzIm]. The terms [BzIm] and [ligand] represent the total molar concentration of added benzimidazole and starting five-coordinate complex 3A $NO_3$.

For quantitative $K_{eq}$ determinations it proved easiest to monitor the changes associated with the "meso" signals. Here, sharp peaks, indicative of fast ligand exchange,[29,38] and reasonably large changes in chemical shift were observed (FIG. 13). In addition, no interfering BzIm-based resonances are found in this region. In FIG. 14 the changes in chemical shift for the "meso" protons in complex $3_A$.NO$_3$ are plotted as a function of added BzIm. The resulting titration curve shows, that at least for this base, axial ligation can be considered as occurring in two essentially independent stepwise binding processes. Standard analysis[38] of the data at both very low and very high conversion gave values of $K_1=1.8\pm0.2\times10^4$ and $K_2=13\pm3$.

Just as was the case for BzIm, addition of pyridine to the five coordinate complex $3_A$.NO$_3$ gave rise to easily detected and well-defined changes in the chemical shift of the "meso" signals (FIG. 15). In marked contrast to the results obtained with BzIm, however, ligation in this case cannot be considered to be occurring in a discrete stepwise manner. This is quite apparent from an inspection of FIG. 13 in which the changes in chemical shift for the "meso" protons in complex $3_A$.NO$_3$ are plotted as a function of increasing pyridine concentration.

Analysis of this binding isotherm using standard methods[38] then gave values of $K_1 \approx 1.6$ $M^{-1}$ and $K_1K_2=315\pm30$ $M^{-2}$.

The above $K_1$ and $K_2$ (or $K_1K_2$) values are predicated on the assumption that the cadmium complexes under discussion are stable with regards to demetallation and that the equilibria of equations 1 and 2 (or 3) pertain under the conditions of base binding. The first of these concerns is readily apparent: If demetallation occurs, then obviously one is not studying base binding! All control experiments, however, suggested that the cadmium complexes derived from the "texaphyrin" ligand are many orders of magnitude more stable than those of the considerably smaller porphyrins. In fact, demetallation does not occur even when the complexes are challenged with excess sulfide anion (which serves to demetallate CdTPP[25,35]);[39] it thus appears unlikely that such a process will occur in the presence of pyridine or benzimidazole. The second concern is particularly important within the context of quantitative work: If, for instance, the starting complex $3 \cdot NO_3$ is not rigorously five coordinate, then $K_1$ (and perhaps $K_2$ as well) would represent an axial ligand displacement reaction rather than a pure addition process as implied above. Control experiments indicate that the assumption of initial five coordination is reasonable: Independent titrations of $3_A \cdot NO_3$ with $NH_4NO_3$ and $H_2O$ indicate that only modest and monotonic changes in the chemical shift of the "meso" signals take place over the course of adding $\geq 50$ equivalents of these potentially adventitious ligands.[40] This means that either "complete" binding occurs at 1:1 stoichiometry (essentially ruled out in the case of $H_2O$ on the basis of analytical data), or that these species are poorly coordinating in $CHCl_3$ so that five coordination pertains about cadmium; the latter interpretation appearing more likely.

To the extent that the above assumptions are valid, the $K_{eq}$ values obtained for BzIm and pyr binding in solution provide an accurate reflection of the coordination behavior observed in the solid state. For instance, at the concentrations used for the $^1H$ NMR titration experiments (ca. $5 \times 10^{-3}$ M) complex $3_A \cdot NO_3$ will be roughly 20% converted to the six coordinate form ($4b_A \cdot NO_3$) following the addition of only 0.2 molar equivalents of BzIm, and 90% converted after the addition of 1.0 molar equivalent. Interestingly, even in the presence of 10 molar equivalents, the resulting monoligated species $4b_A$ will only be 35% converted to the corresponding bisligated seven coordinate form ($5b_A$). Thus for benzimidazole a large concentration range pertains in solution wherein in the monoligated cationic complex $4b_A$ is the dominant species. The equilibrium data also showed, however, that in solution it will always be, either the bisligated species $5a_A$ or unligated starting complex $3_A$ which dominates in the presence of excess pyridine. For instance, under the conditions of the $^1H$ NMR titrations, complex $3_A \cdot NO_3$ will be roughly 5% converted to pentagonal bipyramidal product $5a_A \cdot NO_3$ after the addition of 3 equivalents of pyridine and roughly 35% converted to this species after the addition of 10 equivalents.

Both steric and electronic factors may be invoked to explain the different ligation properties for pyridine and benzimidazole. Considerable work with metalloporphyrins, particularly in the context of heme model chemistry,[41] has served to establish the stronger coordinating abilities of imidazole type ligands relative to pyridine-type bases, an observation that is generally ascribed to the poorer $\pi$ basicity of the latter systems.[41a,42] Thus the high $K_1$ value (relative to pyridine) observed for BzIm binding to cation $3_A$ comes as little surprise. What is more puzzling, however, is the observation that $K_2$ for this base is so low: At first glance it appears unreasonable that monoligation would be stable in the presence of this stronger $\pi$ base since preferential conversion to the coordinatively saturated seven coordinate species occurs in the presence of pyridine. An inspection of the crystal structure shown in FIG. 6, however, provides the basis for an explanation: The BzIm residue lies nearly perpendicular to the macrocycle in $4b_A$ and is oriented over the pyrrole ring containing N23. As a result, H8A of the BzIm base is in close proximity to several atoms of this ring, making close contacts (Å) with N23 (2.65(2)), C24 (2.69(2)), and C22 (2.81(2)). Thus, as has been well-documented in the case of heme models and encumbered imidazoles,[41b,43] steric hindrance appears to be the fundamental factor favoring 6-coordination in the presence of excess BzIm. Thus both steric and electronic effects serve to differentiate the ostensibly very different binding behavior of BzIm and pyr in the present "expanded porphyrin" system. Such effects also provide inter alia a rationale for the formation and selective isolation, in the solid state, of complexes $4b_A \cdot NO_3$ and $5a_A \cdot NO_3$.

The pentadentate 22 $\pi$-electron porphyrin-like "texaphyrin" macrocycle is an effective and versatile ligand for cadmium(II). It is capable of supporting the formation of three rare coordination geometries for this cation, namely, pentagonal, pentagonal pyramidal, and pentagonal bipyramidal. Whereas the first of these forms is currently only inferred on the basis of analytical and solution phase studies, the latter two geometries have been characterized both in solution and in the solid state by single crystal X-ray diffraction analyses. The "texaphyrin" system thus represents, to the best of our knowledge, the first structurally documented system capable of supporting both pentagonal pyramidal and pentagonal bipyramidal geometries about the same central metal cation. This unique cheland also endows these cadmium complexes with several other important properties. These include an optical spectrum with an unusually low energy Q-type band, and a stability with regards to demetallation which far exceeds that of the corresponding cadmium(II) porphyrins. The first of these properties suggests that the present "texaphyrin" ($2_A$) or other "expanded porphyrin" systems should find important application in the areas of photodynamic therapy or photosynthetic modelling studies where low energy absorption properties would be beneficial.[44] The second property suggests that systems similar to those presently described might provide the basis for the development of effective chelation-based detoxification therapies for cadmium, a metal presently ranking only behind mercury and lead in toxicological importance,[21] and one for which few, if any, therapies currently exist.[22]

Electronic spectra were recorded on a Beckman DU-7 spectrophotometer. Proton and $^{13}C$ NMR spectra were obtained in $CDCl_3$ using $CHCl_3$ ($\delta=7.26$ ppm for $^1H$; 77.0 ppm for $^{13}C$) as an internal standard. Proton NMR spectra were recorded on either Nicolet NT-360 (360 MHz), or General Electric QE-300 (300 MHz) spectrometer. Carbon spectra were measured at 125 MHz using the Nicolet NT-500 spectrometer. Fast atom bombardment mass spectrometry (FAB MS) was performed using a Finnigan-MAT TSQ-70 instrument and 3-nitrobenzyl alcohol as the matrix. Elementary analyses were performed by Galbraith Laboratories. X-ray structures were solved as described below and in references 11 and 14.

All solvents and reagents were of reagent grade quality, purchased commercially, and used without further purification. Sigma lipophilic Sephadex (LH-20-100) and Merck type 60 (230-400 mesh) silica gel were used for column chromatography. The sp$^3$ form of the ligand ($1_A$) was prepared in $\geq 90\%$ yield using the acid catalyzed method described earlier.[14] The currently higher yield does not derive from a fundamental change in procedure but simply reflects a greater experience with this particular key reaction.

Preparation of 4,5,9,24-tetraethyl-10, 23-dimethyl-13,20,25,26,27-pentaazapentacyclo [20.2.1.1$^{3,6}$.1$^{8,11}$.0$^{14,19}$]heptacosa-1,3,5,7,9,11(27), 12,14,16,18,20,22(25),23-tridecaene, free-base "texaphyrin" $2_A$. Macrocycle $1_A^{14}$ (50 mg, 0.1 mmol) was stirred in methanol/chloroform (150 ml, v/v 2/1) in the presence of N,N,N',N'-tetramethyl-1,8-diaminonaphthalene ("proton sponge") for one day at room temperature. The reaction mixture was then poured into ice water. The organic layer was separated and washed with aqueous ammonium chloride solution and then brine. Following concentrations on a rotary evaporator, the crude material was purified by chromatography on SEPHADEX using first pure chloroform and then chloroform/methanol (v/v/ 10/1) as eluents. After several faster red bands were discarded, a dark green band was collected, concentrated in vacuo, and recrystallized from chloroform/n-hexane to give the sp$^2$ form of the ligand as a dark green powder in yields ranging from 3-12% with the better yields only being obtained on rare occasions. For $2_A$: $^1$H-NMR (CDCl$_3$) $\delta = 0.90$ ($^1$H, br.s, NH), 1.6-1.8 (12H, m, CH$_2$CH$_3$), 3.05 (6H, s, CH$_3$), 3.42-3.58 (8H, m, CH$_2$CH$_3$), 8.25 (2H, m, phen. CH), 9.21 (2H, s, CH=N, 9.45 (2H, m, phen. CH), 11.25 (2H, s, CH=C); C.I. MS (CH$_4$) 491 (calcd for C$_{32}$H$_{35}$N$_5$·H$^+$: 490); FAB MS (3-nitrobenzyl alcohol matrix, 8 keV acceleration): m/e 512 (calcd for C$_{32}$H$_{34}$N$_5$Na: 512); IR (KBr) $\nu = 3420, 2960, 2920, 2860, 1600, 1560, 1540, 1370, 1350, 1255, 1210, 1080, 1050, 980, 940, 905, 750$ cm$^{-1}$; UV/VIS (CHCl$_3$) $\lambda_{max}$ nm ($\epsilon$) 327.0 (30,700); 422.5 (60,500]; 692.0 (10,100); 752.0 (36,400).

Attempts at binding cadmium with ligand $2_A$ were conducted. Several milligrams of compound $2_A$ were stirred with an excess of cadmium chloride in chloroform/methanol as per the direct insertion methods outlined above. Even after 2 days, however, UV/VIS (monitoring the Q-type band at 751), indicated that little or no metal insertion had taken place. Due to the difficulty of preparing compound or ligand $2_A$ and the obvious success of the direct insertion procedures described herein, no attempts were made to examine other metallation methods.

The preparation of complex $3_A$.Cl was as follows. The sp$^3$ form of the ligand ($1_A$)$^{14}$ (40 mg, 0.08 mmol) was stirred with cadmium chloride (21.4 mg, 0.08 mmol) in chloroform/methanol (150 ml, v/v 2/1) for 1 day. The dark green reaction mixture was concentrated under reduced pressure on a rotary evaporator and chromatographed through silica gel using first pure chloroform and then chloroform/methanol (v/v 10/1) as eluents. After discarding several leading red bands, the dark green band was collected and taken to dryness in vacuo to give compound $3_A$.Cl. This material was recrystallized from chloroform/n-hexane to give analytical pure compound $3_A$.Cl as a dark green powder in 24% yield. For $3_A$.Cl: $^1$H-NMR (CDCl$_3$) $\delta = 1.55-1.67$ (12H, m, CH$_2$CH$_3$), 3.03 (6H, s, CH$_3$), 3.04-3.55 (8H, m, CH$_2$CH$_3$), 8.27 (2H, m, phen. CH), 9.23 (2H, s, CH=N), 9.40 (2H, m, phen. CH), 11.30 (2H, s, CH=C); $^{13}$C NMR (CDCl$_3$) $\delta = 9.8, 17.3, 18.1, 19.1, 19.2, 117.6, 117.8, 128.4, 132.7, 138.2, 139.3, 145.4, 146.7, 150.5, 153.5, 155.0$; FAB MS (3-nitrobenzyl alcohol matrix, 8 keV acceleration): m/e 602 ($^{114}$Cd, M$^+$, 100), 601 ($^{113}$Cd, M$^+$, 64), 600 ($^{112}$Cd, M$^+$, 84); IR (KBr) $\nu = 2950, 2910, 2855, 1635, 1605, 1380, 1255, 1210, 1090, 1010, 795$ cm$^{-1}$; UV/VIS $\lambda_{max}$ nm ($\epsilon$) 327.0 (32,800); 424.0 (72,700); 704.5 (11,000); 767.5 (41,200); anal. calcd for C$_{32}$H$_{34}$N$_5$Cd·Cl·(1/2·H$_2$O) C, 59.54; H, 5.46; N, 10.85. Found: C, 59.78; H, 5.32; N, 10.80.

The preparation of complex $3_A$.NO$_3$ was as follows. The sp$^3$ form the ligand ($1_A$)$^{14}$ (40 mg, 0.08 mmol) was stirred with cadmium nitrate tetrahydrate (31 mg, 0.1 mmol) in chloroform/methanol (150 ml, v/v =1/2) for 1 day. The dark green reaction mixture was then concentrated and purified by chromatography on silica gel as described above. The resulting crude material was then recrystallized from chloroform/n-hexane to give analytical pure 3.NO$_3$ in 27% yield.[45] For $3_A$.NO$_3$: $^1$H NMR (CDCl$_3$): $\delta = 1.55-1.70$ (12H, m, CH$_2$CH$_3$), 3.04 (6H, s, CH$_3$), 3.42-3.55 (8H, m, CH$_2$CH$_3$), 8.27 (2H, m, phen. CH), 9.20 (2H, S, CH=N), 9.30 (2H, m, Phen. CH), 11.07 (2H, s, CH=C); FAB MS (3-nitrobenzyl alcohol matrix, 8KeV acceleration): m/e 602 ($^{114}$Cd, M$^+$, 100), 601 ($^{113}$Cd, M$^+$, 61), 600 ($^{112}$Cd, M$^+$, 87): IR (KBr) $\nu = 2960, 2920, 2860, 1600, 1550, 1440, 1375, 1200, 1130, 1075, 1040, 975, 930, 900, 740$ cm$^{-1}$; UV/Vis $\lambda_{max}$ nm ($\epsilon$) =328.0 (39,900), 425.0 (82,800), 706.0 (14,400), 770 (49,800); Anal. calcd for C$_{32}$H$_{34}$N$_5$Cd·NO$_3$·($\frac{1}{2}$H$_2$0) C, 57.19; H, 5.25; N, 12.50. Found: C, 57.12; H, 5.19; N, 11.80.

Attempts to demetallate complex $3_A$.NO$_3$ were made. In an effort to obtain the free sp$^2$ bridged ligand $2_A$, the above complex in chloroform was stirred for several hours in the presence of sodium sulfide and independently with sodium thiosulfate. No significant changes in optical properties were observed. Although this did not rule out the possibility that changes in axial ligation might be taking place, these observations provided reasonable evidence that little or no demetallation occurs under the reaction conditions. In the case of sodium sulfide, this critical conclusion was further supported by FAB MS: Other than the starting cationic complex $3_A$, no evidence was obtained for any moderate to high molecular weight volatile products in the mass spectrum. When subject to treatment with aqueous acid, complex $3_A$.NO$_3$ appears to undergo hydrolysis (at the imine residues) and hence demetallation. The rate of this process, however, is strongly pH dependent, the half-life being, for instance, on the order of several hours in the presence of ca. 0.1 N HCl.

Preparation and isolation of complex $4b_A$.NO$_3$ The sp$^3$ form of the ligand ($1_A$) (40 mg, 0.08 mmol) was stirred with cadmium nitrate tetrahydrate (31 mg, 0.1 mmol) in chloroform/methanol (150 ml, v/v =$\frac{1}{2}$) for 1 day. The dark green reaction mixture was concentrated on a rotary evaporator and chromatographed through Sephadex using first neat chloroform and then chloroform/methanol (v/v 10/1) as eluents. After discarding several leading red bands, the dark green band was collected and concentrated to give a dark green solid. This was recrystallized from chloroform/n-hexane to give a mixture of crystalline and noncrystalline solids in 27% yield. For this bulk material: $^1$H-NMR (CDCl$_3$) $\delta = 1.55$–1.72 (12H, m, CH$_2$C$\underline{\text{H}}_3$), 3.04 (6H, s, CH$_3$), 3.45–3.58 (8H, m, C$\underline{\text{H}}_2$CH$_3$), 6.4 (ca. 3/5H, br. s, BzIm), 6.81(ca. 6/5H, br. s., BzIm), 7.27 (ca. 6/5H, s, BzIm), 829 (2H, m, phen. CH), 9.21 (2H, s, C$\underline{\text{H}}$=N), 9.32 (2H, m, phen. CH), 11.08 (2H, s, C$\underline{\text{H}}$=C); FAB MS (3-nitrobenzyl alcohol matrix, 8 keV acceleration): m/e 602 ($^{114}$Cd, M$^+$, 100), 601 ($^{113}$Cd, M$^+$, 67), 600 ($^{112}$Cd, M$^+$, 78); IR (KBr) $\nu = 2970$, 2935, 2875, 1560, 1382, 1356, 1300, 1258, 1212, 1085, 1050, 985, 910, 755 cm$^{-1}$; uv/vis $\lambda_{max}$ nm ($\epsilon$) 325.0 (29,000); 425.0 (64,400); 710.5 (9,800); 767.5 (38,500); anal. Found: C, 42.42; H, 4.28; N, 10.34 (calcd for C$_{32}$H$_{34}$N$_5$Cl·NO$_3$·($\frac{1}{2}$H$_2$O): C, 57.19; H, 5.25; N, 12.50; calcd for C$_{32}$H$_{34}$N$_5$Cd·NO$_3$·BzIm·CHCl$_3$ C, 53.35; H, 4.59; N, 12.44; calcd for C$_{32}$H$_{34}$N$_5$Cd NO$_3$·CHCl$_3$ C, 41.26; H, 3.66; N, 8.25). The single crystal of 4b$_A$ used for the X-ray structure determination was isolated from residual noncrystalline material following a second recrystallization which involved layering a concentrated solution of the above crude material in CDCl$_3$ with n-hexane and letting stand for several months in the refrigerator.

Preparation of complex 5a$_A$·NO$_3$. In a fashion similar to that used to prepare the crude cadmium-containing complex described above, the sp$^3$ form of the ligand (1$_A$) was treated with cadmium nitrate tetrahydrate and purified on Sephadex. To a ca. 0.7 ml, 0.005 M sample of this product in CDCl$_3$, was added 25 $\mu$l of pyr-D$_5$. The resulting solution was layered with n-hexane, and placed in the refrigerator. After several months, green crystals were isolated in nearly quantitative yield. The molecular composition of these crystals was determined, on the basis of the single crystal X-ray diffraction analysis reported earlier, [11] to be 5a·NO$_3$·CHCl$_3$. $^1$H NMR (CDCl$_3$/pyr-D$_5$) $\delta = 1.55$–1.70 (12H, m, CH$_2$C$\underline{\text{H}}_3$], 3.22 (3H, s, CH$_3$), 3.45–3.56 (8H, m, C$\underline{\text{H}}_2$CH$_3$), 8.40 (2H, m, phen. CH), 9.32 (2H, s, CH=N), 9.75 (2H, m, phen. CH), 11.62 (2H, s, C$\underline{\text{H}}$=C); UV/VIS (CHCl$_3$-pyr v/v 10/1) $\lambda_{max}$ nm ($\epsilon$) 321.5 (45,000), 426.5 (79,000), 700.5 (13,500), 765.5 (51,900).

The $^1$H NMR titration of 3$_A$·NO$_3$ with BzIm or pyr-D$_5$ was done. Rigorously purified complex 3$_A$·NO$_3$ was dried at 80° C. under reduced pressure (1 mmHg) for 1 day. Starting samples for titration were then prepared by dissolving this five coordinate complex (3.32 mg, 0.005 mmol) in 0.7 to 0.75 ml of CDCl$_3$ and transferring quantitatively to an NMR tube. To such samples were then added increasing aliquots of either BzIm or pyr-D$_5$ (as solutions of known concentration in CDCl$_3$) and recording the chemical shift of the "meso" protons at 27° C. Control experiments were also carried out by adding known quantities of CF$_3$CO$_2$H, D$_2$O, and NH$_4$NO$_3$ to similar stock solutions of 3.NO$_3$. In these various $^1$H NMR titrations the absolute chemical shifts for any given base to ligand ratio were found to vary by less than 0.05 ppm between independent runs, with the values of $\delta - \delta_o$, the critical observable used for the K$_{eq.}$ determinations (see below), being found to vary even less (generally $\leq 0.003$ ppm).

Determination of Binding Constants. Inspection of FIGS. 14 and 15 shows that the binding of BzIm to cation 3$_A$ may be considered as two well-separated equilibrium processes. The chemical shift data obtained for the "meso" signals as a function of added BzIm were thus analyzed as such at both very low and very high conversion: Standard Scatchard (single reciprocal) plots[38] were constructed by plotting $(\delta - \delta_o)/[$BzIm$]$ vs $(\delta - \delta_o)$ according to equation 4 (which corresponds to eq. 5.13 of ref. 38), obtaining K as the absolute value of the slope and the term $(\delta_\infty - \delta_o)$K as the intercept.

$$(\delta - \delta_o)/[BzIm] = -K(\delta - \delta_o) + (\delta_\infty \delta_o)K \quad (4)$$

Here $\delta$ is the observed chemical shift, $\delta_o$ is the initial chemical shift of the pure five or six coordinate starting complex (3$_A$.NO$_3$ or 4b$_A$.NO$_3$), $\delta_\infty$ the chemical shift calculated for the final mono- or bisligated complexes 4b$_A$. NO$_3$ or 5a$_A$.NO$_3$, K the equilibrium constant in question, and [BzIm] the concentration of free, uncomplexed benzimidazole. In both the low and high conversion regimes, it proved necessary to correct for bound benzimidazole so as to obtain valid expressions for [BzIm] in terms of added benzimidazole ([BzIm]). This was done in a straightforward manner according to the expressions given in equations 5 and 6, where [lig]$_o$ represents the concentration of the starting five coordinate ligand 3$_A$.NO$_3$.

$$[BzIm] = [BzIm]_o - [lig]_o(\delta - \delta_o)/(\delta_\infty - \delta_o) \text{ at low } [BzIm]_o \quad (5)$$

$$[BzIm] \approx [BzIm]_o - [lig]_o \text{ at high } [BzIm]_o \quad (6)$$

Using these corrected values for [BzIm], straight line Scatchard plots were obtained with R$\geq$0.99 and 0.98 respectively for the low and high [BzIm]$_o$ regimes giving values of K$_1$ and K$_2$ of $1.80 \times 10^4$ M$^{-1}$ and 12.9 M$^{-1}$ respectively (see supplementary material). The value for K$_1$ is considered to be quite reliable (estimated error $\leq 15\%$); the low solubility of BzIm and the resulting incomplete nature of the titration associated with the formation of 5a$_A$.NO$_3$, however, makes the value obtained for K$_2$ somewhat more approximate (estimated error $\leq 25\%$).[49]

Figure 16:
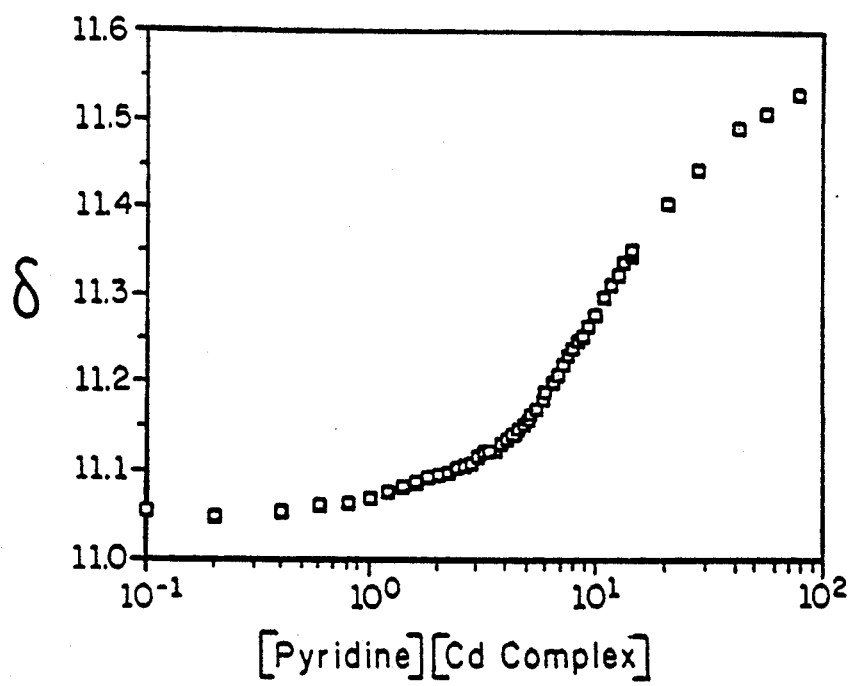
FIG. 16 shows changes in the $^1H$ NMR chemical shift of the "meso" signal for $3_A.NO_3$ as a function of increasing [pyr]. The terms [pyr] and [ligand] represent the total molar concentration of added benzimidazole and starting five-coordinate complex $3_A.NO_3$.
Figure 15A:
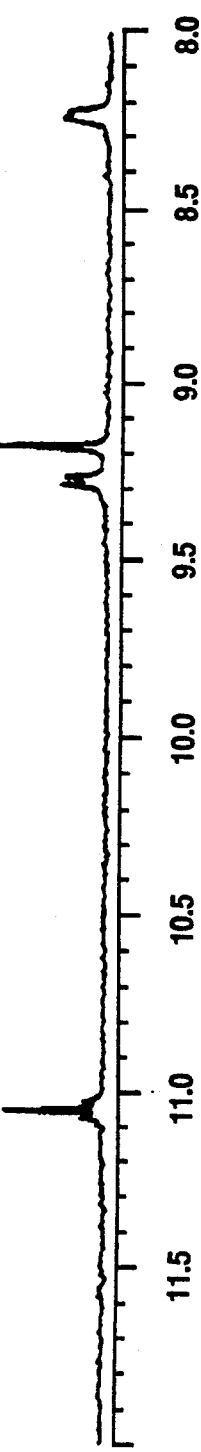
FIG. 15 shows $^1H$ NMR spectral titration of $3_A.NO_3$ (initially $6.66 \times 10^{-3}$ M in $CDCl_3$) with increasing quantities of pyridine showing changes occurring in high field region. The [pyr]/[ligand] ratios are 0, 5, 10, 14, 20, and 40 for traces A through F respectively. The terms [pyr] and [ligand] represent the total molar concentration of added benzimidazole and starting five-coordinate complex.
Figure 15B:
Figure 15C:
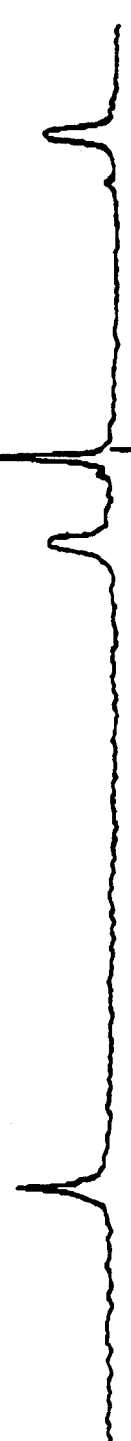
Figure 15D:
Figure 15E:
Figure 15F:
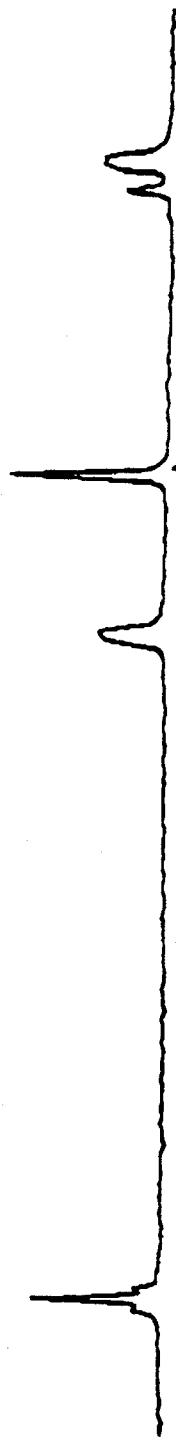

The changes in "meso" proton chemical shift as a function of added [pyr] shown in FIG. 16 indicate a clear absence of two distinct binding regimes. Moreover, as expected, attempts to fit the data as a simple monoligation process (to give 6CN material) according to eq. 1 did not work. It therefore proved necessary to analyze the data in terms of two concurrent equilibrium processes. This was done using the convenient iterative procedure outlined by Connors.[38] Here the equations of interest, corresponding to eqs. 4.31 and 4.32 of Connors,[38] as adopted for NMR analyses, are:

$$1/[pyr] - K_1\Delta_{11}/(\delta - \delta_o) = K_1K_2[pyr]\{\Delta_{12}/(\delta - \delta_o) - 1\} - K_1 \quad (7)$$

$$(\delta - \delta_o)\{1 + K_1[pyr] + K_1K_2[pyr]^2\}/[pyr] = K_1K_2\Delta_{12}[pyr] + K_1\Delta_{11} \quad (8)$$

where $\delta$ is the observed chemical shift, $\delta_o$ is the initial chemical shift of the pure five coordinate starting complex 3.NO$_3$, $\Delta_{11}$ is the total chemical shift difference corresponding to the formation of the pure putative monoligated six coordinate species, $\Delta_{12}$ is the total chemical shift corresponding to the formation of the bisligated cationic species 5a from the initial five coordinate material, and [pyr] is the free pyridine concentration. A precise expression for [pyr] is given by equation 9,[38] where [pyr]$_o$ is the concentration total added pyridine, and [lig]$_o$ represents the concentration of the starting five coordinate ligand 3$_A$.NO$_3$:

$$[pyr]_o = [pyr] + [lig]_o(K_1[pyr] + 2K_1K_2$$
$$[pyr]^2)/(1 + K_1[pyr] + K_1K_2[pyr]^2) \qquad (9)$$

Inspection of the binding isotherm (FIG. 16), however, suggested that the approximation $[pyr] \approx [pyr]_o$ would be reasonably valid over much of the titration range. Initial iterative solutions of eqs. 7 (plotting $1/[pyr] - K_1\Delta_{11}/(\delta - \delta_o)$ vs. $[pyr]\{\Delta_{12}/(\delta - \delta_o) - 1\}$, giving $K_1K_2$ and $-K_1$ as the slope and intercept respectively) and 8 (plotting $(\delta - \delta_o) \{1 + K_1[pyr] + K_1K_2[pyr]^2\}/[pyr]$ vs. [pyr], giving $K_1K_2\Delta_{12}$ and $K_1\Delta_{11}$ as the slope and intercept respectively) were therefore made using this greatly simplifying assumption. They converged quickly to give initial, uncorrected values of $K_1 \approx 1.5$ M$^{-1}$ and $K_1K_2 = 308$ M$^{-2}$. These values confirmed that under the conditions of the experiment (where $[3_4.NO_3] \approx 0.005$ M), the approximation $[pyr] \approx [pyr]_o$ is valid to within $\leq 4\%$ in the regime of greatest interest, namely $3 < [pyridine]/[ligand] < 10$ and 0.005 M in $3_4.NO_3$. When corrections are made for this small percentage, final values of $K_1$ of $\approx 1.6$ M$^{-1}$ and $K_1K_2 = 315$ M$^{-2}$ are obtained (see supplementary material). We consider it important to stress that although the value of $K_1K_2$ is well determined (estimated error $\leq 10\%$), the nature of the data does not allow $K_1$ (and hence $K_2$) to be defined with precision (estimated error $\approx 50\%$). This uncertainty, however, does not detract from the central conclusions described herein.

X-ray Experimental for complex $4b_4$. For $4b_4.NO_3.CHCl_3$: $C_{40}H_{41}N_8O_3Cl_3Cd$, M = 900.57. The data crystal was a very dark green plate of dimensions 0.06 × 0.22 × 0.44 mm, which was grown by slow diffusion from CHCl$_3$-hexanes and separated from the accompanying noncrystalline material as described above. The data were collected on a Nicolet R3 diffractometer, with a graphite monochromator, using Mo K$\alpha$ radiation ($\lambda = 0.71069$ Å) and a Nicolet LT-2 low-temperature delivery system (163° K.). Lattice parameters were obtained from least-squares refinement of 26 reflections with $19.2° < 2\theta < 24.4°$. The space group was triclinic, P1 (No. 2), with Z = 2, F(000) = 920, a = 11.276(4), b = 12.845(3), c = 14.913(4) Å, $\alpha = 84.82(2)$, $\beta = 69.57(2)$, $\lambda = 85.84(2)°$, v = 2014(1) Å, $\rho_c = 1.48$ g-cm$^{-3}$. Data were collected using the omega scan technique (7191 reflections, 6566 unique, R$_{int}$ = 0.064), 2$\theta$ range 4.0 -50.0°, 1.2° $\omega$ scan at 3°-6°/min. (h = 0 14, k = −15, l = −18→18). Four reflections (−2,2,0; 3,2,3; 2, −3, −1; −1,0,−4) were remeasured every 146 reflections to monitor instrument and crystal stability. Decay correction range on I was 0.9863-1.076. Data also corrected for L$_p$ effects and absorption (based on crystal shape; transmission factor range 0.8533 −0.9557, $\mu = 7.867$ cm$^{-1}$). Reflections having $F_o < 6\rho$ ($F_o$) considered unobserved (3272 reflections). The structure was solved by heavy atom and Fourier methods and refined by full-matrix least-squares procedures in blocks of 253 and 287 with anisotropic thermal parameters for the non-H atoms (except O3A of the disordered NO$_3$− group and the terminal C atoms of the disordered ethyl groups of one pyrrole ring, C29 [site occupancy factor 0.44(2)], C29A, C31 [site occupancy factor 0.37(2)] and C31A). Nitrate disordered about two orientations of the N atom (N1B) with site occupancy factors for the minor orientation (0 atoms labeled with A) of 0.45(2). H atoms were calculated and refined with isotropic thermal parameters riding on the relevant C atom. CHCL$_3$ solvent is disordered by rotation about a C - Cl bonding axis (ClC - Cl1) with site occupancy factor for the minor component (Cl atoms labelled with A) of 0.43(2). Due to the disorder, the chloroform H atom position was not calculated. $\Sigma w(|F_o| - |F_c|)^2$ minimized, where $w = 1/[(\rho(F_o))^2 + 0.0118(F^2)]$ and $\rho(F_o) = 0.5kI^{-\frac{1}{2}}(\rho(I))$. Intensity, I, given by ($^I$peak − $^I$background)x(scan rate) and k is the correction due to Lp effects, absorption and decay. Sigma(I) estimated from counting statistics; $\rho(I) = [(^I\text{peak} + ^I\text{background})^{\frac{1}{2}}x(\text{scan rate})]$ Final R = 0.0781 for 3294 reflections, wR = 0.114 (R$_{all}$ = 0.143, wR$_{all}$ = 0.176) and a goodness of fit = 1.00. Maximum $|\Delta/\rho| < 0.1$ in the final refinement cycle and the minimum and maximum peaks in the final $\Delta F$ map were −0.97 and 1.69 e−/Å$^3$, respectively (in the region of the Cd atom). Data reduction, structure solution and initial refinement were accomplished using Nicolet's SHELXTL-PLUS[50] software package. The final refinement was done using SHELX76.[51] Neutral atom scattering factors for the non-H atoms from Cromer and Mann,[52] with anomalous-dispersion corrections from Cromer and Liberman,[53] while scattering factors for the H atoms from Stewart, Davidson and Simpson;[54] linear absorption coefficient from the International Tables for X-ray Crystallography (1974).[55] The least-squares planes program was supplied by Cordes;[56] other computer programs from reference 11 of Gadol and Davis.[57]

Table 1 shows sectional coordinate or equivalent isotropic thermal parameters (Å$^2$) for non-hydrogen atoms of $4b_4$.CHCl$_3$ Table 2 shows bond lengths (Å) and angles (°) for non-hydrogen atoms of cation $4b_4$.

TABLE 1. Fractional coordinates and isotropic or equivalent isotropic$^a$ thermal parameters (Å$^2$) for non-hydrogen atoms of $4b_4$.NO$_3$.CHCl$_3$.

| Atom | x | y | z | U |
|---|---|---|---|---|
| Cd | .37392(8) | .12411(6) | .04542(7) | .0573(4) |
| N1 | .5259(9) | .1813(7) | .1140(9) | .065(5) |
| C2 | .5321(13) | .1503(10) | .2032(11) | .062(6) |
| C3 | .6213(12) | .2115(11) | .2219(10) | .064(6) |
| C4 | .6661(11) | .2783(9) | .1439(11) | .061(6) |
| C5 | .6066(12) | .2575(9) | .0765(11) | .060(6) |
| C6 | .6340(12) | .3124(9) | −.0106(12) | .065(7) |
| C7 | .5828(11) | .3039(8) | −.0848(11) | .063(6) |
| N8 | .4929(9) | .2314(7) | −.0754(8) | .056(4) |
| C9 | .4750(12) | .2437(10) | −.1581(11) | .070(6) |
| C10 | .5492(14) | .3233(11) | −.2225(10) | .075(6) |
| C11 | .6178(12) | .3604(9) | −.1782(11) | .069(6) |
| C12 | .3827(14) | .1784(12) | −.1763(10) | .073(6) |
| N13 | .3236(10) | .1169(8) | −.1068(8) | .057(4) |
| C14 | .2359(11) | .0438(11) | −.1074(10) | .063(6) |
| C15 | .1851(13) | .0468(12) | −.1834(10) | .072(6) |
| C16 | .1028(14) | −.0250(12) | −.1825(10) | .067(6) |
| C17 | .0648(13) | −.0982(12) | −.1067(11) | .071(7) |
| C18 | .1077(12) | −.1040(9) | −.0331(11) | .074(7) |
| C19 | .1952(12) | −.0304(8) | −.0304(11) | .064(6) |
| N20 | .2428(10) | −.0258(9) | .0420(9) | .065(5) |
| C21 | .2112(13) | −.0873(9) | .1201(11) | .065(6) |
| C22 | .2643(12) | −.0711(9) | .1918(11) | .065(7) |
| N23 | .3510(10) | .0013(6) | .1716(9) | .061(5) |
| C24 | .3782(14) | .0029(10) | .2535(13) | .076(7) |
| C25 | .3076(14) | −.0727(10) | .3260(12) | .080(7) |
| C26 | .2349(15) | −.1183(9) | .2854(11) | .073(7) |
| C27 | .4669(13) | .0715(10) | .2649(11) | .067(6) |
| C28 | .6508(14) | .2018(13) | .3139(11) | .084(7) |
| C29 | .553(5) | .234(4) | .400(3) | .105(15) |
| C29A | .590(2) | .282(2) | .381(2) | .082(8) |
| C30 | .765(2) | .3611(12) | .1304(13) | .088(8) |
| C31A | .710(3) | .450(2) | .194(2) | .101(9) |
| C31 | .704(3) | .475(2) | .134(2) | .040(7) |
| C32 | .7108(13) | .4478(10) | −.2122(11) | .072(6) |
| C33 | .6487(14) | .5579(11) | −.1933(13) | .088(8) |
| C34 | .553(2) | .3512(14) | −.3236(10) | .096(8) |
| C35 | .132(2) | −.1983(11) | .3305(13) | .093(8) |
| C36 | .305(2) | −.0887(12) | .4286(11) | .084(8) |
| C37 | .229(2) | −.007(2) | .4904(14) | .125(11) |

-continued

| Atom | x | y | z | U$^a$ |
|---|---|---|---|---|
| N1A | .2036(10) | .2375(6) | .1132(8) | .059(5) |
| C2A | .1817(13) | .3278(11) | .060(2) | .095(9) |
| N3A | .0853(13) | .3834(8) | .1207(14) | .101(8) |
| C4A | .0536(12) | .3373(11) | .2074(14) | .073(7) |
| C5A | −.043(2) | .3615(13) | .300(2) | .103(11) |
| C6A | −.056(2) | .296(2) | .378(2) | .116(12) |
| C7A | .0178(15) | .1969(15) | .3762(10) | .089(7) |
| C8A | .1056(14) | .1750(12) | .2886(11) | .070(7) |
| C9A | .1212(11) | .2418(9) | .2079(10) | .053(5) |
| C11 | .3144(6) | .5520(4) | .5507(4) | .129(3) |
| C12 | .3058(12) | .2261(8) | .5862(6) | .118(5) |
| C13 | .1613(13) | .3391(13) | .4877(8) | .165(8) |
| C12A | .056(2) | .4327(14) | .5339(13) | .155(10) |
| C13A | .2064(15) | .2450(12) | .5529(14) | .157(9) |
| C1C | .198(3) | .357(2) | .5834(15) | .152(15) |
| N1B | .9690(14) | .6403(9) | .1553(10) | .073(6) |
| O1 | .985(3) | .588(2) | .079(2) | .072(11) |
| O2 | .943(4) | .734(2) | .167(2) | .17(2) |
| O3 | 958(3) | .587(2) | .233(2) | .123(14) |
| O1A | .853(3) | .660(4) | .199(3) | .19(2) |
| O2A | 1.043(3) | .598(3) | .089(3) | .065(13) |
| O3A | 1.030(5) | .676(4) | .173(3) | .16(2) |

$^a$For anisotropic atoms, the U value is $U_{eq}$, calculated as $U_{eq} = \frac{1}{3}\Sigma_i\Sigma_j U_{ij} a_i{}^* a_j{}^* A_{ij}$ where $A_{ij}$ is the dot product of the $i^{th}$ and $j^{th}$ direct space unit cell vectors.

TABLE 2

Bond Lengths (Å) and Angles (°) for non-H atoms of cation 4b$_A$.

| 1 | 2 | 3 | 1-2 | 1-2-3 |
|---|---|---|---|---|
| C2 | N1 | C5 | 1.38(2) | 107.2(13) |
| C5 | N1 | | 1.33(2) | |
| C3 | C2 | C27 | 1.43(2) | 124.(2) |
| C3 | C2 | N1 | | 109.5(11) |
| C27 | C2 | N1 | 1.37(2) | 126.3(15) |
| C4 | C3 | C28 | 1.35(2) | 129.3(14) |
| C4 | C3 | C2 | | 105.9(14) |
| C28 | C3 | C2 | 1.51(2) | 124.7(12) |
| C5 | C4 | C30 | 1.44(3) | 126.9(13) |
| C5 | C4 | C3 | | 107.8(12) |
| C30 | C4 | C3 | 1.55(2) | 125.(2) |
| C6 | C5 | N1 | 1.37(2) | 129.(2) |
| C6 | C5 | C4 | | 121.7(12) |
| N1 | C5 | C4 | | 109.5(13) |
| C7 | C6 | C5 | 1.43(3) | 129.2(12) |
| N8 | C7 | C11 | 1.39(2) | 110.7(14) |
| N8 | C7 | C6 | | 121.3(12) |
| C11 | C7 | C6 | 1.45(2) | 127.8(12) |
| C9 | N8 | C7 | 1.31(2) | 103.3(11) |
| C10 | C9 | C12 | 1.43(2) | 127.(2) |
| C10 | C9 | N8 | | 113.6(14) |
| C12 | C9 | N8 | 1.49(2) | 119.7(11) |
| C11 | C10 | C34 | 1.32(2) | 127.8(13) |
| C11 | C10 | C9 | | 106.7(14) |
| C34 | C10 | C9 | 1.51(2) | 125.(2) |
| C32 | C11 | C7 | 1.52(2) | 125.(2) |
| C32 | C11 | C10 | | 129.1(15) |
| C7 | C11 | C10 | | 105.7(11) |
| N13 | C12 | C9 | 1.26(2) | 115.2(15) |
| C14 | N13 | C12 | 1.41(2) | 126.1(14) |
| C15 | C14 | C19 | 1.43(2) | 119.5(13) |
| C15 | C14 | N13 | | 121.7(12) |
| C19 | C14 | N13 | 1.39(2) | 118.7(14) |
| C16 | C15 | C14 | 1.25(2) | 120.2(13) |
| C17 | C16 | C15 | 1.37(2) | 119.(2) |
| C18 | C17 | C16 | 1.34(3) | 123.(2) |
| C19 | C18 | C17 | 1.43(2) | 120.0(13) |
| N20 | C19 | C14 | 1.37(2) | 116.6(12) |
| N20 | C19 | C18 | | 125.7(12) |
| C14 | C19 | C18 | | 118.(2) |
| C21 | N20 | C19 | 1.30(2) | 124.2(13) |
| C22 | C21 | N20 | 1.43(3) | 118.3(13) |
| N23 | C22 | C26 | 1.34(2) | 113.(2) |
| N23 | C22 | C21 | | 118.0(13) |
| C26 | C22 | C21 | 1.41(2) | 129.1(12) |
| C24 | N23 | C22 | 1.36(2) | 104.7(12) |
| C25 | C24 | C27 | 1.44(2) | 125.(2) |
| C25 | C24 | N23 | | 111.1(14) |
| C27 | C24 | N23 | 1.44(2) | 123.9(12) |

TABLE 2-continued

Bond Lengths (Å) and Angles (°) for non-H atoms of cation 4b$_A$.

| 1 | 2 | 3 | 1-2 | 1-2-3 |
|---|---|---|---|---|
| C26 | C25 | C36 | 1.37(3) | 127.9(13) |
| C26 | C25 | C24 | | 105.(2) |
| C36 | C25 | C24 | 1.52(3) | 127.(2) |
| C35 | C26 | C22 | 1.54(2) | 124.(2) |
| C35 | C26 | C25 | | 129.(2) |
| C22 | C26 | C25 | | 106.3(12) |
| C2 | C27 | C24 | | 130.(2) |
| C29 | C28 | C3 | 1.44(4) | 118.(3) |
| C29A | C28 | C3 | 1.46(3) | 115.(2) |
| C31A | C30 | C4 | 1.51(3) | 112.(2) |
| C31 | C30 | C4 | 1.57(3) | 111.(2) |
| C33 | C32 | C11 | 1.54(2) | 114.0(11) |
| C37 | C36 | C25 | 1.47(2) | 114.(2) |
| C9A | N1A | C2A | 1.40(2) | 108.5(10) |
| C2A | N1A | . | 1.40(2) | |
| N3A | C2A | N1A | 1.35(2) | 107.(2) |
| C4A | N3A | C2A | 1.31(3) | 109.4(14) |
| C5A | C4A | C9A | 1.47(3) | 115.(2) |
| C5A | C4A | N3A | | 133.3(14) |
| C9A | C4A | N3A | 1.40(2) | 111.2(13) |
| C6A | C5A | C4A | 1.34(3) | 120.(2) |
| C7A | C6A | C5A | 1.47(3) | 124.(2) |
| C8A | C7A | C6A | 1.37(2) | 115.(2) |
| C9A | C8A | C7A | 1.38(2) | 121.7(14) |
| N1A | C9A | C4A | | 103.7(12) |
| N1A | C9A | C8A | | 132.1(11) |
| C4A | C9A | C8A | | 124.1(13) |

The characterization by x-ray diffraction analysis of a six coordinate pentagonal pyramidal cadmium(II) cationic complex 4b$_A$ derived from a novel aromatic 22 $\pi$-electron pentadentate "expanded porphyrin" ligand (2$_A$) is described. The X-ray structure reveals the five central donor atoms of the macrocycle to be coordinated to the cadmium(II) cation which in turn lies 0.334(2) Å above the mean plane of the macrocycle and is further ligated by an apical benzimidazole ligand. As is true in the corresponding pentagonal bipyramidal bispyridine adduct 5a$_A$, the X-ray structure of cation 4b$_A$ indicates the macrocyclic ligand to be nearly planar (maximum deviation, 0.154(13) Å for C15) with the five donor nitrogen atoms defining a near circular cavity with a center-to-nitrogen radius of ≅2.42 Å. The crystals of 4b$_A$·NO$_3$ used for the X-ray diffraction analysis were isolated from an inhomogeneous mixture of crystalline and noncrystalline material obtained following treatment of the sp$^3$ form of the ligand (1$_A$) with Cd(NO$_3$)$_2$·(H$_2$O)$_4$ and subsequent purification on sephadex. The proton NMR spectrum in CDCl$_3$ of this bulk material is essentially identical to that of the pure five coordinate complex 3$_A$ prepared independently, but showed the presence of a broad feature at ca. 6.4 ppm and two sharper peaks at 6.81 and 7.27 ppm ascribable to the bound benzimidazole ligand. These diagnostic ligand features are reproduced upon titrating the pure five coordinate complex 3$_A$ with roughly 3/5 equivalent of benzimidazole. This finding suggests that the bulk material from which crystals of 4b$_A$·NO$_3$ were isolated consists of a mixture of crystalline and noncrystalline six and five coordinate species and supports the hypothesis that the bound benzimidazole found in cation 4b$_A$ is derived from degradative side reactions associated with the metal insertion and accompanying ligand oxidation. From these titrations the values for the sequential formation constants (K$_1$ and K$_2$) for the binding of the first and second equivalents of benzimidazole to the five coordinate cationic complex 3$_A$ were determined to be 1.8×10$^4$ M-1 respectively. For the complexation of pyridine to $3_A \cdot NO_3$, $K_1 \cdot K_2$ values of 1.6 $M^{-1}$ and 315 $M^{-2}$ respectively were determined from similar $^1H$ NMR titrations. These results indicate that in benzimidazole-containing chloroform solutions an extended concentration range exists wherein the pentagonal pyramidal complex $4b_A$ is the primary cadmium containing species, whereas in the presence of pyridine it is either the unligated complex $3_A$ or the coordinatively saturated pentagonal bipyramidal species $5a_A$ which will dominate in solution.

Published literature references in the following list are incorporated by reference herein for the reasons cited.

REFERENCES

1. "The Porphyrins"; Dolphin, D., Ed.; Academic Press: New York, 1978-1979; Vols. I-VII.
2. (a) Day, V. W.; Marks, T. J.; Wachter, W. A. J. Am. Chem. Soc. 1975, 97, 4519-4527. (b) Marks, T. J.; Stojakovic, D. R. J. Am. Chem. Soc. 1978, 100, 1695-1705. (c) Cuellar, E. A.; Marks, T. J. Inorg. Chem. 1981, 20, 3766-3770.
3. Bauer, V. J.; Clive, D. R.; Dolphin, D.; Paine, J. B. III; Harris, F. L.; King, M. M.; Loder, J.; Wang, S.-W. C.; Woodward, R. B. J. Am. Chem. Soc. 1983, 105, 6429-6436. To date only tetracoordinated metal complexes have been prepared from these potentially pentadentate ligands.
4. Broadhurst, M. J.; Grigg, R.; Johnson, A. W. J. Chem. Soc. Perkin Trans. 1, 1972, 2111-2116.
5. (a) Broadhurst, M. J.; Grigg, R.; Johnson, A. W. J. Chem. Soc., Chem. Commun. 1969, 23-24; Broadhurst, M. J.; Grigg, R.; Johnson, A. W. J. Chem. Soc., Chem. Commun. 1969, 1480-1482; Broadhurst, M. J.; Grigg, R.; Johnson, A. W. J. Chem. Soc., Chem. Commun. 1970, 807-809.
6. (a) Berger, R. A.; LeGoff, E. Tetrahedron Lett. 1978, 4225-4228. (b) LeGoff, E.; Weaver, O. G. J. Org. Chem. 1987, 710-711.
7. (a) Rexhausen, H.; Gossauer, A. J. Chem. Soc., Chem. Commun. 1983, 275. (b) Gossauer, A. Bull. Soc. Chim. Belg. 1983, 92, 793-795.
8. Gosmann, M.; Franck, B. Angew. Chem. 1986, 98, 1107-1108; Angew. Chem. Int. Ed. Eng. 1986, 25, 1100-1101.
9. For examples of a porphyrin-like systems with smaller central cavities see: (a) Vogel, E.; Kocher, M.; Schmickler, H.; Lex, J. Angew. Chem. 1986, 98, 262-263; Angew. Chem. Int. Ed. Eng. 1986, 25, 257-258. (b) Vogel, E.; Balci, M.; Pramod, K.; Koch, P.; Lex. J. Ermer, O. Angew. Chem. 1987, 99, 909-912; Angew. Chem. Int. Ed. Eng. 1987, 26, 928-931.
10. For examples of large nonaromatic pyrrole-containing macrocycles see: (a) Acholla, F. V.; Mertes, K. B. Tetrahedron Lett. 1984, 3269-3270. (b) Acholla, F. V.; Takusagawa, F.; Mertes, K. B. J. Am. Chem. Soc. 1985, 6902-6908. (c) Adams, H.; Bailey, N. A.; Fenton, D. A.; Moss, S.; Rodriguez de Barbarin, C. O.; Jones, G. J. Chem. Soc., Dalton Trans. 1986, 693-699. (d) Fenton, D. E.; Moody, R. J. Chem. Soc., Dalton Trans. 1987, 219-220.
11. Sessler, J. L.; Murai, T.; Lynch, V.; Cyr, M. J. Am. Chem. Soc. 1988, 110, 5586-5588.
12. Sessler, J. L.; Cyr, M.; Murai, T. Comm. Inorg. Chem., in press.
13. Stark, W. M.; Baker, M. G.; Raithby, P. R.; Leeper, F. J.; Battersby, A. R. J. Chem. Soc., Chem. Commun. 1985, 1294.
14. Sessler, J. L.; Johnson, M. R.; Lynch, V. J. Org. Chem. 1987, 52, 4394-4397.
15. Sessler, J. L.; Johnson, M. R.; Lynch, V.; Murai, T. J. Coord. Chem., in press.
16. Sessler, J. L.; Murai, T. Tetrahedron Lett., to be submitted.
17. Hoard, J. L. In Porphyrins & Metalloporphyrins; Chapter 8, Smith, K., Ecl.; Elsevien, Amsterdam, 1975.
18. Chemical & Engineering News August 8, 1988, 26-27.
19. For reviews see: (a) Drew, M. G. B. Prog. Inorg. Chem. 1977, 23, 67-210. (b) Melson, G. A. in "Coordination Chemistry of Macrocyclic Compounds", Melson, G. A., Ed.; Plenum: New York, 1979, Chapter 1. (c) N. F. Curtis, in "Coordination Chemistry of Macrocyclic Compounds", Melson, G. A., Ed.; Plenum: New York, 1979, Chapter 4. (d) Nelson, S. M. Pure and Appl. Chem. 1980, 52, 2461-2476. (e) Lindoy, L. F. in "Synthesis of Macrocycles", Izatt, R. M. and Christensen, J. J., Eds.; J. Wiley: New York, 1987, Chapter 2. (f) Newkome, G. R.; Gupta, V. K.; Sauer, J. D. in "Heterocyclic Chemistry", Newkome, G. R., Ed.; J. Wiley: New York, 1984, Vol. 14, Chapter 3. (g) De Sousa, M.; Rest, A. J. Adv. Inorg. Chem. Radiochem. 1978, 21, 1-40. (h) See also ref. 12.
20. For recent examples of bipyridine-derived systems and related pentadentate ligands, see: (a) Ansell, C. W. G.; Lewis, J.; Raithby, P. R.; Ramsden, J. N.; Schroder, M. J. Chem. Soc., Chem. Commun., 1982, 546-547. (b) Lewis, J.; O'Donoghue, T. D.; Raithby, P. R. J. Chem. Soc., Dalton Trans., 1980, 1383-1389. (c) Constable, E. C.; Chung, L.-Y.; Lewis, J.; Raithby, P. R. J. Chem. Soc., Chem. Commun., 1986, 1719-1720. (d) Constable, E. C.; Holmes, J. M.; McQueen, R. C. S. J. Chem. Soc., Dalton Trans., 1987, 5-8.
21. Ochai, E.-I. "Bioinorganic Chemistry", Allyn and Bacon: Boston, 1977, pp. 475-476.
22. Klaasen, C. D. in "The Pharmacological Basis of Therapeutics, 6th Edition", Gilman, A. G.; Goodman, L. S.; Gilman, A., Eds., Macmillan: New York, 1980 Chapter 69, pp. 1632-1633.
23. For recent reviews see: (a) Summers, M. F. Coord. Chem. Rev. 1988, 86, 43-134. (b) Ellis, P. D. Science 1983, 221, 1141-1146. (c) Ellis, P. D. in "The Multinuclear Approach to NMR Spectroscopy", Lambert, J. B.; Riddell, F. G., Eds.; D. Reidel: Amsterdam, 1983, pp. 457-523.
24. Interestingly, pentagonal pyramidal and pentagonal bipyramidal geometries have been observed in two very closely related pentadentate macrocyclic Schiff base ligands which differ only in the size of the ring (16 vs. 17 atoms); see: (a) Nelson, S. M.; McFall, S. G.; Drew, M. G. B.; Othman, A. H. J. Chem. Soc., Chem. Commun. 1977, 167-168, and (b) Drew, M. G. B.; McFall, S. G.; Nelson, S. M. J. Chem. Soc., Dalton Trans. 1977, 575-581.
25. OEP = octaethylporphyrin, TPP = tetraphenylporphyrin, and PPIXDME = protoporphyrin IX dimethyl ester, with the prefixes $H_2$ and Cd referring to the free-base and cadmium(II) forms respectively; BzIm = benzimidazole; pyr = pyridine.
26. Rodesiler, P. F.; Griffith, E. H.; Ellis, P. D.; Amma, E. L. J. Chem. Soc., Chem. Commun., 1980, 492-493.
27. Hazell, A. Acta Cryst. 1986, C42, 296-299.
28. "Texaphyrin" 2 and its derivatives can be formulated as either a benzannelated [18]annulene as an overall 22 $\pi$-electron aromatic system. On the basis of preliminary molecular orbital calculations, and spectral comparisons to an 18 $\pi$-electron macrocyclic analogue of 3.NO$_3$ derived from diaminomalionitrile, for which a lowest energy Q-type transition of 692 nm is observed, we currently favor the 22 $\pi$-electron formulation: Hemmi, G.; Krull, K., Cyr, M., Sessler, J. L., unpublished results.

29. Drago, R. S. "Physical Methods in Chemistry", W. B. Saunders: Philadelphia, 1977, Chapter 5.

30. Miller, J. R.; Dorough, G. D. J. Am. Chem. Soc. 1952, 74, 3977-3981.

31. Kirksey, C. H.; Hambright, P. Inorg. Chem. 1970, 9, 958-960.

32. For general discussions see: Gouterman, M. In ref. 1, Vol. III, Chapter 1.

33. Dorough, G. D.; Miller, J. R. J. Am. Chem. Soc. 1951, 73, 4315-4320.

34. Edwards, L.; Dolphin, D. H.; Gouterman, M.; Adler, A. D. J. Mol. Spectroscopy, 1971, 38, 16-32.

35. Johnson, M. R.; Cyr, M.; Sessler, J. L., unpublished results.

36. (a) Scheer, H.; Katz, J. J. In ref. 17, Chapter 10. (b) Janson, T. R.; Katz, J. J. In ref. 1, Vol IV, Chapter 1.

37. "Aldrich Library of NMR Spectroscopy, 2nd ed.", Pouchert, C. J., Ed., Aldrich Chemical Co.: Milwaukee, 1983; Vol. 2, p. 558.

38. Connors, K. A. "Binding Constants", J. Wiley: New York, 1987.

39. We ascribe much of this stability to kinetic factors: As detailed herein, insertion of $Cd^{2+}$ into the preformed "texaphyrin" 2 did not take place at an appreciable rate. This suggests that the kinetic barrier is substantial for metal insertion; the same is likely to be true for decomplexation.

40. The addition of traces of acid causes the "meso" signals to shift dramatically to higher field, moving, for instance, by 0.113 ppm after the addition of 1 equivalent of $CF_3CO_2H$; this suggests that the quantitative $K_{eq}$ titration experiments are in fact reflecting base binding to cadmium and not simple deprotonation of an adventitiously protonated metal complex.

41. For general discussions see: (a) Ellis, P. E., Jr.; Linard, J. E.; Szymanski, T.; Jones, R. D.; Budge, J. R.; Basolo, F. J. Am. Chem. Soc. 1980, 102, 1889-1896. (b) Brault, D.; Rougeee, M. Biochemistry, 1975, 13, 4591-4597. (c) Collman, J. P.; Brauman, J. I.; Doxsee, K. M.; Halbert, T. R.; Bunnenberg, E.; Linder, R. E.; LaMar, G. N.; Del Gaudio, J.; Lang, G.; Spartalian, K. J. Am. Chem. Soc. 1980, 102, 4182-4192. (d) Traylor, T. G. Acc. Chem. Res. 1981, 14, 102-109.

42. (a) Collman, J. P.; Brauman, J. I.; Doxsee, K. M.; Sessler, J. L.; Morris, R. M.; Gibson, Q. H. Inorg. Chem. 1983, 22, 1427-1432.

43. See for instance: (a) Collman, J. P.; Reed, C. A. J. Am. Chem. Soc. 1973, 95, 2048-2049. (b) Wagner, G. C.; Kassner, R. J. Biochim. Biophys. Acta 1975, 392, 319-327. (c) See also refs. 41b-41d.

44. Preliminary photochemical studies indicate that following photoexcitation at 350 nm, the excited triplet of cation 3 is formed in roughly 80% quantum yield. In the absence of oxygen, the observed triplet lifetime is 54 $\mu$s; in the presence of air, the triplet state is quenched completely by formation of singlet oxygen: Mallouk, T.; Sessler, J. L., unpublished results.

45. This material has been further characterized by preliminary $^{113}Cd$ NMR studies in the solid state (Kennedy, M. A.; Ellis, P. D.; Murai, T.; Sessler, J. L., unpublished results). The isotropic chemical shift of this complex (3.NO$_3$)$\sigma$=191 ppm relative to solid cadmium perchlorate, is shielded by ≈200-300 ppm relative to "normal" cadmium porphyrins such as CdTPP[25] ($\sigma$=399 ppm[46]) or CdPPIXDME[25] (($\sigma$=480 ppm[47]). This difference may reflect the increased shielding caused by the presence of an additional pair of electrons within the binding core of the "expanded" "texaphyrin" ligand. A simulation of magic angle spinning spectra, using the theory of Maricq and Waugh,[48] yields an anisotropy of $\Delta\sigma$=207.6 and asymmetry, $\eta$=0.01, indicative of a system with a $\geq$3-fold axis of symmetry. In addition, the eigenvalues of the chemical shift tensor were found to be $\sigma_{11}$=120.6 ppm, $\sigma_{22}$=123 ppm, and $\sigma_{33}$=329.6 ppm.

46. Jakobsen, H. J. J. Am. Chem. Soc. 1982, 104, 7442-7542.

47. Kennedy, M. A.; Ellis, P. D., submitted to J. Biol. Chem.

48. Maricq, M.; Waugh, J. S. J. Chem. Phys. 1979, 70, 3300-3316.

49. This data could also be analyzed using the iterative approach used for pyridine complexation. Values of $K_1$ and $K_1K_2$ of $2.0 \times 10^4$ M$^{-1}$ and $1.9 \times 10^5$ M$^{-2}$ were obtained using this approach.

50. SHELXTL-PLUS. Nicolet Instrument Corporation, Madison, Wis., USA: 1987.

51. SHELX76. A program for crystal structure determination. Sheldrick, G. M.; Univ. of Cambridge, England: 1976.

52. Cromer, D. T.; Mann, J. B. Acta Cryst. 1968, A24, 321-324.

53. Cromer, D. T.; Liberman, D. J. Chem. Phys. 1970, 53, 1891-1898.

54. Stewart, R. F., Davidson, E. R.; Simpson, W. T. J. Phys. Chem. 1965, 42, 3175-3187.

55. International Tables for X-ray Crystallography, 1974, Vol. IV, p 55, Birmingham: Kynoch Press: 1974.

56. Cordes, A. W., personal communication (1983).

57. Gadol, S. M.; Davis, R. E. Organometallics 1982, 1, 1607-1613.

EXAMPLE 3

Gadolinium(III) complexes derived from strongly binding anionic ligands, such as diethylenetriamine pentaacetic acid (DTPA),[1,2,3] 1,4,7,10-tetraazacyclododecane N,N',N,",N'''-tetraacetic acid (DOTA),[1,4,5] and 1,10-diaza-4,7,13,16-tetraoxacyclooctadecane-N,N'-diacetic acid (dacda),[1,6] are among the most promising of the paramagnetic contrast currently being developed for use in magnetic resonance imaging (MRI).[1] Indeed, [Gd.DTPA]$^-$ is now undergoing clinical trials in the United States for possible use in enhanced tumor detection protocols.[1] Nonetheless, the synthesis of other gadolinium(III) complexes remains of interest since such systems might have greater kinetic stability, superior relaxivity, or better biodistribution properties than the existing carboxylate-based contrast agents. One approach currently being pursued is based on using water-soluble porphyrin derivatives, such as tetrakis(4-sulfonatophenyl)porphyrin (TPPS).[7,8,9] Unfortunately, the large gadolinium(III) cation cannot be accommodated completely[10] within the relatively small prophyrin binding core (r≈2.0 Å[11]), and, as a consequence, gadolinium porphyrin complexes are invariably hydrolytically unstable.[7,8,12,13] Larger porphyrin-like however, might offer a means of circumventing this problem.[14-22]

As previously described, the present invention involves[23] the synthesis of a novel "expanded porphyrin" system, $1_B$ (to which the trivial name "texaphyrin" has been assigned[24]), and the structure of the bispyridine adduct of its cadmium(II) complex $2^B$. See FIG. 17 for the structures of compound or complex $1_B 11_B$. The presence in this structure of a near circular pentadentate binding core which is roughly 20% larger than that of the porphyrins,[23] coupled with the realization that almost identical ionic radii pertain for hexacoordinate $Cd^{2+}$ (r=0.92 Å) and $Gd^{3+}$ (r=0.94 Å),[25] prompted exploration of the general lanthanide binding properties of this new monoanionic porphyrin-like ligand. The synthesis and characterization of a water-stable gadolinium(III) complex ($7_B$) derived formally from a new 16,17-dimethyl substituted analogue ($6_B$)[26] of the original "expanded porphyrin" system, as well as the preparation and characterization of the corresponding europium(III) and samarium(III) complexes $8_B$ and $9_B$ (See FIG. 17).

Electronic spectra were recorded on a Beckman DU-7 spectrophotometer. IR spectra were recorded, as KBr pellets, from 4000 cm$^{-1}$ to 600 cm$^{-1}$ on a Perkin-Elmer 1320 spectrometer. Low resolution fast atom bombardment mass spectrometry (FAB MS) was performed at Austin using a Finnigan-MAT TSQ-70 instrument and either 3-nitrobenzyl alcohol or glycerol/oxalic acid as the matrix; high resolution FAB MS analyses (HRMS) were performed at the Midwest Center for Mass Spectrometry using CsI as a standard. Elementary analyses were performed by Galbraith Laboratories.

Materials. All solvents and reagents were of reagent grade quality, purchased commercially, and used without further purification. Sigma lipophilic SEPHADEX (LH-20-100) and Merck type 60 (230–400 mesh) silica gel were used for column chromatography.

Preparation of Nd complex $3_B$. The sp$^3$ form of the ligand 10[27] (50 mg, 0.1 mmol) was stirred with neodymium nitrate pentahydrate (63 mg, 0.15 mmol) and proton sponge (64 mg, 0.3 mmol) in chloroform/methanol (150 ml, v/v ½) for one day. The dark green reaction mixture was poured onto ice/water/ammonium chloride and extracted with chloroform. The organic layer was washed with aqueous ammonium chloride and concentrated under reduced pressure. The complex was chromatographed through sephadex using neat chloroform, chloroform/methanol (10:1), methanol, and water. The dark green band collected from methanol was concentrated and recrystallized from chloroform/methanol/n-hexane (ratio of chloroform to methanol is 1 to 2) to yield 13 mg of 3 (18%). For 3: UV/VIS (CH$_3$OH) $\lambda_{max}$ ($\epsilon$): 330.5 (33,096), 432.5 (85,762), 710.5 (10,724), 774.5 (38,668); FAB MS (glycerol matrix): m/e (relative intensity) 631 ($^{142}$Nd, 95), 633 ($^{144}$Nd, 100), 635 ($^{146}$Nd, 77); IR (KBr) v3360, 2965, 2930, 2870, 1610, 1560, 1450, 1400, 1350, 1250, 1205, 1135, 1080, 1050, 980, 940, 905, 755 cm$^{-1}$.

The preparation of Sm complex $4_B$ was as follows. The macrocycle 10$_B$[27] (40 mg, 0.08 mmol) was stirred with platinum oxide (18 mg. 0.08 mmol) and samarium acetate hydrate (69 mg, 0.2 mmol) under reflux in benzene/methanol (50 ml, v/v, 1/1). After two hours the reaction mixture was filtered through celite and concentrated under reduced pressure. The concentrate was purified by chromatography through Sephadex using only chloroform as an eluent. After discarding a red band, a green band was collected, concentrated in vacuo. and recrystallized from chloroform/n-hexane to give 0.8 mg of 4 (ca. 1%). For $4_B$: UV/VIS $\lambda_{max}$ nm 438, 706.5, 769; FAB MS (3-nitrobenzyl alcohol matrix): m/e (relative intensity) 635 ($^{147}$Sm, 78), 636 ($^{149}$sm, 72), 637 ($^{149}$Sm, 73), 640 ($^{152}$Sm, 100), 642 ($^{154}$Sm, 55).

The preparation of Eu complex $5_B$ was as follows. The macrocycle 10[27] (50 mg, 0.1 mmol) was stirred with europium acetate hydrate (34 mg, 0.1 mmol) and proton sponge (64 mg. 0.3 mmol) in chloroform/methanol (150 ml, v/v, ½) for one day. The reaction mixture was poured onto ice/water and extracted with chloroform. The organic layer was washed with aqueous ammonium chloride then concentrated and recrystallized from chloroform/n-hexane. The recrystallized solid was purified by column chromatography through sephadex using neat chloroform and neat methanol as eluents. The dark green band collected in methanol was concentrated to yield a small amount of a dark green solid (<1%). For 5: UV/VIS $\lambda_{max}$ nm 438, 700, 765; FAB MS (3-nitrobenzyl alcohol matrix): m/e (relative intensity) 639 ($^{151}$Eu, 94), 641 ($^{153}$Eu, 100). 4,5,9,24-Tetraethyl-10,16,17,23-tetramethyl-13,20,25,26,27-pentaazapentacyclo[20.2.1.1$^{3,6}$.1$^{8,11}$.0$^{14,19}$]heptacosa-3,5,8,10,12,14(19), 15,17,20,22,24-undecene ($11_B$). This macrocycle was prepared in ca. 90% yield from 1,2-diamino-3,4-dimethylbenzene and 2,5-bis-(3-ethyl-5-formyl-4-methylpyrrol-2-ylmethyl)-3,4-diethylpyrrole using the acid catalyzed procedure reported earlier for the preparation of 10$_B$[27] For 11: mp 200 °C. dec; $^1$H NMR $\beta$ 1.06 (6 H, t, CH$_2$CH$_3$), 1.13 (6 H, t, CH$_2$CH$_3$) 2.15 (6H, s, phenyl-CH$_3$), 2.22 (6 H, s, pyrrole-$\overline{\text{CH}_3}$), 2.38 (4 H, q, CH$_2$CH$_3$), 2.50 (4 H, q, CH$_2$CH$_3$), 3.96 (4 H, s, pyrrole$_2$-$\overline{\text{CH}_2}$), 7.19 (2 H, s, aromatic), 8.10 (2 H, s, CHN), 11.12 ($^1\overline{\text{H}}$, s, NH), 12.48 (2 H, s, NH); $^{13}$C NMR $\delta$ 9.49, 15.33, 16.47, 17.22, 17.71, 19.52, 22.41, 117.84, 120.40, 120.75, 125.11, 125.57, 134.95, 135.91, 141.63; UV/VIS $\lambda_{max}$ 367 nm; FAB MS, M+ 522; HRMS, M+ 521.35045 (calc. for C$_{34}$H$_{43}$N$_5$ 521.35185).

Preparation of Gd complex $7_B$. The sp$^3$ form of ligand 11 (42 mg, 0.08 mmol) was stirred with gadolinium acetate tetrahydrate (122 mg, 0.3 mmol) and proton sponge (54 mg, 0.25 mmol) in chloroform/methanol (150 ml, v/v ½) for one day. The dark green reaction mixture was concentrated under reduced pressure and chromatographed through silica gel (25 cm. $\times$ 1.5 cm.) which was pretreated with chloroform/triethylamine (50 ml, v/v 25/1). Chloroform/triethylamine (25/1) and chloroform/methanol/triethylamine 25/2.5/1 v/v) was used as eluents. A dark red band was first collected followed by two green bands. The last green band, which showed a clear aromatic pattern by UV/VIS, was concentrated and recrystallized from chloroform/n-hexane to give 14 mg (22%) of the Gd complex $7_B$ For $7_B$ *FAB MS (methanol/oxalic acid/glycerol matrix): m/e (relative intensity)* 671 ($^{155}$ G, 58), 672 ($^{156}$Gd, 78), 673 ($^{157}$Gd, 94), 674 ($^{158}$Gd, 100), 676 ($^{160}$Gd, 64); HRMS, M+ 674 2366 (calcd. for C$_{34}$H$_{38}$N$_5$$^{158}$Gd 674.2368): UV/VIS (CHCl$_3$) $\lambda_{max}$ nm ($\epsilon$) 339.5 (14,850), 450.5 (36,350), 694.5 (6,757), 758.0 (23,767); IR (KBr) v2990, 2960, 2900, 2830, 2765, 2700, 2620, 2515, 1710, 1550, 1440, 1410, 1395, 1365, 1265, 1220, 1180, 1150, 1105, 1090, 1060, 1040, 1095, 1045, 1015, 680 cm$^{-1}$; Anal. calc. for C$_{34}$H$_{38}$N$_5$Gd.(OH)$_2$.2H$_2$O: C, 54.89; H, 5.96; N, 9.41. Found: C, 54.49; H, 5.95; N, 8.97.

The preparation of Eu complex $8_B$ was carried out. The macrocycle 11$_B$ (53 mg, 0.1 mmol) was stirred with europium acetate hydrate (105 mg, 0.3 mmol) and proton sponge (64 mg, 0.3 mmol) in chloroform/methanol (150 ml, v/v ½) for 6 hrs. The dark green reaction mixture was concentrated under reduced pressure as described above with one exception. Chloroform/triethylamine (25:1) and chloroform/methanol/triethylamine (25:5:1) were used as eluents. The green complex 8 was recrystallized from chloroform/n-hexane to yield 26 mg of product (33%). For $8_B$: UV/VIS (CHCl$_3$) $\lambda_{max}$ nm ($\epsilon$) 339.5 (24,570), 450.5 (63,913), 696.0 (10,527), 759.0 (40,907); FAB MS (methanol/oxalic acid/glycerol matrix): m/e (relative intensity) 667 ($^{151}$Eu, 79), 669 ($^{153}$Eu, 100); HRMS, M+, 669.2336 (calc for C$_{34}$H$_{38}$N$_5$$^{153}$Eu 669.2340); IR (KBr) $\nu$ 2970, 2930, 2870, 2740, 2680, 2600, 2500, 1700, 1535, 1430, 1350, 1255, 1205, 1165, 1135, 1095, 1075, 1050, 1030, 980, 900 cm$^{-1}$; Anal. calc. for C$_{34}$H$_{38}$N$_5$Eu·(OH)20 C, 56.66; H, 5.87; N, 9.72. Found: C, 55.92; H, 5.47; N, 9.95.

The preparation of the Sm$^{3+}$ complex $9_B$ was as follows. The sp$^3$ form of the ligand ($11_B$) (52 mg, 0.1 mmol) was stirred with samarium acetate hydrate (103.5 mg, 0.3 mmol) and proton sponge (64 mg, 0.3 mmol) in chloroform/methanol (150 ml, v/v ½) for one day. The dark green reaction mixture was concentrated and purified by silica gel chromatography as described above. The resulting crude material was then recrystallized from chloroform/n-hexane to give 29 mg of 9 in 37% yield. For 9: UV/VIS (CHCl$_3$) $\lambda_{max}$ nm ($\epsilon$) 339.5 (21,617), 451.0 (56,350), 695.5 (9,393), 760.0 (35,360); FAB MS (3-nitrobenzyl alcohol): m/e (relative intensity) 663 ($^{147}$Sm, 74.8), 664 ($^{148}$Sm, 82.3), 665 ($^{149}$Sm, 84.58), 668 ($^{152}$Sm, 100, 670 ($^{154}$Sm, 78.5); HRMS, M+, 668.2300 (calc. for C$_{34}$H$_{38}$N$_5$$^{152}$Sm 668.2322); IR (KBr) $\nu$2990, 2950, 2890, 2760, 2700, 2620, 2520, 1720, 1620, 1550, 1440, 1360, 1265, 1215, 1175, 1145, 1105, 1085, 1060, 995, 945, 910, 680 cm$^{-1}$; Anal. calc for C$_{34}$H$_{38}$N$_5$Sm·(OH)$_2$·O: C, 54.08; H, 6.14; N, 9.27. Found: C, 54.30; H, 5.66; N, 9.06.

As described earlier,[23] (see Example 1) treatment of the methylene-bridged, or sp$^3$ form of the texaphyrin macrocycle $10_B$ with Cd(II) salts in air saturated methanol/chloroform at ambient temperature leads to the formation of the green Cd(II) complex 2 in roughly 25% yield, with both metal insertion and oxidation taking place concurrently under the reaction conditions. When a similar procedure was carried out using a variety of trivalent lanthanide salts [i.e. Ce(OTf)$_3$, Pr(OAc)$_3$, Nd(NO$_3$)$_3$, Sm(OAc)$_3$, Eu(OAc)$_3$, Gd(OAc)$_3$, Dy(OTf)$_3$, TbCl$_3$, Er(OTf)$_3$, Tm(NO$_3$)$_3$, and Yb(NO$_3$)$_3$] no metal complexes of 1 (or 10) were obtained (as judged by the absence of changes in the UV/visible spectrum). If, however, N,N',N'',N'''-tetramethyl-1,8-diaminonaphthalene ("proton sponge") was added to the various reaction mixtures, the high energy, low intensity band of 10 at $\lambda_{max}$=365 nm disappeared over the course of several hours to several days (depending on the salt in question) and was replaced by two strong transitions in the 435-455 nm (Soret] and 760-800 nm (Q-band) regions, suggesting that ligand oxidation and metal binding had occurred.[28] Unfortunately, isolation of these putative metal-containing products proved problematic: Direct chromatography on either silica gel or lipophilic Sephadex in general give only small quantities of metal-free oxidized ligand $1_B$ and essentially none of the desired metalated material. Indeed, only in the case of the samarium(III) acetate salt did it prove possible to isolate a trace quantity (ca. 1% yield) of the desired complexes (4) by chromatography on Sephadex. It was interesting to find, however, that a dark green neodymium(III) complex $3_B$ could be obtained in almost 20% yield by quenching the reaction mixture with ice water, extracting repeatedly with chloroform, washing with aqueous ammonium chloride, purifying by chromatography on Sephadex, and recrystallizing from chloroform/methanol/n-hexane. Unfortunately this work-up procedure proved ineffective in the case of the other putative lanthanide complexes (including, unfortunately, that derived from Gd$^{3+}$), although it did prove possible to obtain trace quantities of the europium(III) complex ($5_B$) using this procedure.

Since spectral evidence suggested that metal uptake and ligand oxidation were occurring when the sp$^3$ macrocycle $10_B$ was treated with numerous other Ln$^{3+}$ salts, it was puzzling that only the neodymium(111) complex (3) could be isolated in reasonable yield. A careful analysis suggested that, in certain instances, notably Sm$^{3+}$, Eu$^{3+}$, Gd$^{3+}$, the problem was not due to hydrolytic instability. Rather, it derived from the very high water solubility of the lanthanide complexes which precluded reextraction back into organic solvents following the initial aqueous washes! This observational hypothesis led to the consideration that more hydrophobic texaphyrin analogues would prove valuable in the preparation and isolation of "expanded porphyrin" lanthanide complexes.

To test the above assumption, a simple dimethylated analogue (IIB) of the original sp$^3$ hybridized ligand $10_B$ was prepared. This new, more hydrophobic, sp$^3$ hybridized ligand was obtained in ca. 90% yield by condensing 1,2-diamino-4,5-dimethylbenzene with 2,5-Bis-(3-ethyl-5-formyl-4-methylpyrrol-2-ylmethyl)-3,4-diethylpyrrole under acid catalyzed conditions identical to those used to prepare 10.[27] Treatment of this texaphyrin precursor with Gd(OAc)$_3$, Eu(OAc)$_3$, and Sm(OAc)$_3$ under reaction and work-up conditions similar to those used to obtain $3_B$, then gave the cationic complexes $7_B$, $8_B$, and $9_B$, as their dihydroxide adducts,[29] in 22%, 33%, and 37% yields respectively! It appears that these increased yields derive directly from the increased hydrophobicity of the new dimethyl substituted texaphyrin ligand system (6B)

The new lanthanide complexes reported here are unique in several ways. For instance, as judged by fast atom bombardment mass spectrometric (FAB MS) analysis, complexes $3_B$–$5_B$ and $7_B$–$9_B$ are mononuclear 1:1 species, a conclusion that is further supported, in the case of compounds $7_B$–$9_B$, by both high resolution FAB MS accurate molecular weight determinations and combustion analysis. In other words, we have found no evidence of 1:2 metal to ligand "sandwich" systems, or higher order combinations as are often found in the case of the better studied lanthanide porphyrins.[31]

The electronic spectra represents a second remarkable feature of these new materials: All six lanthanide complexes isolated to date display a dominant Soret-like transition in the 435-455 nm region which is considerably less intense than that observed in the corresponding metalloporphyrins (c.f. FIG. 18),[7] and show a prominent low energy Q-type band in the 760-800 nm region. This latter feature is diagnostic of this class of 22 $\pi$-electron "expanded porphyrins"[23] and is both considerably more intense and substantially red-shifted (by ca. 200 nm!) as compared to the corresponding transitions in suitable reference lanthanide prophyrins (e.g., [Gd.TPPS]+, $\lambda_{max}$ ≈575 nm[7]). Within the context of these general observations, it is interesting to note that complexes derived from the somewhat more electron rich ligand $6_B$ all display Q-type bands that are blue shifted by ca. 5–15 nm as compared to those obtained from the original texaphyrin $1_B$.

A third notable property of complexes $7_B$–$9_B$ is their high solubility in both chloroform and methanol. The fact that these three complexes are also moderately soluble (to roughly $10^{-3}$ M concentrations) in 1:1 (v.v.) methanol/water mixtures was of particular interest. Moreover, as initially suggested on the basis of the preliminary studies with 3–5 discussed above, these materials are stable to these solvent conditions. For instance, a $3.5 \times 10^{-5}$ M solution of the gadolinium complex $7_B$ in 1:1 (v.v.) methanol/water at ambient temperature shows less than 10% bleaching of the Soret and Q-type bands when monitored spectroscopically over the course of 2 weeks. This suggests that the half-life for decomplexation and/or decomposition of this complex is $\geq$ 100 days under these conditions. Under the conditions of the experiment described above, no detectable shifts in the position of the Q-type band are observed yet the Q-type transition of the free-base $6_B$ falls ca. 20 nm to the blue of that of $7_B$, while shifts in this direction would be expected if simple demetalation were the dominant pathway leading to the small quantity of observed spectral bleaching.

The strong hydrolytic stability of complexes $7_B$–$9_B$ is in marked contrast to that observed for simple, water soluble gadolinium porphyrins, such as [Gd.TPPS]+, which undergo water-induced demetalation in the course of several days when exposed to an aqueous environment.[7,8] It thus appears likely that gadolinium-(III) complexes derived from the new texaphyrin ligand $6_B$, or its analogues, should provide the basis for developing new paramagnetic contrast reagents for use in MRI applications. In addition, the ease of preparation and stable mononuclear nature of complexes $7_B$–$9_B$ suggests that such expanded porphyrin ligands might provide the basis for extending further the relatively underdeveloped coordination chemistry of the lanthanides.

Literature citations in the following list are incorporated by reference herein for the reasons cited.

REFERENCES

1. For a recent review see: Lauffer, R. B. Chem. Rev. 1987, 87, 901–927.
2. Kornguth, S. E.; Turski, P. A.; Perman, W. H.; Schultz, R.; Kalinke, T.; Reale, R.; Raybaud, F. J. Neurosurg. 1987, 66, 898–906.
3. Koenig, S. H.; Spiller, M.; Brown, R. D.; Wolf, G. L. Invest. Radiol. 1986, 21, 697–704. Cacheris, W. p.; Nickle, S. K.; Sherry, A. D. Inorg. Chem. 1987, 26, 958–960.
5. (a) Loncin, M. F.; Desreux, J. F.; Merciny, E. Inorg. Chem. 1986, 25, 2646–2648. (b) Spirlet, M.-R.; Rebizant, J.; Desreux, J. F.; Loncin, M.-F. Inorg. Chem. 1984, 23, 359–363.
6. (a) Chang, C. A.; Sekhar, V. C. Inorg. Chem. 1987, 26, 1981–1985. (b) Chang, C. A.; Ochaya, V. O. Inorg. Chem. 1986, 25, 355–358. (c) Chang, C. A.; Rowland, M. E. Inorg. Chem. 1983, 22, 3866–3869.
7. Horrocks, W. D.; Hove, E. G. J. Am. Chem. Soc. 1978, 100, 4386–4392.
8. Lyon, R. C.; Faustino, P. J.; Cohen, J. S.; Katz, A.; Mornex, F.; Colcher, D.; Baglin, C.; Koenig, S. H.; Hambright, P. Magn. Reson. Med. 1987, 4, 24–33.
9. Radzki, S.; Krauz, P.; Gaspard, S.; Giannotti, C. Inorg. Chim. Acta 1987, 138, 139–143.
10. Buchler, J. W. in "The Porphyrins," Dolphin, D. ed., Academic Press, New York, 1978, Vol. 1, Chapter 10.
11. Hoard, J. L. in "Porphyrins and Metalloporphyrins"; Smith, K., Ed; Elsevier, Amsterdam, 1975, Chapter 8.
12. (a)( Horrocks, W. D., Jr.; Wong, C.-P. J. Am. Chem. Soc. 1976, 98, 7157–7162. (b) Wong, C.-P.; Venteicher, R. F.; Horrocks, W. D., Jr. J. Am. Chem. Soc. 1974, 96, 7149–7150.
13. Srivastava, T. S. Bioinor9. Chem. 1978, 8, 61–76.
14. Although several large porphyrin-like aromatic macrocycles, including the "sapphyrins",[15,16] "platyrins",[17] "pentaphyrin",[18] and "[26]porphyrin"[19] have been prepared in their metal-free forms, and a uranyl complex has been stabilized with a large "superphthalocyanine",[20] we are not aware of any lanthanide complexes formed from these systems.[21]
15. Bauer, V. J.; Clive, D. R.; Dolphin, D.; Paine, J. B. III; Harris, F. L.; King, M. M.; Loder, J.; Wang, S.-W. C.; Woodward, R. B. J. Am. Chem. Soc. 1983, 105, 6429–6436.
16. Broadhurst, M. J.; Grigg, R.; Johnson, A. W. J. Chem. Soc. Perkin Trans. 1, 1972, 2111–2116.
17. (a) Berger, R. A.; LeGoff, E. Tetrahedron Lett. 1978, 4225–4228. (b) LeGoff, E.; Weaver, O. G. J. Org. Chem. 1987, 710–711.
18. (a) Rexhausen, H.; Gossauer, A. J. Chem. Soc., Chem. Commun. 1983, 275. (b) Gossauer, A. Bull. Soc. Chim. Belg. 1983, 92, 793–795.
19. Gosmann, M.; Franck, B. Angew. Chem. 1986, 98, 1107–1108; Angew. Chem. Int. Ed. Eng. 1986, 25, 1100–1101.
20. (a) Day, V. W.; Marks, T. J.; Wachter, W. A. J. Am. Chem. Soc. 1975, 97, 4519–4527. (b) Marks, T. J.; Stojakovic, D. R. J. Am. Chem. Soc. 1978, 100, 1695–1705. (c) Cuellar, E. A.; Marks, T. J. Inorg. Chem. 1981, 20, 3766–3770.
21. Sessler, J. L; Cyr, M.; Murai, T. Comm. Inorg. Chem., in press.
22. For examples of lanthanide cationic complexes stabilized by more conventional Schiff base macrocycles see for instance: (a) Backer-Dirks, J. D. J.; Gray, C. J.; Hart, F. A.; Hursthouse, M. B.; Schoop, B. C. J. Chem. Soc., Chem. Commmun. 1979, 774–775. (b) De Cola, L.; Smailes, D. L.; Vallarino, L. M. Inorg. Chem. 1986, 25, 1729–1732. (c) Sabbatini, N.; De Cola, L.; Vallarino, L. M.; Blasse, G. J. Phys. Chem. 1987, 91, 4681–4685. (d) Abid, K. K.; Fenton, D. E.; Casellato, U.; Vigato, P.; Graziano, R. J. Chem. Soc., Dalton Trans. 1984, 351. (e) Abid, K. K.; Fenton, D. E. Inorg. Chim. Acta 1984, 95, 119–125. (f) Sakamoto, M. Bull Chem. Soc. Jpn. 1987, 60, 1546–1548.
23. Sessler, J. L.; Murai, T.; Lynch, V.; Cyr, M. J. Am. Chem. Soc. 1988, 110, 5586–5588.
24. Chemical & Engineering News August 8, 1988, 26–27.
25. Cotton, F. A.; Wilkinson, G. "Advanced Inorganic Chemistry, 4th ed.," John Wiley, New York, 1980, pp. 589 and 982.
26. The systematic name for this compound is 4,5,9,24-tetraethyl-10,16,17,23-tetramethyl-13,20,25,26,27-pentaazapentacyclo-[20.2.1.1$^{3,6}$,1$^{8,11}$,0$^{14,19}$]heptacosa-1,3,5,7,9,11(27),12,14,16,18,20,22(25),23-tridecaene.
27. Sessler, J. L.; Johnson, M. R.; Lynch, V. J. Org. Chem. 1987, 52, 4394–4397.

28. The relation between the optical bands (nm) observed just after the reaction and the trivalent lanthanide cation employed are as follows. Ce: 453, 782; Pr: 437, 797; Nd: 439, 786; Sm: 438, 769; Eu: 438, 765; Gd: 438, 765; Tb: 439, 764; Dy: 438, 765; Tm: 437, 765; Yb: 437, 764.

29. As judged by the IR and microanalytical data, under the reaction and work up conditions, hydroxide anions serve to displace the acetate ligands presumably present following the initial metal insertion procedure. Similar exchanges have also observed in the case of the cadmium complex 2 (prepared from Cd(OAc)$_2$) where $^1$H NMR analyses can be made with ease.[30]

30. Murai, T.; Hemmi, G.; Sessler, J. L., unpublished results.

31. (a) Buchler, J. W.; Cian, A. D.; Fischer, J.; Kihn-Botulinski, M.; Paulus, H.; Weiss, R. J. Am. Chem. Soc. 1986, 108, 3652-3659. (b) Buchler, J. W.; Cian, A. D.; Fischer, J.; Kihn-Botulinski, M.; Weiss, R. Inorg. Chem. 1988, 27, 339-345. (c) Buchler, J. W.; Scharbert, B. J. Am. Chem. Soc. 1988, 110, 4272-4276. (d) Buchler, J. W.; Kapellmann, H.-G.; Knoff, M.; Lay, K.-L.; Pfeifer, S. Z. Naturforsch. 1983, 38b, 1339-1345.

EXAMPLE 4

The photophysical properties of a new series of tripyrroledimethine-derived "expanded porphyrins" ("texaphyrins") are reported; these compounds show strong low energy optical absorptions in the 730-770 nm spectral range as well as a high triplet quantum yield, and act as efficient photosensitizers for the production of singlet oxygen in methanol solution.

Photodynamic therapy is among the more promising of modalities currently being considered for the treatment of localized neoplasia[1] and eradication of viral contaminants in blood.[2] As a result, considerable effort has been devoted to the development of effective photochemo-therapeutic agents.[3] To date, porphyrins and their derivatives, phthalocyanines, and naphthalocyanines have been among the most widely studied compounds in this regard. Unfortunately, all of these dyes suffer from critical disadvantages. While porphyrin derivatives have high triplet yields and long triplet lifetimes (and consequently transfer excitation energy efficiently to triplet oxygen),[3b,3g] their absorption in the Q-band region often parallels that of heme-containing tissues. Phthalocyanines and naphthalocyanines absorb in a more convenient spectral range but have significantly lower triplet yields;[4] moreover, they tend to be quite insoluble in polar protic solvents, and are difficult to funtionalize. Thus at present the development of more effective photochemotherapeutic agents appears to require the synthesis of compounds which absorb in the spectral region where living tissues are relatively transparent (i.e., 700-1000 nm),[1d] have high triplet quantum yields, and are minimally toxic. The present inventors have recently reported[5] (see Example 1) the synthesis of a new class of aromatic prophyrin-like macrocycles, the tripyrroledimethine-derived "texaphyrins", which absorb strongly in the tissue-transparent 730-770 nm range. The photophysical properties of metallotexaphyrins $1_C$-$7_C$ parallel those of the corresponding metallaporphyrins and the diamagnetic complexes $1_C$-$4_C$ sensitize the production of $^1O_2$ in high quantum yield. FIG. 19 shows the schematic structure, metal complexes and derivatives of compounds of the present invention ($1_C$-$7_C$).

Figure 21A:
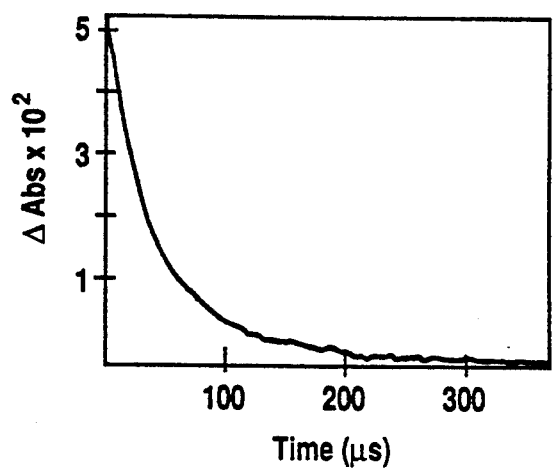
FIG. 21 shows the triplet-triplet transient difference spectrum of $1_C.Cl$ in deoxygenated methanol recorded 1 μs after irradiation with a 10 ns pulse of 355 nm light (80 mJ). The inset shows the rate of return to ground state, as monitored at 480 nm, and corresponds to a triplet lifetime of 67 μs.
Figure 21:
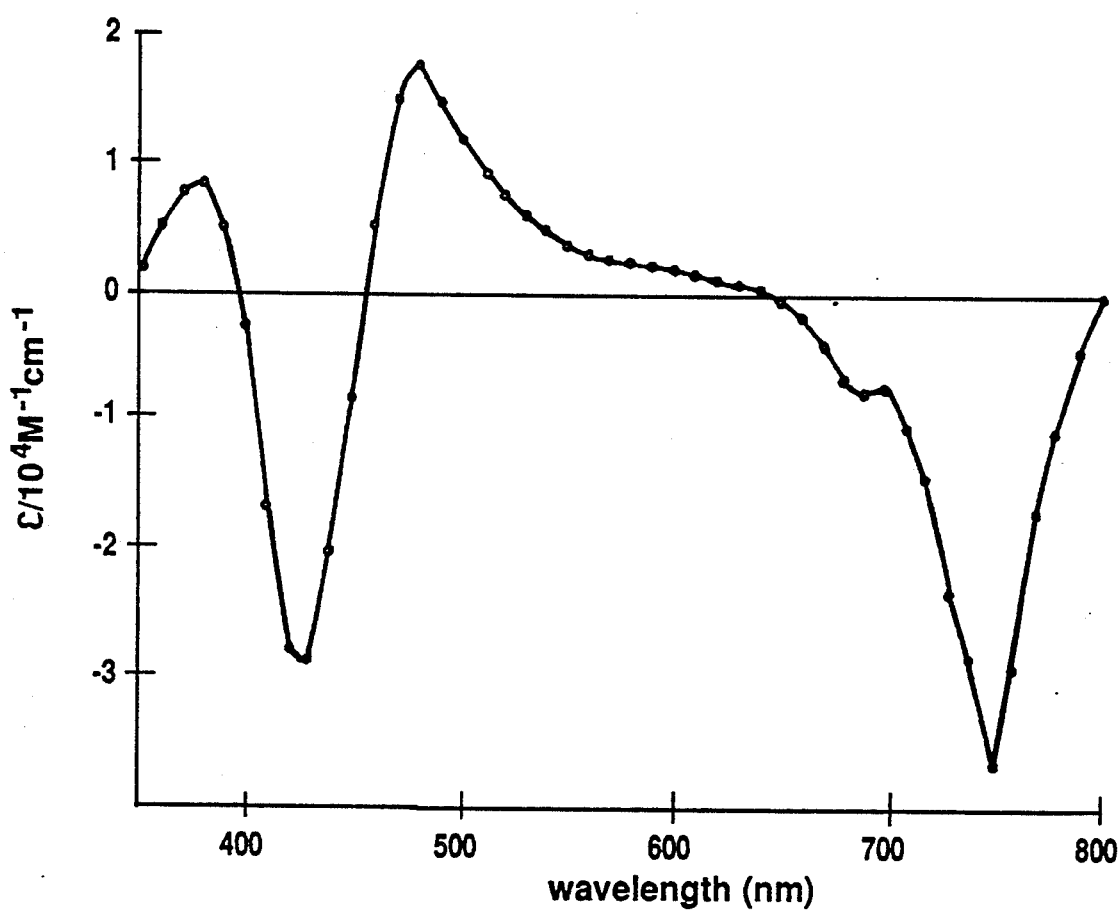

The absorption spectrum of $1_C$·Cl is shown in FIG. 20. This spectrum, which is representative of this class of compounds (cf. Table 3), is characterized by strong Soret- and Q-type bands, the latter being of particular interest. The fluorescence excitation spectrum of this complex, monitored at the emission maximum (ca. 780 nm; see inset to FIG. 20), and the absorption spectrum are superimposable in the visible region (370-800 nm) showing that internal conversion to the first excited singlet state is quantitative upon photoexcitation in the Soret or Q-band regions. While the fluorescence quantum yields ($\Phi_f$) for $1_C$-$4_C$ are only 0-1%, the quantum yields for triplet formation ($\Phi_t$) of these diamagnetic metalltexaphrins can approach unity and resemble those found for metalloporphyrins.[6] The triplet-triplet transient spectrum of $1_C$·Cl, given in FIG. 21, shows bleaching in the Soret- and Q-bands of the ground state and a positive absorbance change in the 450-600 nm region, again reminiscent of metalloporphyrin triplet spectra.[7] The inset of FIG. 21 shows the decay of this triplet state in deoxygenated methanol, from which a lifetime ($\tau_t$) of 67 μs is calculated. Similar triplet spectra, lifetimes, and quantum yields were found for other diamagnetic metallotexaphyrin derivatives in methanol and for $1_C$·Cl in mixed methanol-water solutions. Interestingly, low temperature phosphorescence could not be observed for any of the compounds in methanol glasses. Finally, several complexes containing paramagnetic metal ions (e.g. Mn$^{II}$, Sm$^{III}$, and Eu$^{III}$, structures $5_C$-$7_C$) were investigated. They proved to be non-luminescent and their triplet excited states could not be detected with our laser flash photolysis set-up, which has a time resolution of ca. 10 ns.

In methanol solution, the triplet excited states of $1_C$-$4_C$ were quenched by molecular oxygen with biomolecular rate constants of $(2.6\pm0.2)\times10^9$ dm$^3$ mol$^{-1}$ s$^{-1}$. In aerated solution, the triplet state decay profile could be described in terms of a single exponential process with an average lifetime of (175±20) ns; thus, interaction between the triplet species and O$_2$ is quantitative. Laser excitation (355 nm, 80 mJ, 10 ns) of the compound in aerated methanol gave no redox products (e.g. texaphyrin cation and superoxide anion) but, using a Ge diode,[8] the production of $^1O_2$ was observed clearly from its characteristic luminescence at 1270 nm. This luminescence decayed with a lifetime of 12.5±0.3 μs and its initial intensity, as extrapolated to the centre of the laser pulse, was a linear function of the number of photons absorbed by the texaphyrin complex. Comparison of the initial intensity with that obtained using tetrakis (4-hydroxyphenyl)porphyrin (THPP) as photosensitizer[3b] under identical conditions allowed calculation of the quantum yields for production of singlet oxygen ($\Phi_{^1O_2}$). The derived values are seen to parallel the triplet quantum yields (Table 3); the triplet state reaction appears to partition between generation of $^1O_2$ (74-78%) and formation of vibrationally excited O$_2$ (22-26%). These $\Phi_{O_2}$ values compare favourably with those observed with porphyrins[3b] and are much superior to values obtained with phthalocyanines and naphthalocyanines[4] due to the improved triplet state yields. Thus diamagnetic texaphyrin complexes appear to be highly efficient photosensitizers for the formation of $^1O_2$.

TABLE 3

Optical and photophysical properties of metallotexaphyrins in CH$_3$OH.

| Complex | Absorption $\lambda_{max}$(nm) | | Emission $\lambda_{max}$(nm) | $\Phi_f$ (±10%) | $\Phi_t$ (±5%) | $\tau_t$ (μs) | $\Phi_{O_2}^1$ (±10%) | S$^{(a)}$ |
|---|---|---|---|---|---|---|---|---|
| 1$_C$Cl | 410 | 732 | 767 | 0.013 | 0.82 | 67 | 0.61 | 0.74 |
| 2$_C$Cl | 412 | 738 | 765 | 0.012 | 0.88 | 37 | 0.65 | 0.73 |
| 3$_C$NO$_3$ | 417 | 759 | 780 | 0.011 | 0.88 | 55 | 0.69 | 0.78 |
| 4$_C$NO$_3$ | 421 | 760 | 788 | 0.009 | 0.97 | 36 | 0.74 | 0.76 |
| 5$_C$OH | 420 | 760 | — | <0.001 | ND$^{(b)}$ | — | <0.05 | — |
| 6$_C$(OH)$_2$ | 450 | 763 | — | <0.001 | ND | — | <0.05 | — |
| 7$_C$(OH)$_2$ | 451 | 762 | — | <0.001 | ND | — | <0.05 | — |
| SiNC$^{(c)}$ | 310 | 776 | 780 | — | 0.39 | 331 | 0.35 | 0.90 |

$^{(a)}$S = $\Phi_{O_2}^1/\Phi_t$.
$^{(b)}$ND = not detected
$^{(c)}$SiNC = bis(tri-n-hexylsiloxy)(2,3-naphthalocyaninato) silicon in benzene; see reference 4.

In summary, the new metallotexaphrin complexes discussed here show three important optical properties which make them unique among existing porphyrin-like macrocycles. They absorb strongly in a physiologically important region (i.e. 730–770 nm), form long-lived triplet states in high yield, and act as efficient photosensitizers for the formation of singlet oxygen (see, e.g. FIG. 21). These properties, coupled with their high chemical stability and appreciable solubility in polar media, suggest that these cationic complexes could serve as viable photosensitizers in emerging photodynamic protocols. Preliminary in vitro studies of 3$_C$.NO$_3$ in 10% human serum, in which a significant decrease in herpes simplex (HSV-1) infectivity and lymphocyte mitogenic activity are observed upon irradiation at 767 nm,[9] affirm the feasibility of this approach.

REFERENCES 1. (a) For an overview see: C. J. Gomer, Photochem. Photobiol. 1987, 46, 561 (this special issue is entirely devoted to this topic). See also: (b) T. J. Dougherty, Photochem. Photobiol. 1987, 45, 879; (c) A. R. Oseroff, D. Ohuoha, G. Ara, D. McAuliffe, J. Foley, and L. Cincotta, Proc. Natl. Acad. Sci. U.S.A., 1986, 83, 9729; (d) S. Wan, J. A. Parrish, R. R. Anderson, and M. Madden, Photochem. Photobiol., 1981, 34, 679; (e) A. Dahlman, A. G. Wile, R. B. Burns, G. R. Mason, F. M. Johnson, and M. W. Berns, Cancer Res., 1983, 43, 430.
2. J. L. Matthews, J. T. Newsam, F. Sogandares-Bernal, M. M. Judy, H. Skiles, J. E. Levenson, A. J. Marengo-Rowe, and T. C. Chanh, Transfusion, 1988, 28, 81.
3. (a) M. R. Detty, P. B. Merkel, and S. K. Powers, J. Am. Chem. Soc., 1988, 110, 5920; (b) R. Bonnett, D. J. McGarvey, A. Harriman, E. J. Land, T. G. Truscott, and U-J. Winfield, Photochem. Photobiol., 1988, 48, 271; (c) R. Bonnett, S. Ioannou, R. D. White, U-J. Winfield, and M. C. Berenbaum, Photobiochem. Photobiophys. 1987, Suppl., 45; (d) P. A. Scourides, R. M. Bohmer, A. H. Kaye, and G. Morstyn, Cancer Res., 1987, 47, 3439; (e) M. C. Berenbaum, S. L. Akande, R. Bonnett, H. Kaur, S. Ioannou, R. O. White, and U-J. Winfield, Br. J. Cancer, 1986, 54, 717; (f) J. D. Spikes, Photochem. Photobiol., 1986, 43, 691; (g) D. Kessel and C. J. Dutton, Photochem. Photobiol., 1984, 40, 403.
4. P. A. Firey and M. A. J. Rodgers, Photochem. Photobiol., 1987, 45, 535.
5. (a) J. L. Sessler, T. Murai, V. Lynch, and M. Cyr, J. Am. Chem. Soc., 1988, 110, 5586. (b) J. L. Sessler, T. Murai, and G. Hemmi, submitted to Inorg. Chem.
6. "The Porphyrins"; D. Dolphin, Ed., Academic Press: New York, 1978-1979, Vols. I-VII.
7. A. Harriman, J. Chem. Soc., Faraday Trans. 2, 1981, 77, 1281.
8. M. A. J. Rodgers and P. T. Snowden, J. Am. Chem. Soc., 1982, 104, 5541.
9. M. H. Judy, J. L. Matthews, G. Hemmi, J. L. Sessler, to be published.

EXAMPLE 5

Acquired immunodeficiency syndrome (AIDS) and cancer are among the most serious public health problems facing our nation today. AIDS, first reported in 1981 as occurring among male homosexuals,[1] is a fatal human disease which has now reached pandemic proportions. Cancer, in spite of some very significant advances in diagnostics and treatment in recent years, remains the third leading cause of death in this country. Finding better ways to detect, treat, and reduce the transmission of these disorders are thus research objectives of the highest importance.

One of the more promising new modalities currently being explored for use in the control and treatment of tumors is photodynamic therapy (PDT).[1-5] This technique is based on the use of a photosensitizing dye, which localizes at, or near, the tumor site, and when irradiated in the presence of oxygen serves to produce cytotoxic materials, such as singlet oxygen ($O_2(^1\Delta_g)$), from otherwise benign precursors (e.g. ($O_2(^3\Sigma_g-)$)). Much of the current excitement associated with PDT derives from just this property: In marked contrast to current methods (e.g. conventional chemotherapy), in PDT the drugs themselves can (and should) be completely innocuous until "activated" with light by an attending physician. Thus a level of control and selectivity may be attained which is not otherwise possible.

At present, diamagnetic porphyrins and their derivatives are considered the dyes of choice for PDT. It has been known for decades that porphyrins, such as hematoporphyrin, localize selectively in rapidly growing tissues including sarcomas and carcinomas,[6] although the reasons for this selectivity remain recondite. Currently most attention is focusing on the so-called hematoporphyrin derivative (HPD),[2-5,7-21] an incompletely characterized mixture of monomeric and oligomeric porphyrins produced by treating hematoporphyrin dihydrochloride with acetic acid-sulfuric acid followed by dilute base.[22-27] Fractions rich in the oligomeric species, which are believed to have the best tumor-localizing ability,[23,26] are marketed under the trade name Photofirin II ® (PII) and are currently undergoing phase III clinical trials for obstructed endobronchial tumors and superficial bladder tumors. Here, the mechanism of action is thought to be largely, if not entirely, due to the photoproduction of singlet oxygen ($O_2(^1\Delta_g)$), although alternative mechanisms of action, including those involving superoxide anion or hydroxyl and/or porphyrin-based radicals cannot be entirely ruled out.[28-33]

Singlet oxygen is also believed to be the critical toxic species operative in experimental photsensitized blood purification procedures.[34-39] This very new application of photodynamic therapy is of tremendous potential importance: It may provide a safe and effective means of removing enveloped viruses such as HIV-1, herpes simplex (HSV), cytomegalovirus (CMV), various forms of hepatitis, as well as other opportunistic blood-borne infections (e.g. bacteria and malaria plasmodium) from transfused whole blood. Given that AIDS is currently an ineffectively treated and usually fatal disease, the benefit of such a blood purification procedure would be of inestimable value.

At present, sexual relations and needle-sharing are the dominant mechanisms for the spread of AIDS.[1] An increasing percentage of AIDS infections, however, are now occurring as a result of blood transfusions.[1,40-43] Unfortunately, banked blood components are essential products for the practice of modern medicine and as a result this method of transmission is not likely to be precluded by simple changes in lifestyle. Rather, an absolutely fail-proof means must be developed to insure that all stored blood samples are free of the AIDS virus (and ideally all other blood-borne pathogens). To a certain extent this can be accomplished by screening the donors' histories and carrying out serologic tests. At present, however, the serologic tests for HIV-1 are insufficient to detect all infected blood samples, in particular, those derived from donors who have contacted the disease but not yet produced detectable antibodies.[42,43] In addition, new mutants of the AIDS virus have been detected; some or all of these may escape detection by current means.1 Thus, an antiviral system is needed which removes any form of HIV-1 from stored blood. This is particularly important since a stored blood sample from one infected donor could potentially end up being administered to several different patients, in, for instance, the course of pediatric care.

Ideally, any blood purification procedure used to remove AIDS virus or other blood-borne pathogens should operate without introducing undesirable toxins, damaging normal blood components, or inducing the formation of harmful metabolites. In general, this precludes the use of common antiviral systems such as those based on heating, UV irradiation, or purely chemical means. A promising approach is the photodynamic one alluded to above. Here, preliminary studies, carried out by collaborators at the Baylor Research Foundation, Dr. Matthews and his team,[34-37] and others,[38,39] have served to show that HPD and PII, in far lower dosages than are required for tumor treatment, can act as efficient photosensitizers for the photo-deactivation of cell-free HIV-1, HIV, hepatitis and other enveloped viruses. On the basis of available data, it is considered likely that the success of this procedure derives from the fact that these dyes localize selectively at or near the morphologically characteristic, and physiologically essential, viral membrane ("envelope") and catalyze the formation of singlet oxygen upon photoirradiation. The singlet oxygen so produced is believed, in turn, to destroy the essential membrane envelope. This kills the virus and eliminates infectivity photodynamic blood purification procedures, therefore, apparently rely on the use of photosensitizers which localize selectively at viral membranes, just as more classic tumor treatments require dyes that are absorbed or retained preferentially at tumor sites. To the extent that this is true, simple enveloped DNA viruses like HSV-1 will prove to be good models for testing putative photosensitizers for potential use in killing the far more hazardous HIV-1 retrovirus. It is important to note, however, that this correspondence holds only as far as freely circulating (as opposed to intracellular) viruses are concerned. Complete prophylactic removal of HIV-1 from blood products will require the destructive removal of the virus from within monocytes and T lymphocytes.[44]

Critical as are the potential anti-tumor and anti-viral photodynamic applications which are currently being explored using HPD and PII, it is important to realize that these photosensitizers are not ideal. Indeed, this "first generation" of dyes suffers from a number of serious deficiencies which may in fact militate against their eventual use in biomedical applications. They contain a range of chemical species, they are neither catabolized nor excreted rapidly from the body, and they absorb but poorly in the red part of the spectrum where blood and other bodily tissues are most transparent.[5] Each of these deficiencies can and does have important clinical consequences. For instance, the fact that HPD and PII do not contain a single chemically well-defined constituent, coupled with the fact that the active components have yet to be identified with certainty,[23-27] means that the effective concentrations can and often do vary from preparation to preparation. Thus the dosage, and the light fluence, cannot necessarily be optimized and predetermined for any particular application. Moreover, the fact that they are not metabolized rapidly means that significant quantities of these dyes will remain in stored blood units after prophylactic photoinduced HIV-1 removal and remain in patients' bodies long after photodynamic tumor treatment. The latter retention problem, in particular, is known to be quite serious: HPD and PII localize in the skin and induce photosensitivity in patients for weeks after administration.[5,45]

Figure 22:
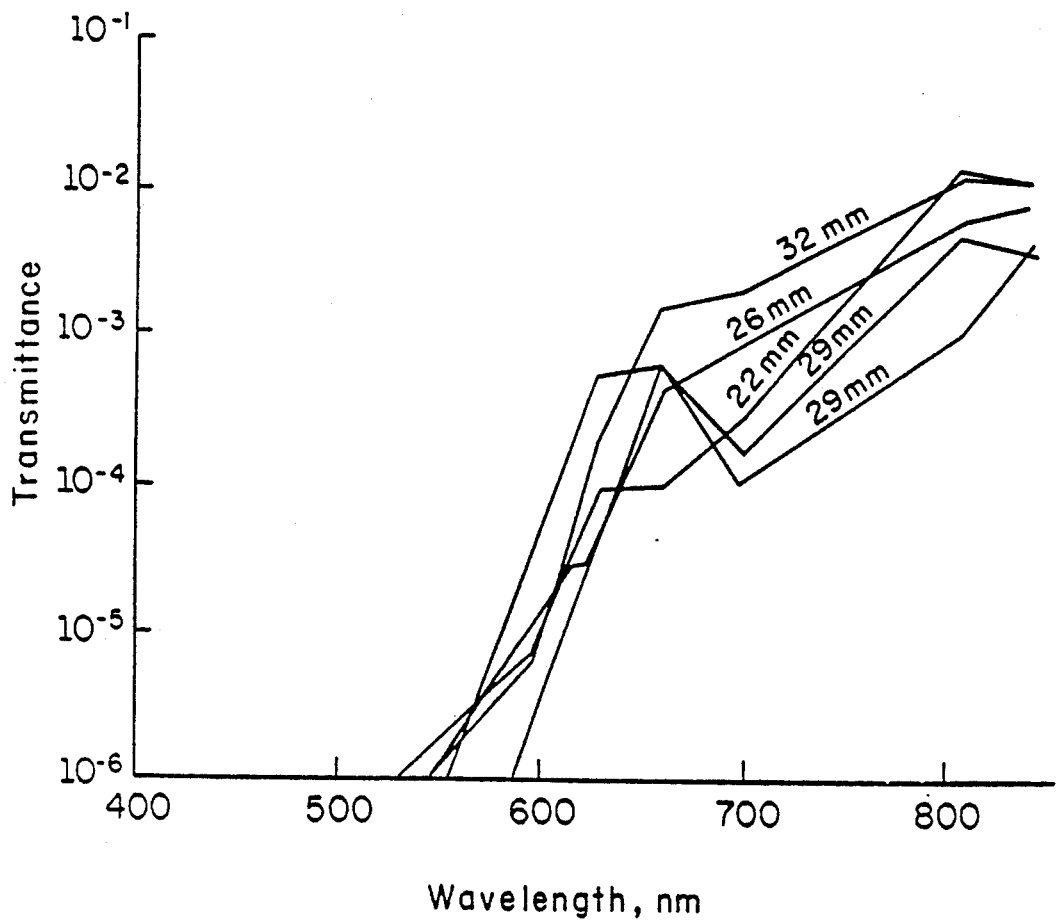
FIG. 22 shows the spectral transmittance through human abdominal wall with a thickness of 22-32 mm[47] (reference 47 taken from Example 5).

It is, however, the last of the above shortcomings (the lack of a truly low-energy transition) that is considered to be most serious: Because the longest wavelength absorption maximum for these dyes falls at 630 nm, most of the incipient energy used in photo-treatment is dispersed or attenuated before reaching the center of a deep-seated tumor and as a result little of the initial light is available for singlet oxygen production and therapy.[46-48] Indeed, one study, which used a mouse model and a 3 mm tumor implanted beneath the skin served to indicate that as much as 90% of the energy is lost by the base of the tumor.[46] As illustrated by the data in FIG. 22, taken from ref. [47,] far more effective treatment deep-seated or large tumors might be possible if photosensitizers could be developed which absorb in the >700 nm region, provided, of course, they retain the desirable features of HPD and PII (e.g. selective localization in target tissues and low dark toxicity). The present aspect of the invention involves development of such improved photosensitizers for use in photdynamic tumor treatment and blood purification protocols.

1. Easily available
2. Low intrinsic toxicity
3. Long wavelength absorption

4. Efficient photosensitizer for singlet oxygen production
5. Fair solubility in water
6. Selective up-take in tumor tissue and/or
7. Showing high affinity for enveloped viruses
8. Quick degradation and/or elimination after use
9. Chemically pure and stable
10. Easily subject to synthetic modification The list summarizes those features which would be desirable in biomedical photosensitizers. Clearly, there is going to be some variability in the requirements, depending on application. For instance, photosensitizers designed for use in blood purification protocols should be designed to be less chemically stable than those used for photodynamic therapy. The idea being, that following irradiation the dyes will undergo rapid degradation or hydrolysis to yield nontoxic and nonactive metabolites. For tumor treatment, greater stability appears desirable as longer times are apparently required to achieve selective localization in the neoplastic tissues. In both cases, of course, low toxicity and good long-wavelength absorption and photosensitization properties are an absolute must.

In recent years, considerable effort has been devoted to the synthesis and study of new potential photosensitizers which might meet these desiderata. Although a few of these have consisted of classic dyes such as those of the rhodamine and cyanine classes,49-51 many have been porphyrin derivatives with extended $\pi$ networks.[56-67] Included in this latter category (See FIG. 23) are the purpurins[55] (e.g. $1_D$) and verdins[56] (e.g. $2_B$) of Morgan and other chlorophyll-like species,[57-59] the benz-fused prophyrins ($3_D$) of Dolphin et al.,[60] and the sulfonated phthalocyanines and napthophthalocyanines ($4_D$) studied by Ben-Hur,[61] Rodgers,[62] and others.[63-67] Of these, only the napthophthalocyanines absorb efficiently in the most desirable >700 nm spectral region. Unfortunately, these particular dyes are difficult to prepare in a chemically pure, water soluble form and are relatively inefficient photosensitizers for singlet oxygen production, perhaps even acting photodynamically via other oxygen derived toxins (e.g. superoxide). Thus a search continues for yet a "third generation" of photosensitizers which might better meet the ten critical criteria listed above.

It is an important aspect of the present invention that an improved "third generation" of photosensitizers can be obtained using large, pyrrole-containing "expanded porphyrins". These systems, being completely synthetic, can, at least in principle, be tuned so as to incorporate any desired properties. Unfortunately, the chemistry of such systems is still in its infancy: In marked contrast to the literature of the porphyrins, and related tetrapyrrolic systems (e.g. phthalocyanines, chlorins, etc.), there are only a few reports of larger pyrrole-containing systems, and only a few of these meet the criterion of aromaticity deemed essential for long-wavelength absorption and singlet oxygen photosensitization.[68] Indeed, to date, in addition to the present inventors' studies of texaphrin $5_D$,[69] (see FIG. 23), and "sapphyrin" $6_D$, first produced by the groups of Woodward[70] and Johnson[71], there appear to be only two large porphyrin-like systems which might have utility as photosensitizers. These are the "platyrins" of LeGoff (exemplified by [22]platyrin $7_D$)[72] and the vinylogous porphyrins of Franck (represented by [26]porphyrin $8_D$).[73] Unfortunately, to date, little has been published on the photodynamic aspects of these materials, although comments have been included in the most recent synthetic reports which suggest that such studies are in progress. The present studies, however, of expanded porphyrins $5_D$ and $6_D$, indicate that an expanded porphyrin approach to photodynamic therapy is potentially quite promising. Interestingly, the porphycenes[74] (e.g. $9_D$, a novel class of "contracted porphyrins" also show substantial promise as potential photosensitizers.[75]

The present invention involves a major breakthrough in the area of ligand design and synthesis: synthesis the first rationally designed aromatic pentadentate macrocyclic ligand, the tripyrroledimethine-derived "expanded porphyrin"$5_D$.[69] This compound, to which the trivial name "texaphyrin" has been assigned, is capable of existing in both its free-base form and of supporting the formation of hydrolytically stable 1:1 complexes with a variety of metal cations, including a number, such as $Cd^{2+}$, $Hg^{2+}$, $In^{3+}$, $Y^{3+}$, $Nd^{3+}$, $Eu^{3+}$, $Sm^{3+}$, and $Gd^{3+}$, that is too large to be accommodated in a stable fashion within the 20% smaller tetradentate binding core of the well-studied porphyrins. In addition, since the free-base form of $5_D$ is a monoanionic ligand, the texaphyrin complexes formed from divalent and trivalent metal cations remain positively charged at neutral pH. As a result, many of these complexes are quite water soluble—at least far more so than the analogous porphyrin complexes.

To date, two X-ray crystal structures of two different $Cd^{2+}$ adducts have been obtained, one of the coordinatively saturated, pentagonal bipyramidal bispyridine complex;[69a] the other of a coordinatively unsaturated pentagonal pyramidal benzimidazole complex.[69b] Importantly, both confirm the planar pentadentate structure of this new ligand system and support the assignment of this prototypical "expanded porphyrin" as aromatic.

Further support for the aromatic formulation comes from the optical properties of $5_D$. For instance, the lowest energy Q-type band of the structurally characterized bispyridine cadmium(II) complex of $5_D$ at 767 nm ($\epsilon=51,900$) in CHCl$_3$ is both considerably more intense (by roughly a factor of 10!) and substantially red shifted (by almost 200 nm!) as compared to that of a typical reference cadmium(II) prophyrin. Of further interest is the fact that compound $5_D$ and both its zinc-(II) and cadmium(II) complexes are very effective photosensitizers for singlet oxygen, giving quantum yields for $^1O_2$ formation of between 60 and 70% when irradiated at 354 nm in air-saturated methanol.[69c] It is these latter remarkable properties which make these systems potentially ideal candidates for use in photodynamic therapy and blood purification protocols.

A variety of new aromatic tripyrroledimethine-derived macrocyclic ligands analogous to compound $5_D$ above now been prepared and more are planned. A number of these, e.g. $10_D$–$15_D$ (see FIG. 25) have already been synthesized and found to form metal complexes as texaphrin $5_D$ and many others can easily be conceived. This aspect of the present invention involves preparation of new analogues of the original texaphrin and elucidation of their chemical and photobiological properties. Of importance is the fact that, by making ostensibly minor substitutions, one may "tune" at will the energy of the lowest Q-type band. For instance in the sequence of cadmium(II) complexes derived from $14_D$, $5_D$ and $16_D$ (which have already been examined), this transition ranges from 690 to 880 nm! Thus, it appears at present, as if the optical properties of the texaphyrin-type expanded porphyrins can be matched to any desired laser frequency. Again, this is a feature that suggests that this class of dyes will be well-suited for a variety of photodynamic applications.

Several preliminary in vitro biological studies have been carried out with the cadmium(II) complexes of the 18 and 22 $\pi$-electron texaphyrins $14_D$ and $5_D$ These results, although limited in scope, are encouraging. For instance, both complexes effect a ca. 2 log photo-killing of HSV-1 infectivity upon irradiation with 20 J/cm$^2$ of light at the lowest energy absorption (690 nm and 767 nm, respectively), yet, importantly, neither $5_D$ nor $14_D$ show any appreciable dark antiviral activity (nor, fortunately, do they show much evidence of general cytotoxicity in the absence of light). In addition, the 22 $\pi$-electron cadmium-containing texaphyrin $5_D$ has been shown by both absorption and emission measurements to localize selectively on lymphocytes. This latter result, in particular, augurs well for the eventual use of these materials in prophylactic photodynamic anti-AIDS blood-treatment programs. The 2 log decrease in HSV-1 activity achieved with the texaphyrin systems studied to date is not yet sufficient to completely design a viable protocol: Both HPD and PII, as well as sapphyrin ($6_D$), reprepared by literature methods[70] provide about a 5 log decrease in viral activity under similar light fluence when irradiated at the appropriate lowest energy transition (630 and 690 nm, respectively). Although a mechanistic comparison with the incompletely characterized hematoporphyrin-derived systems is difficult, a direct structural correspondence exists between the tripyrroledimethine-derived cadmium(II) texaphyrin and free-base sapphyrin systems: The main difference is in overall charge on the photosensitizer. It may thus be that these two macrocycle types are bound to the virus envelope in a different manner; perhaps the sapphyrin "intercalates" into the lipid layer and the charged metallotexaphyrin sits on the surface of the membrane and as such could suffer from deleterious aggregations which would lower singlet oxygen production). The critical observational difference between these two closely related systems (texaphyrin vs. sapphyrin) suggests that small structural differences may be reflected in significant functional effects. In addition, these experimental findings suggest that: 1) The free-base texaphyrin system should be a far more efficient photosensitizer for in vitro and in vivo applications that the cadmium complexes studied so far, and that 2) adjusting the substituents on the texaphyrin periphery should serve to alter the key biodistribution properties of the metalated and metal-free systems. Even if all attempts to augment the photodynamic antiviral efficiency of texaphyrin meet with failure (a result we consider highly unlikely), it is probable that this new photosensitizer will find applications in more classic tumor-treating procedures: The 18 $\pi$-electron cadmium-containing macrocyclic system $14_D$, for instance, has already been shown to effect a roughly 4 log photo-kill of Daudi-strain leukemic cells.

The synthesis of texaphyrin $5_D$ is summarized in FIG. 26. It involved three major steps. The first is the synthesis of the tripyrrane $18_D$. This crucial intermediate is obtained directly as the result of the simple acid-catalyzed condensation between pyrroles $16_D$ and $17_D$. Following deprotection and formylation the key diformyl tripyrrane precursor $20_D$ is obtained in yields exceeding 80% based on $16_D$. Condensation of this tripyrrane with O-phenylenediamine constitutes the second critical step in the synthetic pathway. Fortunately, this reaction proceeds in virtually quantitative yield and gives the sp$^3$ hybridized form of the "texaphyrin" skeleton, $21_D$, directly.[76] The final critical step then involves oxidation and, as appropriate, concurrent metal binding. In the case of Cd$^{2+}$, Hg$^{2+}$, and Zn$^{2+}$, the aromatic, sp$^2$ hybridized, form of the macrocycle (5) is obtained in roughly 25% yield by simply stirring the starting sp$^3$ hybridized precursor (21) with the appropriate salt in the presence of oxygen.[69] Such a simple metal insertion and oxidation procedure, however, fails for cations of the lanthamide series. Here, a combination of metal salt, proton sponge® (N,N',N",N"'-tetramethyl-1,8-diaminonaphthalene), and oxygen are required to effect oxidation and metal insertion. Interestingly, the use of a proton sponge alone gave the free-base form of the ligand directly, but unfortunately in only ca. 10% yield. Efforts to optimize this latter yield are still in progress.

By using a variety of other substituted diamines, it has already proved possible to generate a range of other tripyrroledimethine-derived macrocycles, and it should prove possible to prepare many more by using the appropriate diamine and/or diformyl tripyrrane, to generate the modified texaphyrins $22_D$–$28_D$ shown in FIG. 27. In all cases, the synthesis is expected to be straightforward. In addition to the normal condensation and oxidation steps discussed above, the only new transformations required will involve exposure to basic reagents (i.e. to effect saponification of an ester) under conditions where the macrocyclic skeleton itself is known to be stable. It should also be noted that all of the necessary precursors, with the exception of that required for $27_D$, are either available commercially or already on hand.

A further advantage of developing a wide variety of solubilized texaphyrins is that many of these would be suitable for further functionalization. For instance, treatment of texaphyrins $25_D$ or $26_D$ with thionyl chloride or p-nitrophenol acetate would generate activated acyl species suitable for attachment to monoclonal antibodies or other biomolecules of interest. Alternatively, standard in situ coupling methods (e.g DCCI) could be used to effect the same sort of conjugation. In either case, the ability to attach and deliver a potent photosensitized directly to a tumor locus could have tremendous potential benefit in the treatment of neoplastic disorders.[77]

Figure 28:
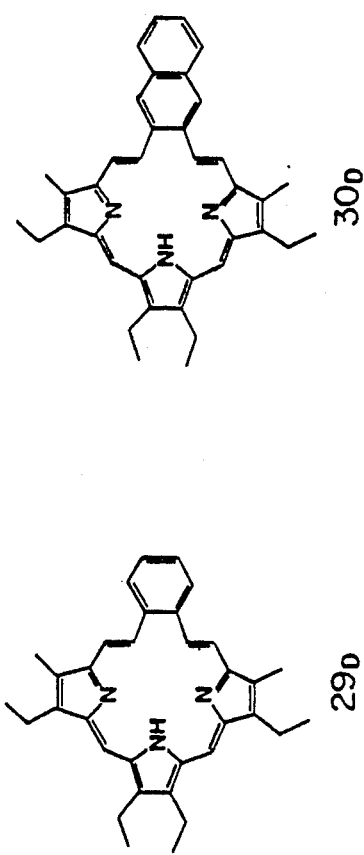
FIG. 28 shows schematic structures of proposed methine-linked texaphyrin derivatives ($29_D$ and $30_D$).

All of the texaphyrin systems prepared to date, and all the new target systems proposed above, involve an imine-containing macrocyclic core. The use of such a linking group offers both advantages and disadvantages. The primary advantage is that macrocyclic systems containing such subunits are easy to prepare and generally act as effective ligands (this is certainly true for texaphyrin!). On the other hand, they are thermodynamically unstable with regards to hydrolysis, although, at least in the case of texaphyrin $5_D$, this is less of a problem than one might expect. For instance, the half-life for imine hydrolysis of the best-studied cadmium-containing complex of $5_D$ is roughly 30 days at pH 7 and several hours at pH 2. Nonetheless, applications could be envisioned where greater stability might be required. For this reason the synthesis of the two methine-linked texaphyrin analogues $29_D$ and $30_D$ in which the weakest CH=N link has been replaced by a more robust CH=CH subunit (See FIG. 28) is an aim of this invention. It is an expectation that compounds $29_D$ and $30_D$ may be prepared using either standard Wittig-based ring closures, which have proved useful in the synthesis of large, furan-containing annulenes,[78] or via McMurry-type couplings, such as those that have recently proved useful in the synthesis of porphycenes.[74]

Once in hand, all new texaphyrin systems will be characterized fully using normal spectroscopic and analytical means, including, where possible X-ray diffraction methods. In addition, a complete analysis of the optical properties will be made for all new systems under a range of experimental conditions including some designed to approximate those which might pertain in vivo. Initial measurements such as simple recording of the optical absorption and emission spectra will be carried out in the P.I.'s laboratory. More detailed analyses, including triplet lifetime and singlet oxygen quantum yield determinations, will be carried out. The objective of this part of the proposed research program is to obtain a complete ground and excited state reactivity profile for each and every new texaphyrin produced. Questions such as when is singlet oxygen production maximized, how is the quantum yield for its formation influenced by the position of the lowest energy (Q-type) transition, whether aggregation is more prevalent in certain solvents or in the presence of certain biologically important components (e.g. lipids, proteins, etc.), and, finally, whether significant differences in in vitro optical properties are derived from the use of elaborated texaphyrins bearing cationic, anionic, or neutral substituents all will be thus answered.

Once the above complexes are made, screening experiments are carried out. Standard in vitro protocols will be used to evaluate the in vitro photo-killing ability of the texaphyrin derivatives in question. For instance, the dyes of choice will be administered in varying concentrations to a variety of cancerous cells and the rate of replication determined both in the presence and absence of light. Similarly, dyes of choice will be added to standard viral cultures and the rate of growth retardation determined in the presence and absence of light. Where appropriate, a variety of solubilizing carriers will be used to augment the solubility and/or monomeric nature of the texaphyrin photosensitizers and the effect, if any, that these carriers have in adjusting the biodistribution properties of the dyes will be assessed (using primarily fluorescence spectroscopy). It should be stressed, of course, that in all cases appropriate control experiments will be carried out with normal cells so that the intrinsic dark and light toxicity of the texaphyrins may be determined.

From a generalized set of in vitro experimental procedures, it is expected that a clear picture of the photodynamic capabilities of the texaphyrin system will emerge. Again, as above, key questions about structure and reactivity will be addressed and answered in what is (hopefully) an unambiguous fashion. In addition, some preliminary toxicity and stability information will begin to emerge from these in vitro experiments. Here questions of interest include how long the texaphyrin system is holding up under physiological conditions and whether the nature of the central metal influences this stability. Equally, or perhaps more important is the question of whether the central cation is affecting cytotoxicity. As discussed in papers published by the present inventors,[69b,69d] it is *not* possible to remove the larger bound cations (e.g. $Cd^{2+}$ or $Gd^{3+}$) by simple chemical means ($Zn^{2+}$, however, appears to "fall out" with ease). Moreover, preliminary results suggest that the best-studied cadmium(II)-containing texaphyrin complex $5_D$ is not appreciable cytotoxic. Nonetheless, the question of intrinsic toxicity is one of such central importance that the cytotoxicity of all new systems will be screened in vitro and, where deemed appropriate, further in vivo toxicity studies will also be carried out.

Once in vitro screening experiments are complete, samples of potential photosensitizers that look particularly promising will be selected for further development. Those that possess the best combination of stability and photodynamic ability for use in blood treatment protocols will be further evaluated in flow system using whole blood samples. Those that look promising for tumor treatment will be subjected to further animal screening.

This aspect of the present invention involves the coordination and photochemical properties of tripyrroledimethine-derived "texaphyrins", a new class of "expanded prophyrins", the first members of which have been recently prepared and characterized in our laboratory. It is expected that these basic studies will lead to the development of viable procedures of removing HIV-1 and other enveloped viruses from transfused blood as well as improved means of detecting and treating tumors. The long range goals exemplified here are to:

1. Synthesize further safe and efficient photosensitizers for use in killing human immunodeficiency virus (HIV-1) and other enveloped viruses in blood, which operate without harm to normal blood components.
2. Develop new safe and effective photosensitizers for use in the in vivo photodynamic treatment of tumors.

The approach to these long range objectives centers around the preparation and use of suitably modified tripyrrole-dimethine derived texaphyrin-type expanded porphyrins. This is an essential first step towards the realization of the above goals. Specific extensions of the present invention include:

1. Explore further the coordination and general chemical properties of our original texaphyrin and existing analogues and obtain a complete solubility, stability, and reactivity profile for those complexes deemed likely to be of greatest biomedical interest.
2. Synthesize simple analogues of the currently available texaphyrins with cationic, anionic, or neutral substituents and study how such modifications alter the water solubility and biodistribution properties of these expanded porphyrins.
3. Make analogues of texaphyrin which contain reactive nucleophilic or electrophilic substituents suitable for conjugation to monoclonal antibodies or other biomolecules of potential interest.
4. Prepare new texaphyrin-type aromatic o macrocycles in which the key imine (CH=N) functionality has been replaced with a presumably more robust methine (CH=CH) linkage.
5. Carry out complete photochemical studies of all new texaphyrins so as to determine unambiguously those factors (e.g. $\lambda_{max}$) which maximize singlet oxygen production.
6. Test the in vitro photodynamic tumor and virus killing efficiency of the new texaphyrins prepared in the course of the synthetic phase of this project.
7. Test the in vivo photodynamic anti-tumor properties of the more promising texaphyrins synthesized and screened as outlined above.

Literature citations in the following list are incorporated by reference herein for the reasons cited.

REFERENCES

1. Confronting AIDS, National Academy of Sciences Press: Washington, D.C., 1988.
2. Dougherty, T. J.; Kaufman, J. E.; Goldfarg, A.; Weishaupt, K. R.; Boyle, D.; Mittleman, A. Cancer Res. 978, 38, 2628.
3. Dahlman, A.; Wile, A. G.; Burns, R. G.; Mason, G. R.; Johnson, F. M.; Berns, M. W. Cancer Res. 1983, 43, 430.
4. Dougherty, T. J. in Methods in Porphyrin Photosensitization, Kessel, D., Ed.; Plenum Press: New York, 1985; pp. 313-328.
5. Dougherty, T. J. Photochem. Photobiol. 1987, 45, 879.
6. See for instance: (a) Figge, F. H. J.; Weiland, G. S. Anat. Rec. 1948, 100, 659; (b) Rasmussen-Taxdall, D. S.; Ward, G. E.; Figge, F. H. Cancer (Phila.) 1955, 8, 78.
7. Berenbaum, M. C.; Bonnett, R.; Scourides, P. A. Br. J. Cancer 1982, 47, 571.
8. Berns, W.; Dahlman, A; Johnson, F. M.; et al. Cancer Res. 1982, 42, 2326.
9. Dougherty, T. J.; Gomer, C. J.; Weishaupt, K. R. Cancer Res. 1976, 36, 2330.
10. Dougherty, T. J. Photochem. Photobiol. 1983, 38, 377.
11. Evensen, J. F.; Sommer, S.; Moan, J.; Chistensen, T. Cancer Res. 1984, 44, 482.
12. Gibson, S. L. Hilf, R. Photochem. Photobiol. 1985, 2, 367.
13. Gomer, C. J.; Smith, D. M. Photochem. Photobiol. 980, 32, 341.
14. Herra-Ornelas, L.; Petrelli, N. J.; Mittleman, A.; Dougherty, T. J.; Boyle, D. G. Cancer, 1986, 57, 677.
15. Kessel, D. Photochem. Photobiol. 1984, 39, 851.
16. Kessel, D. Photochem. Photobiol. 1986, 44, 489.
17. Kessel, D. Int. J. Radiat. Biol. 1986, 49, 901.
18. Klaunig, J. E.; Selman, S. H.; Shulok, J. R.; Schaefer, P. J.; Britton, S. L.; Goldblatt, P. J. Am. J. Path. 1985, 119, 230.
19. Moan, J.; Somer, S. Cancer Lett. 1987, 21, 167.
20. Moan, J.; Peng, Q.; Evensen, J. F.; Berg, K.; Western, A.; Rimington, C. Photochem. Photobiol. 1987, 46, 13.
21. Singh, G.; Jeeves, W. P.; Wilson, B. C.; Jang, D. Photochem. Photobiol. 1987, 46, 645.
22. Bonnett, R.; Ridge, R. J.; Scourides, P. A. J. Chem. Soc., Perkin Trans. I 1981, 3135.
23. Chang, C. K.; Takamura, S.; Musselman, B. D.; Kessel, D. ACS Adv. Chem. Ser. 1986, 321, 347.
24. Dougherty, T. J. Photochem. Photobiol. 1987, 46, 569.
25. Kessel, D. Photochem. Photobiol. 1986, 44, 193.
26. Moan, J.; Christensen, T.; Somer, S. Cancer Lett. 82, 15, 161.
27. Scourides, P. A.; Bohmer, R. M.; Kaye, A. H.; Morstyn, G. Cancer Res. 1987, 47, 3439.
28. Blum, A.; Grossweiner, L. I. Photochem. Photbiol. 85, 41, 27.
29. Henderson, B. W.; Miller, A. C. Radiat. Res. 1986, 8, 196.
30. Keene, J. P.; Kessel, D.; Land, E. J.; Redmond, R. W.; Truscott, T. G. Photochem. Photobiol. 1986, 43, 117.
31. Parker, J. G. Lasers Surg. Med. 1986, 6, 258.
32. Tanielian, C.; Heinrich, G.; Entezami, A. J. Chem. Soc., Chem. Commun. 1988, 1197.
33. Weishaupt, K. R.; Gomer, L. J.; Dougherty, T. J. Cancer Res. 1976, 36, 2326.
34. Gulliya, K. S.; Matthews, J. L.; Fay, J. W.; Dowben, R. M. Life Sciences 1988, 42, 2651.
35. Matthews, J. L.; Newman, J. T.; Sogandares-Bernal, F.; Judy, M. M.; Kiles, H.; Leveson, J. E.; Marengo-Rowe, A. J.; Chanh, T. C. Transfusion, 1988, 28, 81.
36. Skiles, H.; Sogandares-Bernal, F.; Judy, M. M.; Matthews, J. L.; Newman, J. T. Abstracts of 6th Southern Biomedical Engineering Conference, 1987, 83.
37. Skiles, H.; Judy, M. M. Newman, J. T. in Abstracts of the Annual Meeting of the American Society for Microbiology, 85th Annual Meeting, Mar. 3-7, 1985, p. 7, A
38. Lewin, A. A.; Schnipper, L. E.; Crumpacker, C. S. Proc. Soc. Exptl. Biol. Med. 1980, 163, 81.
39. Schnipper, L. E.; Lewin, A. A.; Swartz, M.; Crumpacker, C. S. J. Clin. Invest. 1980, 65, 432.
40. Curran, J. W.; Lawrence, D. N.; Jaffe, H.; et al. N. Engl. J. Med. 1984, 310, 69.
41. Groopman, J. E.; Hartzband, P. I.; Shulman, L.; et al. Blood 1985, 66, 742.
42. Ward, J. W.; Deppe, D. A.; Samson, S.; et al. Ann. Intern. Med. 1987, 106, 61.
43. Ward, J. W.; Holmber, S. D.; Allen, J. R.; et al. N. Engl. J. Med. 1988, 318, 473.
44. Ho, D. D.; Pomerantz, R. J.; Kaplan, J. C. New Engl. J. Med. 1987, 317, 278.
45. Christensen, T.; Sandquist, T.; Feven, K.; Waksvik, H.; Moan, J. Br. J. Cancer 1983, 48, 35.
35. Matthews, J. L.; Newman, J. T.; Sogandares-Bernal, F.; Judy, M. M.; Kiles, H.; Leveson, J. E.; Marengo-Rowe, A. J.; Chanh, T. C. Transfusion, 1988, 28, 81.
36. Skiles, H.; Sogandares-Bernal, F.; Judy, M. M.; Matthews, J. L.; Newman, J. T. Abstracts of 6th Southern Biomedical Engineering Conference, 1987, 83.
37. Skiles, H.; Judy, M. M. Newman, J. T. in Abstracts of the Annual Meeting of the American Society for Microbiology, 85th Annual Meeting, Mar. 3-7, 1985, p. 7, A
38. Lewin, A. A.; Schnipper, L. E.; Crumpacker, C. S. Proc. Soc. Exptl. Biol. Med. 1980, 163, 81.
39. Schnipper, L. E.; Lewin, A. A.; Swartz, M.; Crumpacker, C. S. J. Clin. Invest. 1980, 65, 432.
40. Curran, J. W.; Lawrence, D. N.; Jaffe, H.; et al. N. Engl. J. Med. 1984, 310, 69.
41. Groopman, J. E.; Hartzband, P. I.; Shulman, L.; et al. Blood 1985, 66, 742.
42. Ward, J. W.; Deppe, D. A.; Samson, S.; et al. Ann. Intern. Med. 1987, 106, 61.
43. Ward, J. W.; Holmber, S. D.; Allen, J. R.; et al. N. Engl. J. Med. 1988, 318, 473.
44. Ho, D. D.; Pomerantz, R. J.; Kaplan, J. C. New Engl. J. Med. 1987, 317, 278.
45. Christensen, T.; Sandquist, T.; Feven, K.; Waksvik, H.; Moan, J. Br. J. Cancer 1983, 48, 35.
46. Profio, A. E.; Doiron, D. R. Photochem. Photobiol. 1987, 46, 591.
47. Wan, S.; Parrish, J. A.; Anderson, R. R.; Madden, M. Photochem. Photobiol 1981, 34, 679.
48. Eichler, J.; Knop, J.; Lenz, H. Rad. Environ. Biophys. 1977, 14, 239.
49. Oseroff, A. R.; Ohuoha, D.; Ara, G.; McAuliffe, D.; Foley, Jr.; Cincotta, L. Proc. Natl. Acad. Sci. USA 1986, 83, 9729; and references therein.
50. Gulliya, K. S.; Matthews, J. L. Cell Biol. Int. Rep. 1988, 12, 305; and references therein.

51. Detty, M. R.; Merkel, P. B.; Powers, S. K. J. Am. Chem. Soc. 1988, 110, 5920.

52. Berenbaum, M. C.; Akande, S. L.; Bonnett, R.; Kaur, H.; Ioannou, S.; White, R. D.; Winfield, U.-J. Br. J. Cancer 1986, 54, 717.

53. Kessel, D.; Thompson, P.; Saatio, K.; Nanwi, K. D. Photochem. Photobiol. 1987, 45, 787.

54. Bonnett, R.; McGarvey, D. J.; Harriman, A.; Land, E. J.; Truscott, T. G.; Winfield, U.-J. Photchem. Photobiol. 1988, 48, 271.

55. (a) Morgan, A. R.; Tertel, N. C. J. Org. Chem. 1986, 51, 1347; Morgan, A. R.; Garbo, G. M.; Kreimer-Birnbaum, M.; Keck, R. W.; Chaudhuri, K.; Selman, S. H. Cancer Res. 1987, 47, 496.

56. Morgan, A. R.; Rampersaud, A.; Keck, R. W.; Selman, S. H. Photochem. Photobiol. 1987, 46, 441.

57. Beems, E. M.; Dubbelman, T. M. A. R.; Lugtenburg, J; Van Best, J. A.; Smeets, M. F. M. A.; Boeheim, J. P. J. Photochem. Photobiol. 1987, 46, 639.

58. Cubeddu, R. Keir, W. F.; Ramponi, R.; Truscott, T. G. Photochem. Photobiol. 1987, 46, 633.

59. (a) Kessel, D.; Dutton, C. J. Photochem. Photobiol. 1984, 40, 403; (b) Kessel, D. Cancer Res. 1986, 46, 2248.

60. (a) Dolphin, D. 196th American Chemical Society Meeting, Los Angeles, September 1988, Abstract no. 312; (b) Richter, A. M.; Kelly, B.; Chow, J.; Liu, D. J.; Towers, G. H. N.; Dolphin, D.; Levy, J. G. Cancer Res., in press.

61. (a) Ben-Hur, E.; Rosenthal, I. Inter. J. Radiat. Biol. 1985, 47, 145; (b) Ben-Hur, E.; Rosenthal, I. Photochem. Photobiol. 1985, 42, 129; (c) Ben-Hur, E.; Rosenthal, I. Rad. Res. 1985, 103, 403; (d) Selman, S. H.; Kreimer-Birnbaum, M.; Chaudhuri, K.; Garbo, G. M.; Seaman, D. A.; Keck, R. W.; Ben-Hur, E.; Rosenthal, I. J. Urol. 1986, 136, 141; (e) Ben-Hur, E.; Rosenthal, I. Cancer Lett. 1986, 30, 321; (f) Ben-Hur, E.; Rosenthal, I. Photochem. Photobiol. 1986, 43, 615; (g) Ben-Hur, E.; Green, M.; Prager, A.; Kol, R.; Rosenthal, I. Photochem. Photobiol. 1987, 46, 651.

62. (a) Firey, P. A.; Rodgers, M. A. J. Photochem. Photobiol. 1987, 45, 535; (b) Firey, P. A.; Ford, W. E.; Sounik, J. R.; Kenney, M. E.; Rodgers, M. A. J. J. Am. Chem. Soc. 1988, 110, 7626.

63. (a) Skikes, J. D. Photochem. Photobiol. 1986, 43, 691; (b) Spikes, J. D.; Bommer, J. C. Int. J. Rad. Res. 1986, 50, 41.

64. Brasseur, N.; Ali, H. Autenrieth, D.; Langlois, R.; van Lier, J. E. Photochem. Photobiol. 1985, 42, 515.

65. Bown, S. G.; Tralau, C. J.: Coleridge Smith, P. D.; Akdemir, D.; Wieman, T. V. Br. J. Cancer 1986, 54, 43.

66. Chan, W.-S; Svensen, R.; Phillips, D.; Hart, I. R. Br. J. Cancer 1986, 53, 255.

67. Sonoda, M.; Krishna, C. M.; Riesz, P. Photochem. Photobiol. 1987, 46, 625.

68. For a review see: Sessler, J. L.; Cyr, M.; Murai, T. Comm. Inorg. Chem. 1988, 7, 333.

69. (a) Sessler, J. L.; Murai, T.; Lynch, V.; Cyr, M. J. Am. Chem. Soc. 1988, 110, 5586; (b) Sessler, J. L.; Murai, T.; Lynch, Inorg. Chem. In press; (c) Harriman, T.; Maiya, B. G.; Murai, T.; Hemmi, G.; Sessler, J. L.; Mallouk, T. E. J. Chem. Soc., Chem. Commun., in press; (d) Sessler, J. L.; Murai, T.; Hemmi, G. Inorg. Chem., submitted.

70. Bauer, V. J.; Clive, D. R.; Dolphin, D.; Paine, J. B. III; Harris, F. L.; King, M. M.; Loder, J.; Wang, S.-W. C.; Woodward, R. B. J. Am. Chem. Soc. 1983, 105, 6429.

71. Broadhurst, M. J.; Grigg, R.; Johnson, A. W. J. Chem. Soc. Perkin Trans. 1, 1972, 2111.

72. (a) Berger, R. A.; LeGoff, E. Tetrahedron Lett. 1978, 4225. (b) LeGoff, E.; Weaver, 0. G. J. Org. Chem. 1987, 710.

73. (a) Gosmann, M.; Franck, B. Angew. Chem. 1986, 98, 1107; Angew. Chem. Int. Ed. Eng. 1986, 25, 1100. (b) Knubel, G.; Franck, B. Angew. Chem. 1988, 100, 1203; Angew. Chem. Int. Ed. Eng. 1988, 27, 1170.

74. (a) Vogel, E.; Kocher, M.; Schmickler, H.; Lex, J. Angew. Chem. 1986, 98, 262; Angew. Chem. Int. Ed. Eng. 1986, 25, 257. (b) Vogel, E.; Balci, M.; Pramod, K.; Koch, P.; Lex. J. Ermer, 0. Angew. chem. 1987, 99, 909; Angew. Chem. Int. Ed. Eng. 1987, 26, 928.

75. Aramendia, P. F.; Redmond, R. W.; Nonell, S.; Schuster, W.; Braslavsky, S. E.; Schaffner, K.; Vogel, E. Photochem. Photobiol. 1986, 44, 555.

76. Sessler, J. L.; Johnson, M. R.; Lynch, V. J. Org. Chem. 1987, 52, 4394.

77. For an example of porphyrin-antibody conjugation and a discussion of the relative merits of various coupling methods see, for instance: Mercer-Smith, J. A.; Roberts, J. C; Figard, S. D.; Lavallee, D. K. in "Antibody-Mediated Delivery Systems," Rodwell, J. D.; Ed. Marcel Dekker: New York; 1988, pp. 317–352.

78. Vollhardt, K. P. C. Synthesis 1975, 765.

EXAMPLE 6

One aspect of the utility of the present invention is exemplified by use of complexes described herein for photon-induced deactivation of viruses and virally infected or potentially infected encaryotic cells. The general photodeactivation method used in this example was developed by the Infectious Disease and Advanced Laser Applications Laboratories of the Baylor Research Foundation, Dallas, Tex. and is a subject of a U.S. patent application filed Jun. 25, 1987 by Millard Monroe Judy, James Lester Matthews, Joseph Thomas Newman and Franklin Sogandares-Bernal (assigned to the Baylor Research Foundation, Dallas, Tex.).

The efficiency of some of the porphyrin-like macrocycles in photosensitized inactivation of Herpes Simplex Virus Type 1 (HSV-1) and of human lymphocytes and monocytes, both peripheral mononucleated vascular cells (PMC) and cellular hosts of HIV-1 has been initiated. Previous studies of viral inactivation using the macrocyclic photosensitizers dihematoporphyrin ether (DHE) or hematoporphyrin derivative (HPD) have shown that with the porphyrins, only those viruses studied which are enveloped or possess a membraneous coat are inactivated. The enveloped viruses studied include HSV-1, cytomegalovirus, measles virus[1], and the human immunodeficiency virus HIV-1[2].

The photosensitized inactivation of Herpes Simplex Virus, Type 1 (HSV-1) was investigated in culture medium using various macrocycles of the present invention. Results are listed in Table 4.

TABLE 4

| Herpes Simplex Virus I Inactivation with Assymmetric Expanded Porphyrin Macrocycle Complexes* | | |
|---|---|---|
| Complex** | Conc. (μM) | % Survival Viral Infectivity |
| 3A | 20 | 12 |
|  | 10 | 8 |
|  | 2.5 | 20 |
|  | 0.25 | 100 |

TABLE 4-continued

Herpes Simplex Virus I Inactivation with Assymmetric Expanded Porphyrin Macrocycle Complexes*

| Complex** | Conc. (μM) | % Survival Viral Infectivity |
|---|---|---|
| $10_D$(where M = Cd) | 20 | 4 |
| | 10 | 14 |
| | 2.5 | 42 |
| | 0.25 | 100 |
| $14_D$(where M = Cd) | 16.0 | 3 |
| | 4.0 | 50 |
| | 0.40 | 100 |

Figure 25:
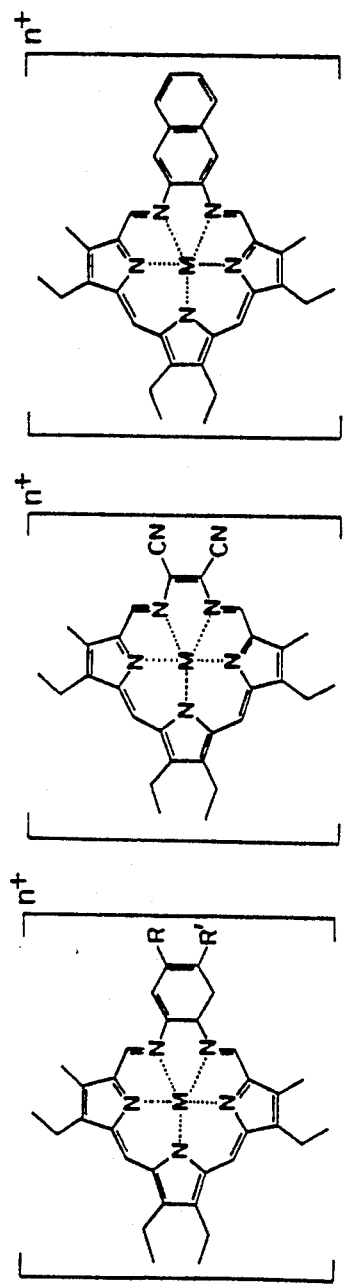
FIG. 25 shows schematic structures of new aromatic tripyrroledimethine-derived macrocyclic ligands ($10_D$-$16_D$) analogous to texaphyrin ($5_D$).

*All light irradiation at λ max absorption and to give a light fluence of 10 J/cm$^2$
**Structural formulas in FIGS. 4 and 25.

The three cadmium-containing macrocycles ($3_A$, $10_D$ (where M is Cd), and $14_D$ (where M is Cd)) at concentrations of 20 μM demonstrated ≧90% viral inactivation as judged by viral plaque assay.

The macrocycle photosensitizing studies employed enveloped HSV-1 as the model for screening based on its ease of propagation and assessment of infectivity in cell culture. The screening procedure for photoinactivation of HSV-1 was similar to the methods previously described.[3] Essentially, selected macrocycles at different concentrations were added to a cell-free suspension of 10$^6$ PFU/ml of HSV-1. The viral suspensions were irradiated at the optimal absorption wavelength of the selected dye at different light-energy densities. Controls consisted of (1) nonirradiated virus, (2) virus irradiated in the absence of macrocycle, and (3) virus treated with selected concentrations of macrocycle and maintained in the dark. All samples were then assessed for viral infectivity by determining the number of PFU/ml in Vero cells.

Viral suspensions were serially diluted and subsequently absorbed onto vero cell monolayers for 1½ hours at 37° C. An overlay medium was added and the cells incubated at 37° C for 3–4 days. The overlay medium was then removed, the monolayers fixed with methanol and tinctured with Giemsa, and individual plaques counted under a dissecting microscope. Uninfected cell cultures also were exposed to the macrocycle complexes to rule out direct cytotoxic effects.

Figure 29:
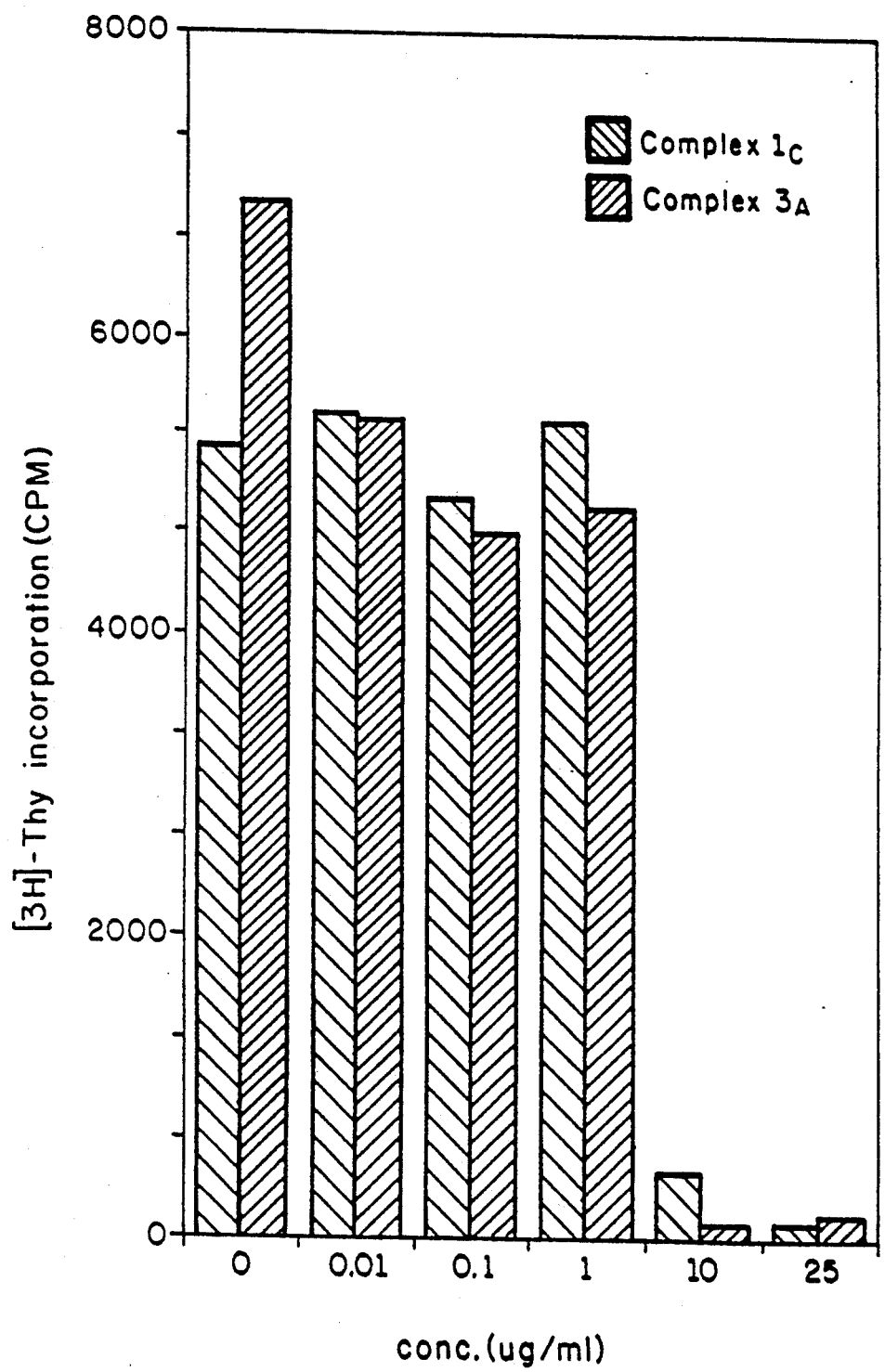
FIG. 29 shows mononuclear cell killing by complexes $1_C$ and $3_A$ without irradiation. Cell kill was determined by [3H]-Thy uptake after phytohemagglutin (PHA) stimulation.
Figure 30:
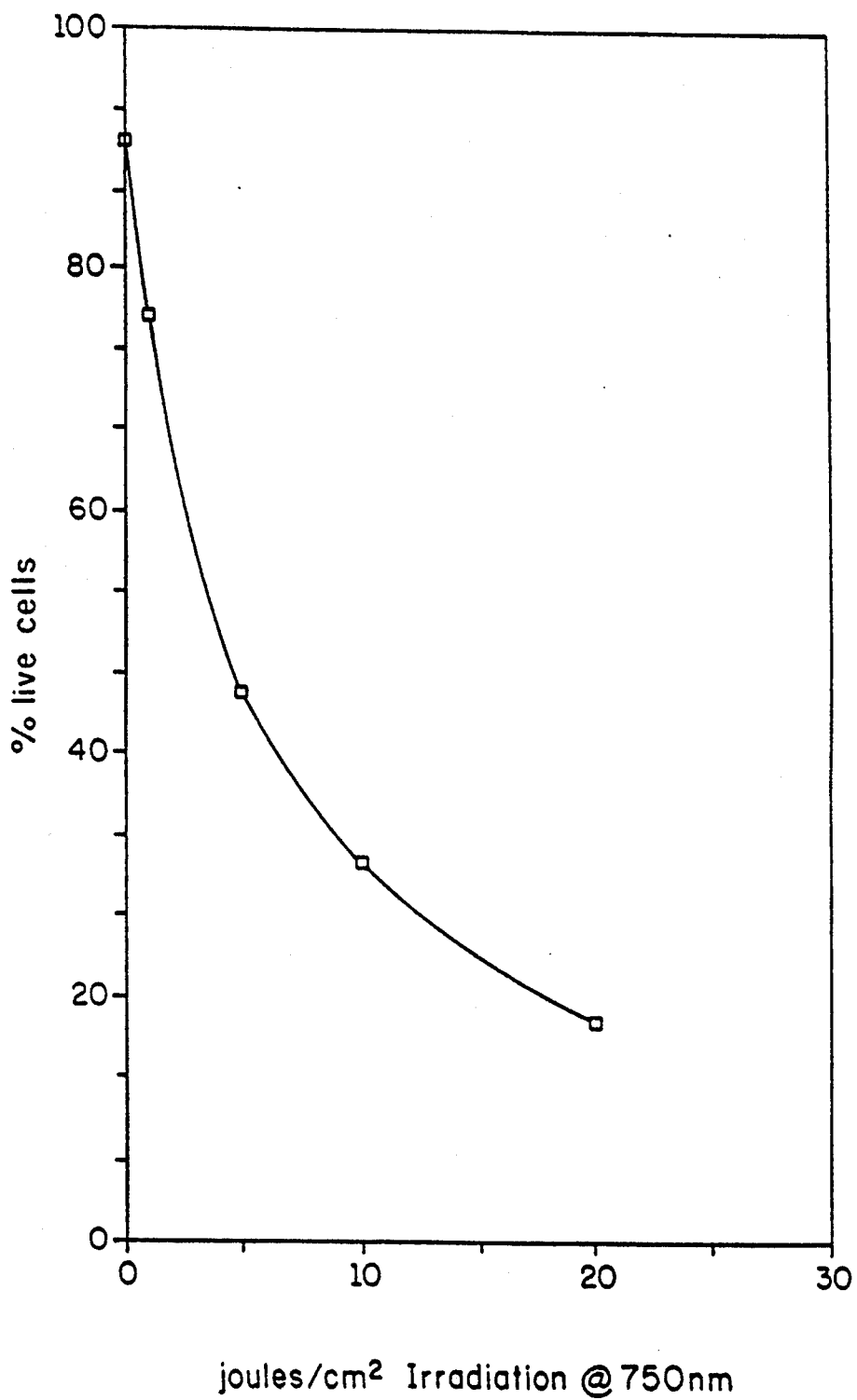
FIG. 30 shows mononuclear cell killing by 1 μg/ml complex $3_A$ and irradiation. Cell kill was determined by [$^3$H]-Thy uptake after PHA stimulation.

The inactivation of PMC's in the absence and presence of light after exposure to concentrations of complex $3_A$ in whole human plasma ranging from 0.015 to 38 μM is shown in FIGS. 29 and 30. Inactivation was judged by mitogenic assay. Toxicity onset with 3A (see FIG. 4) and $1_C$ (see FIG. 17) in the absence of light was between 0.15 and 1.5 μM (FIG. 29). As shown by mitogenic assay in FIG. 30, aerobic photosensitization of cells exposed to $3_A$ at 0.15 μM concentration and 20 joules/cm$^2$ of 770 nm wavelength light caused significant inhibition of the cellular division of PMC's. Moderate increase in either photosensitizer concentration or light dosage is expected to result in essentially complete cellular inactivation.

The results to date, some of which are summarized herein, indicate strongly that the expanded porphyrin-like macrocycles of the present invention should be efficient photosensitizers for free HIV-1 and infected mononuclear cells as well. Altering the polarity and electrical charges of side groups of these macrocycles is anticipated to alter markedly the degree, rate, and perhaps site(s) of binding to free enveloped viruses such as HIV-1 and to virally-infected peripheral mononuclear cells. These substituent changes are also expected to modulate photosensitizer take-up and photosensitization of leukemia or lymphoma cells contaminating bone-marrow as well as by normal cells of the marrow.

References in the following literature incorporated by reference herein for the reasons cited.

REFERENCES

1. Skiles, H. L., Judy, M. M. and Newman, J. T. Abstracts to the Annual Meeting of the ASM, A38, pg. 7, 1985.
2. Matthews, J. L., Newman, J. T., Songandares-Bernal, F., Judy, M. M., Skiles, H., Leveson, J. E., Marengo-Rowe, A. J., and Chanh, T. C. Transfusion, 28:81, 1988.
3. Skiles, H. F., Sogandares-Bernal, F., Judy, M. M., Matthews, J. L. and Newman, J. T. Biomedical Engineering VI: Recent developments. Sixth Southern Biomedical Engineering Conference, 1987.

EXAMPLE 7

This example summarizes certain of the basic five-coordinate (pentadentate), expanded porphyrin compounds and complexes of the present invention and their derivatives which have been synthesized. In FIG. 31, compounds $1_E$–$7_E$, $14_D$ and $15_D$ are shown. Variations include changes in the ortho-phenylene-diamino substituent, namely $R_1$ and $R_2$ and in the nature of the starting diamine itself. When both $R^1$ and $R^2$ on the ortho phenylene diamino substitutent are hydrogen as in compound $1_E$ the basic structure of texaphyrin is shown. These $R^1$ and $R^2$ substituents may also both be methyl, $CH_3$ (compound $2_E$). Additionally when $R^1$ is H, $R^2$ may be chloride (compound $3_E$); bromine (compound $4_E$); nitro (compound $5_E$); methoxy (compound $6_E$); or carboxy (compound $7_E$). When M is hydrogen, the complex has a charge of 0 (n=0). When M is a divalent metal such as mercury$^{+2}$, cadmium$^{+2}$, zinc$^{+2}$, cobalt$^{+2}$ or manganese$^{+2}$; the charge of the complex will be +1 (n=1). When M is a trivalent metal cation such as europium$^{+3}$, neodynium$^{+3}$, samarium$^{+3}$, lanthanum$^{+3}$, gadolinium$^{+3}$, indium$^{+3}$ or yttrium$^{+3}$ the charge of the complex will be +2 (n=2). For the complexes marked with a single asterisk ($1_E$ and $2_E$) all metals, divalent or trivalent mentioned above have been included in various formed complexes. Complexes with a double asterisk ($3_E$–$6_E$) have been synthesized as either the zinc or cadmium derivative. (M=Zn or Cd; n=1). While many other usable compounds are mentioned in other sections of this application, or could be readily synthesized by those of skill in the art from the directions included herein, the particular ones mentioned in this Example are thought to be especially useful for many purposes, for example, those involving purifying biological samples of viruses, particularly retroviruses. These compounds should also be useful for processes such as, for example, photodynamic cancer therapy, magnetic resonance imaging (MRI) enhancement and antibody functionalization as mentioned elsewhere herein.

EXAMPLE 8

Magnetic Resonance Imaging Enhancement

In many respects the key to cancer control lies as much, if not more, in early detection and diagnosis as it does in subsequent therapeutic management. New techniques which allow neoplastic tissue to be observed and recognized at an early stage of development thus have a critical role to play in the battle against these disorders. One such promising technique is magnetic resonance imaging (MRI).[1-5] Although quite new, this noninvasive, apparently innocuous method, is not firmly entrenched as a diagnostic tool of prime importance, complementing or, in some cases, supplanting computer assisted X-ray tomography as the method of choice for solid tumor detection.

The physical basis of current MRI methods has its origin in the fact that in a strong magnetic field the nuclear spins of water protons in different tissues relax back to equilibrium at different rates, when subject to perturbation from the resting Boltzman distribution by the application of a short rf pulse.[2,5] For the most common type of spin-echo imaging, return to equilibrium takes place in accord with equation 1 and is governed by two time constants $T_1$ and $T_2$, the longitudinal and transverse relaxation times, respectively.

$$SI = [H]H(v)\{exp(-T_E/T_2)\}\{1 - exp(-T_R/T_1)\} \quad (1)$$

Here, SI represents the signal intensity, [H] is the concentration of water protons in some arbitrary volume element (termed a voxel), $H(v)$ a motion factor corresponding to motion (if any) in and out of this volume element, and $T_E$ and $T_R$ are the echo-delay time and the pulse-repetition times, respectively. The various pulse sequences associated with obtaining an MRI image thus correspond to choosing $T_E$ and $T_R$ by setting the times associated with (and between) the excitation and interrogation rf pulses (the first to perturb the system, the second to determine the extent of return to equilibrium) and determining SI, which, as illustrated above, is function of the particular $T_1$ and $T_2$ values in force. Since both $T_1$ and $T_2$ are a function of the local (bulk) magnetic environment, and as such are a function of the particular tissue in which the water proton is situated, differences in these values (and hence SI) allow for image reconstruction. Of course, only when these local, tissue-dependent, relaxation differences are large can tissue differentiation be effected.

In practice for biological systems, $T_2$ values are very short (and $T_E$ and $T_R$ are chosen to accentuate this situation). Thus it is differences in the longitudinal time constant ($T_1$) which dominate relaxation effects and relative signal intensity: Decreases in $T_1$ correspond to increasing signal intensity. Any factors, therefore, which will serve to decrease $T_1$ selectively for a particular tissue or organ will thus lead to increased intensity for that area and better contrast (signal to noise) relative to the bulk animal background. This is where paramagnetic MRI contrast agents come into play.[4,5]

It has been known since the earliest days of magnetic resonance spectroscopy that paramagnetic compounds, containing one or more unpaired spins, enhance the relaxation rates for the water protons in which they are dissolved.[6] The extent of this enhancement, termed relaxivity, is, in the absence of colligative interactions, given by $R_i$ (in units of $M^{-1}s^{-1}$ or $mM^{-1}s^{-1}$) in eq.2. [4,5]

$$(1/T_i)_{obsd} = (1/T_i)_d + R_i[M] \quad i=1,2 \quad (2)$$

Here, $(1/T_i)_{obsd}$ is the reciprocal of the observed relaxation time in the presence of a paramagnetic species M, and $(1/T_i)_d$ is the observed relaxations time in its absence. The relaxivity of any given paramagnetic species, i.e., metal complexes for MRI enhancement, is dependent on the magnitude of the dipole-dipole interactions between the electron spin (on the metal) and the proton spin (on the water). The extent of this interaction is strongly dependent on the nature of the interaction between the paramagnetic complex and the water molecule in question. Traditionally, it has proved convenient to define both "inner sphere" and "outer sphere" contributions to the total relaxivity $R_i$.[4,5] The former account for water molecules which participate directly in the coordination sphere of the metal; the latter for all other loose interactions (e.g. hydrogen bonding and translational diffusion of waters bound in the second coordination sphere). Where chemically viable, it is, in general, inner sphere relaxation which dominates $R^i$. For this interaction, the contribution to the longitudinal relaxation is given by equation 3.[4,5]

$$(1/T_1)_{(inner\ sphere)} = P_M \cdot q/T_{1M} + \tau_M \quad (3)$$

Here, $P_M$ is the mole fraction of metal ion, q is the number of bound water molecules, $\tau_M$ is the lifetime of the bound water, and $T_{1M}$ is the relaxation time of the bound water protons. The value of this latter term is approximated by the Solomon-Bloembergen equations (eqs. 4-6) which account for both dipole-dipole ("through space") and contact ("through-bond") terms.[7]

$$\frac{1}{T_{1M}} = \frac{2}{15} \frac{\gamma_I^2 g^2 S(S+1)\beta^2}{r^6} \frac{7\tau_c}{(1 = \omega_s^2 \tau_c^2)} +$$

$$\frac{3\tau_c}{(1 = \omega_I^2 \tau_c^2)} + (2/3)S(S+1)[A2\pi/h]^2 \frac{\tau_e}{(1 + \omega_s^2 \tau_c^2)}$$

Here, $\gamma_I$ is the proton gyromagnetic ratio, g the electronic g-factor, S the total electron spin of the paramagnetic ion, $\beta$ the Bohr magneton, r the water proton-metal ion distance, $[A2\pi/h]$ the electron-nuclear hyperfine coupling constant, and $\omega_s$ and $\omega_I$ the electronic and proton Larmor precession frequencies, respectively. The dipolar and scaler correlation times $\tau_c$ and $\tau_e$ are given by:

$$1/\tau_c = 1/T_{1e} + 1/\tau_M + 1/\tau_R \quad (5)$$

$$1/\tau_e = 1/T_{1e} + 1/\tau_M \quad (6)$$

where, $T_{1e}$ is the longitudinal electron spin relaxation time and $\tau_R$ the rotational tumbling time of the entire water-complex ensemble. More elaborate theoretical treatments are available to account for collisional relaxation effects and other factors which would perturb the static zero-field splitting of the electronic sublevels in inner sphere relaxation pathways.[5] Detailed analyses are also available to account for contributions from outer sphere mechanisms.[5] Nonetheless, for the sake of the present discussion, the simple Solomon-Bloembergen equations given above will suffice: They illustrate the key physical features required for a good paramagnetic contrast agent.

From a physical point of view, MRI contrast agents require species that are highly paramagnetic (so that the magnetic moment term $S(S+1)$ is large), possess large $T_{1e}$'s, and display large rotational tumbling times ($\tau_R$) In addition, an ideal contrast agent should also bind one or more water molecules (so that the inner sphere relaxation mechanisms are operative) and exchange these waters at a rate ($1/\tau_M$) that is optimal.[4,5,8,9] with the exception of $\tau_R$, which is often set more by the effective viscosity of the local environment (i.e. is the complex "stuck" to a slowly rotating protein?[10]) than by the choice of complex, all of these factors may be influenced by the choice of basic paramagnetic cation and by subsequent ligand design.[4,5,9] This ligand design, which constitutes a major thrust in current MRI research, is, of course, also subject to very stringent biological requirements: Not only must the putative contrast agent be highly paramagnetic and achieve good relaxation enhancement, it must also be nontoxic at the dosages administered, stable in vivo, excreted quickly after diagnosis is complete, and, of course, show desirable tissue localizing abilities. Taken together these criteria are quite severe.

Indeed, at present, only one paramagnetic MRI contrast agent is in clinical use, the bis(N-methyl-glucamine) salt of Gd(III) diethylenetriaminepentaacetate, $(MEG)_2[Gd(DTPA)(H_2O)]$ (c.f. structure 10)[11-18] marketed by Berlex Laboratories. This dianionic complex localizes selectively in extracellular regions, and is being used primarily in the visualization of the capillary lesions associated with cerebral tumors.[11-13] In $[Gd(DTPA)(H_2O)]^{2-}$, one molecule of water is bound in the first (inner) coordination sphere and at 37° C. in water this complex displays a relaxivity of 3.7 mM-$^1$s-$^1$ at 20 MHz.[4,9,19] In marked contrast to the simple Gd(III) complex of EDTA, for which log $K_{assc.}$=17.4 at 25° C.,[20,21] the DTPA complex appears to be sufficiently thermodynamically stable (log $K_{assc.}$=22.5 at 25° C.[20,21] so as to be kinetically stable under physiological conditions nd is apparently excreted intact through the kidneys within several days of administration.[14] These desirable features notwithstanding, it is clear that other contrast agents with superior kinetic stability, better relaxivity, lower net charge (which would lower the osmolality and hence pain threshold of the administered solutions), and/or different tissue localizing capabilities would be desirable for clinical use. Indeed, in a recent review on the subject,[5] Lauffer states that: "New synthetic methods toward kinetically inert complexes, especially those of Gd(III), need to be developed. These preferably should be versatile enough to allow for specific substitutions on the complex that may modulate its properties."

To date, in fact, considerable effort has been devoted to the development of new potential MRI contrast agents.[21-37] Most of this work has centered around preparing new complexes of Gd(III).[21-29,362,376] The emphasis on Gd(III) salts stems from the fact that this cation, with 7 unpaired f-electrons, has a higher magnetic moment than other paramagnetic cations such as Fe(III) and Mn(II).[4,5] Thus, all other things being equal, complexes of Gd(III) would be expected to be superior relaxation agents than those derived from Mn(II) or Fe(III). In addition, both iron and, to a lesser extent, manganese are sequestered and stored very efficiently in humans (and many other organisms) by a variety of specialized metal-binding systems.[38] Moreover both iron and manganese are capable of existing in a range of oxidation states and are known to catalyze a variety of deleterious Fenton-type free-radical reactions.[30] Gadolinium(III), which suffers from neither of these deficiencies thus appears to offer many advantages. Unfortunately, as is true for Fe(III) and Mn(II), the aqueous solution of Gd(III) is too toxic to be used directly MRI imaging at the 0.01 to 1 mM concentrations required for effective enhancement.[4,5] Hence the emphasis is on developing new agents which, as is true for DTPA, form hydrolytically stable complexes in vivo with Gd(III) and/or other paramagnetic cations. A number of such ligands, including the very promising DOTA[21-27] and EHPG[28,29] systems, are now known (c.f. reference 5 for an extensive review). In almost all cases, however, reliance is made on the same basic philosophical approach. Specifically, for Gd(III) binding, carboxylates, phenolates, and/or other anionic chelating groups are being used to generate intrinsically labile complexes of high thermodynamic stability in the hope that such high thermodynamic stability will translate into a kinetic stability that is sufficient for in vivo applications. Indeed, little effort is currently being devoted to the preparation of nonlabile Gd(III) complexes that would in and of themselves enjoy a high kinetic stability. The problem seems to be quite simply that such systems are hard to make. For instance, unlike the transition metal cations which are bound well to porphyrins (a synthetically versatile ligand which is readily subject to modification and which, at least for $[Mn(III)TPPS]^{3-}$, and other water soluble analogues,[30-34] shows good relaxivity and good tumor localizing properties), Gd(III) forms only weak and/or hydrolytically unstable complexes with porphyrins,[30c,34,40] although other simple macrocyclic amine- and imine-derived ligands[36,37,41] will support stable complexes with certain members of the lanthanide series and do show some promise, as yet unrealized, of acting as supporting chelands for Gd(III)-based MRI applications. It is a premise of the present invention that nonlabile porphyrin-like Gd(III) complexes can be generated using an "expanded porphyrin" approach and that once made these complexes will prove to be useful contrast agents for MRI applications. In fact, texaphyrin is capable of stabilizing complexes with a variety of di- and trivalent cations, including $Cd^{2+}$, $Hg^{2+}$, $Y^{3+}$, $In^{3+}$, and $Nd^{3+}$. The observation that a hydrolytically stable $Nd^{3+}$ complex may be supported by texaphyrin bodes well for the use of texaphyrins in various gadolinium(III)-based MRI applications. Unfortunately, as explained in greater detail in Example 4, all efforts to date to isolate a stable $Gd^{3+}$ complex from texaphyrin in good yield in good yield have met with failure. It is suspected that this is because the complex is actually so water soluble that standard work-up methods fail. Consistent with this supposition is the fact that fully characterized $Sm^{3+}$, $Eu^{3+}$, and $Gd^{3+}$ (as well as $Y^{3+}$) complexes have been prepared from the more hydrophobic dimethyl-texaphyrin. These complexes are obtained in roughly 25% yields from the corresponding reduced (methylene bridged) macrocyclic precursor using the standard metal insertion and oxidation conditions discussed below and in Examples 1 and 2. Importantly, all of these complexes are soluble in 1:1 methanol-water mixtures and all are quite stable under such potentially decomplexing conditions. The half-life of the $Gd^{3+}$ complex in 1:1 methanol-water at room temperature, for instance, is over 5 weeks. Thus it is possible to use a texaphyrin-type approach to generate hydrolytically stable gadolinium(III) complexes (something that cannot be achieved using simple porphyrins.[40] Given this critical result, further modifications of the texaphyrin skeleton which should allow preparation of stable $Gd^{3+}$ complexes with improved water solubility or better biodistribution properties. In addition, by using suitable anionic side-chains, it should be possible to prepare neutral complexes with no net overall charge. Such complexes would display a lower osmolality in aqueous solution. This would reduce the pain associated with their administration and have positive clinical consequences. Thus the texaphyrin approach to MRI use of contrast agent development looks promising.

Literature citations in the following list are incorporated by reference herein for the reasons cited.

REFERENCES

1. For an historical overview see: Budinger, T. F.; Lauterbur, P. C. Science 1984, 226, 288.
2. Morris, P. G. Nuclear Magnetic Resonance Imaging in Medicine and Biology, Claredon Press: Oxford; 1986.
3. For a review of biological applications of NMR see: MacKenzie, N. E.; Gooley, P. R. Med. Res. Rev. 1988, 8, 57.
4. For an introductory discussion of MRI contrast agents see: Tweedle, M. F.; Brittain, H. G.; Eckelman, W. C.; Gaughan, G. T.; Hagan, J. J.; Wedeking, P. W.; Runge, V. M. in Magnetic Resonance Imaging, 2nd ed., Partain, C. L., et al. Eds.; W. B. Saunders: Philadelphia; 1988, Vol. I, pp. 793-809.
5. For a comprehensive review of paramagnetic MRI contrast agents see: Lauffer, R. B. Chem. Rev. 1987, 87, 901.
6. Bloch, F. Phys. Rev. 1946, 70, 460.
7. (a) Bloembergen, N; Purcell, E. M.; Pound, E. V. Phys. Rev. 1948, 73, 679. (b) Solomon, I. Phys. Rev. 1955, 99, 559.
8. (a) Koenig, S. H.; Brown, R. D. III Magn. Res. Med. 1984, I, 437. (b) Koenig, S. H.; Brown, R. D. III Magn. Res. Med. 1984, 1, 478. (c) Koenig, S. H.; Brown, R. D. III Magn. Res. Med. 1985, 2, 159.
9. Tweedle, M. F.; Gaughan, G. T.; Hagan, J; Wedeking, P. W.; Sibley, P.; Wilson, L. J.; Lee, D. W. Nucl. Med. Biol. 1988, 15, 31.
10. Burton, D. R.; Forsen S.; Karlstrom, G; Dwek, R. A. Prog. NMR Sprectr. 1979, 13, 1.
11. Carr, F. H.; Brown, J; Bydder, G. M.; et al. Lancet 1984, 1, 484.
12. (a) Weinmann, H.-J.; Brasch, R. C.; Press, W. R.; Wesby, G. Am. J. Roentg. 1984, 142, 619. (b) Brasch, R. C.; Weinmann, H.-J.; Wesbey, G. E. Am J. Roentg. 1984, 142, 625.
13. (a) Runge, V. M.; Schoerner, W.; Niendorf, H. P.; et al. Mag. Res. Imaging 1985, 3, 27. (b) Runge, V. M.; Price, A. C.; Alleng, James, A. E. Radiology, 1985, 157(P), 37.
14. Koenig, S. H.; Spiller, M.; Brown, R. D. III; Wolf, G. L. Invest. Radiology 1986, 21, 697.
15. Johnston, D. L.; Lieu, p.; Lauffer, R. B.; Newell, J. B.; Wedeen, V. J.; Rosen, B. R.; Brady, T. J.; Okada, R. D. J. Nucl. Med. 1987, 28, 871.
16. Schmiedl, U.; Ogan, M.; Paajanen, H.; Marotti, M. Crooks, L. E.; Brito, A. C.; Brasch, R. C. Radiology 1987, 162, 205.
17. Kornguth, S. E.; Turski, P. A.; Perman, W. H.; Schultz, R.; Kalinke, T.; Reale, R.; Raybaud, F. J. Neurosug. 1987, 66, 898.
18. (a) Lauffer, R. B.; Brady, T. J. Magn. Reson. Imaging 1985, 3, 11(b) Lauffer, R. B.; Brady, T. J.; Brown, R. D.; Baglin, C.; Koenig, S. H. Magn. Reson. Med. 1986, 3, 541.
19. Southwood-Jones, R. V.; Earl, W. L.; Newman, K. E.; Merbach, A. E. J. Chem. Phys. 1980, 73, 5909.
20. Martell, A. E.; Smith, R. M. Critical Stability Constants, Plenum: New York; 1974, Vol. 4.
21. Cacheris, W. P.; Nickle, S. K.; Sherry, A. D. Inorg. Chem. 1987, 26, 958.
22. Desreaux, J. F.; Loncin, M. F.; Spirlet, M. R. Inorg. Chim. Acta 1984, 94, 43.
23. Chu, S. C.; Pike, M. M., Fossel, E. T.; Smith, T. W.; Balschi, J. A.; Springer, C. S., Jr. J. Man. Reson. 1984, 56, 33.
24. (a) Spirlet, M.-R.; Rebizant, J.; Desreaux, J. F.; Loncin, M. F. Inorg. Chem. 1984, 23, 359. (b) Spirlet, M.-R.; Rebizant, J.; Loncin, M. F.; Desreux, J. F. Inorg. Chem. 1984, 23, 4278.
25. Loncin, M. F.; Desreaux, J. F.; Merciny, E.; Inorg. Chem. 1986, 25, 2646.
26. (a) Chang, C. A.; Rowland, M. E. Inorg. Chem. 1983, 22, 3866. (b) Chang, C. A.; Ochaya, V. O. Inorg. Chem. 1986, 25, 355. (c) Chang, C. A.; Sekhar, V. C. Inorg. Chem. 1987, 26, 1981.
27. Geraldes, C. F. G. C.; Sherry, A. D.; Brown, R. D. III; Koenig, S. H.; Magn. Reson. Med. 1986, 3, 242.
28. Lauffer, R. B.; Greif, W. L.; Stark, D. D.; Vincent, A. C.; Saini, S.; Wedeen, V. J.; Brady, T. J. J. Comput. Assist. Tomogr. 1985, 9, 431.
29. Lauffer, R. B.; Vincent, A. C.; Padmanabhan, S.; Meade, T. J. J. Am. Chem. Soc. 1987, 109, 2216.
30. (a) Chen, C.; Cohen, J. S.; Myers, C. E.; Sohn, M. FEBS Lett. 1984, 168, 70. (b) Patronas, N. J.; Cohen, J. S.; Knop, R. H.; Dwyer, A. J.; Colcher, D.; Lundy, J.; Mornex, F.; Hambright, P. Cancer Treat. Rep. 1986, 70, 391. (c) Lyon, R. C.; Faustino, P. J.; Cohen, J. S.; Katz, A.; Mornex, F.; Colcher, D.; Baglin, C.; Koenig, S. H.; Hambright, P. Magn. Reson. Med. 1987, 4, 24. (d) Megnin, F.; Faustino, P. J.; Lyon, R. C.; Lelkes, P. I.; Cohen, J. S. Biochim. Biophys. Acta 1987, 929, 173.
31. Jackson, L. S.; Nelson, J. A.; Case, T. A.; Burnham, B. F. Invest. Radiology 1985, 20, 226.
32. Fiel, R. J.; Button, T. M.; Gilani, S.; et al. Magn. Reson. Imaging 1987, 5, 149.
33. Koenig, S. H.; Brown, R. D. III; Spiller, M. Magn. Reson. Med. 1987, 4, 252.
34. Hambright, p.; Adams, C.; Vernon, K. Inorg. Chem. 1988, 27, 1660.
35. Smith, P. H.; Raymond, K. N. Inorg. Chem. 1985, 24, 3469.
36. For examples of lanthanide cryptates see: (a) Gansow, O. A.; Kauser, A. R.; Triplett, K. M.; Weaver, M. J.; Yee, E. L. J. Am. Chem. Soc. 1977, 99, 7087. (b) Yee, E. L.; Gansow, O. A.; Weaver, M. J. J. Am. Chem. Soc. 1980, 102, 2278. (c) Sabbatini, N.; Dellonte, S.; Ciano, M.; Bonazzi, A.; Balzani; V. Chem. Phys. Let. 1984, 107, 212. (d) Sabbatini, N.; Dellont, S.; Blasse, G. Chem. Phys. Lett. 1986, 129, 541. (e) Desreux, J. F.; Barthelemy, P. P. Nucl. Med. Biol. 1988, 15, 9.
37. For examples of lanthanide complexes stabilized by conventional Schiff base macrocycles see: (a) Backer-Dirks, J. D. J.; Gray, C. J.; Hart, F. A.; Hursthouse, M. B.; Schoop, B. C. J. Chem. Soc., Chem. Commun. 1979, 774. (b) De Cola, L.; Smailes, D. L.; Vallarino, L. M. Inorg. Chem. 1986, 25, 1729. (c) Sabbatini, N.; De Cola, L.; Vallarino, L. M.; Blasse, G. J. Phys. Chem. 1987, 91, 4681. (d) Abid, K. K.; Fenton, D. E.; Casellato, U.; Vigato, P.; Graziani, R. J. Chem. Soc., Dalton Trans. 1984, 351. [e] Abid, K. K.; Fenton, D. E. Inorg. Chim. Acta 1984, 95, 119-125. (f) Sakamoto, M. Bull Chem. Soc. Jpn. 1987, 60, 1546.
38. Ochai, E.-I Bioinorganic Chemistry, an Introduction, Allyn and Bacon: Boston; 1977, p. 168(Fe) and p 436(Mn).
39. For reviews see: (a) Cytochrome P-450: Structure, Mechanism, and Biochemistry, Ortiz de Montellano, P. R., Ed.; Plenum: New York, 1986. (b) Groves, J. T. Adv. Inorg. Biochem. 1979, 1, 119.

40. (a) Buchler, J. W. in The Porphyrins, Dolphin, D.Ed., Academic Press: New York; 1978, Vol. 1, Chapter 10. (b) Srivastava, T. S. Bioinorg. Chem. 1978, 8, 61. (c) Horrocks, W. DeW., Jr. J. Am. Chem. Soc. 1978, 100, 4386.

41. (a) Forsberg, J. H. Coord. Chem. Rev. 1973, 10, 195. (b) Bunzli, J.-C.; Wesner, D. Coord. Chem. Rev. 1984, 60, 191.

EXAMPLE 9

Antibody Conjugates

Radioisotopes have long played a central role in the detection and treatment of neoplastic disorders. Considerable research therefore continues to be devoted to improving their efficacy in medical applications. One of the more promising approaches in doing so involves attaching radioisotopes to tumor-directed monoclonal antibodies and their fragments. Such monoclonal antibodies and their fragments localize selectively at tumors; radiolabeled antibodies could therefore serve as "magic bullets" and allow the direct transport of radioisotopes to neoplastic sites thus minimizing whole body exposure to radiation.[1] Considerable research is now being carried out along these lines (see references 2-11 for general reviews). Much, but certainly not all, is focusing on the use of bifunctional metal chelating agents. It is this approach to radioimmunodiagnostics (RID) and therapy (RIT) that is most closely related to the present invention.

Bifunctional metal chelating agents for use in antibody conjugate-based treatment and diagnostic applications must satisfy two critical criteria: They must be capable of binding the radioisotope of interest and of attachment to the targeted antibody. Thus, these bifunctional chelating agents must 1) have functional groups suitable for conjugation to the antibody, 2) form covalent linkages that are stable in vivo and which do not destroy the immunological competence of the antibody, 3) be relatively nontoxic, and 4) bind and retain the radiometal of interest under physiological conditions.[11-15] The last of these conditions is particularly severe. In contrast to MRI imaging where small concentrations of decomplexed cation can perhaps be tolerated, the potential damage arising from "free" radioisotopes, released from the conjugate, can be very serious. Thus, for radioimmunological work, the condition of nonlability must be strictly enforced. On the other hand, only nanomole concentrations of isotopes, and hence ligand, are generally required for RID and RIT applications, so that the concerns associated with intrinsic metal and/or free ligand toxicity are considerably relaxed.

Needless to say, the above conditions must be met for each and every isotope considered for RIT and RID work. Thus, from the point of view of ligand design and synthesis, the problem becomes one of identifying an isotope of medical advantage, designing a suitable ligand and attaching it to the antibody of choice either before or after metal binding. Historically, there has been a trade-off between choosing an ideal isotope and one that can be readily complexed with existing difunctional conjugates.

For the purposes of imaging, an ideal isotope should be readily detectable by available monitoring techniques and induce a minimal radiation-based toxic response. In practice these and other necessary requirements implicate the use of a γ-ray emitter in the 100 to 250 KeV range, which possesses a short effective half-life (biological and/or nuclear), decays to stable products, and, of course, is readily available under clinical conditions.[2-4] To date, therefore, most attention has focused on $^{131}$I ($t_{\frac{1}{2}}=193$h), $^{123}$I ($t_{\frac{1}{2}}=13$H), $^{99m}$Tc($t_{\frac{1}{2}}=6.0$ h), $^{67}$Ga($t_{\frac{1}{2}}=78$h), and $^{111}$In($t_{\frac{1}{2}}=67.4$h) which come closest to meeting these criteria.[16] Each of these enjoys advantages and disadvantages with respect to antibody labeling for RID. $^{131}$I and $^{123}$I, for instance, are easily conjugated to antibodies (and other proteins) via simple electrophilic aromatic substitution of tyrosine residues.[17] As a result, these isotopes have seen wide use in immunological-based applications (RIT as well as RID). Unfortunately, such methods of conjugation are not particularly robust under physiological conditions (metabolism of $^{131}$I or $^{123}$I labeled proteins, for instance, produces free radioactive iodide anion) and as a result can lead to a fair concentration of radioactivity at sites other than those targeted by the antibody-derived "magic bullet".[17] This problem is further exacerbated by the fact that the half-lives of both $^{131}$I and $^{123}$I are relatively inconvenient for optimal use, being too long and too short, respectively, and the fact that $^{131}$I is also a β emitter.[16] $^{99m}$Tc, $^{67}$Ga, and $^{111}$In all suffer from the disadvantage that they cannot be bound directly to the antibody in a satisfactory fashion and require the use of a bifunctional conjugate. The chemistry of such systems is furthest advanced in the case of $^{99m}$Tc, and a number of effective ligands, are now available for the purpose of $^{99m}$Tc administration.[2-12,18] This particular radioisotope, however, suffers from the serious disadvantage of having a very short half-life which makes it technically very difficult to work with. Both $^{67}$Ga and $^{111}$In have longer half-lives. In addition, both possess desirable emission energies. Unfortunately, both are "hard" cations with high charge density in their most common trivalent forms. Applications of these radioisotopes in RID therefore requires the use of ligands which are capable of forming stable, nonlabile complexes with these cations under physiological conditions. Although considerable effort has been devoted to the development of DTPA-like systems[19] which would be suitable for $^{111}$In$^{3+}$ (and, perhaps, $^{67}$Ga$^{3+}$) binding and antibody functionalization, in all cases the complexes formed are too labile for safe and effective clinical use.[20] Indeed, at the present time, no suitable ligands exist for either $^{111}$In$^{3+}$ or $^{67}$Ga$^{3+}$ which form stable nonlabile complexes and which might be suitable for radioimmunological applications. As described elsewhere herein texaphyrin forms a kinetically and hydrolytically stable complex with In$^{3+}$. Such a ligand system could be elaborated and serve as the critical core of a bifunctional conjugate for use in $^{111}$In-based RID.

Many of the same considerations hold true for radioisotope-based therapy as do for radioisotope-based diagnostics: An ideal isotope must also be readily available under clinical conditions (i.e. from a simple decay-based generator),[2] possess a reasonable half-life (i.e. on the order of 6 hours to 4 weeks), and decay to stable products. In addition, the radioisotope must provide good ionizing radiation (i.e. in the 300 KeV to 3 MeV range). In practice this means using either an α emitter or medium to high energy β emitter.[16] Although few α emitters are available for therapeutic use ($^{211}$At is an exception), a fair number of β emitters, including $^{131}$I, are currently receiving attention as possible candidates for RIT. Among the more promising, are $^{186}$Re ($t_{\frac{1}{2}}=90$ h, $^{67}$Cu ($t_{\frac{1}{2}}=58.5$ h), and $^{90}$Y ($t_{\frac{1}{2}}=65$ h). Of these, $^{90}$Y is currently considered the best,[16,21] with an emission energy of 2.28 MeV, it is calculated to deliver roughly 3 to 4 times more energy (dose) to the tumor per nanomole than either $^{186}$Re or $^{67}$Cu. Unfortunately, at the present time, good immuno-compatible chelands exist for only $^{186}$Re and $^{67}$Cu The former may be attached using the same ligands as were developed for $^{99m}$Tc,[18] and the latter via the rationally-designed activated porphyrins developed by Prof. Lavallee of Hunter College and the Los Alamos INC-11 team.[15] Although these new porphyrin-based systems, in particular, show real promise, being apparently far superior to the existing DTPA or DOTA-type systems,[14] further benefits should be derived from a bifunctional conjugate which is capable of forming stable, nonlabile complexes with $^{90}$Y$^{3+}$ (which cannot be done with porphyrins). The texaphyrin ligand of the present invention not only forms stable complexes with In$^{3+}$ but also binds Y$^{3+}$ effectively. A texaphyrin-type bifunctional conjugate should be developed for use in In-based RID and could also find important application in $^{90}$Y-based RIT. This application outlines ways in which such putative bifunctional conjugates may be prepared. The observation that complexes of both Y$^{3+}$ and In$^{3+}$ may be prepared augurs well for the use of texaphyrin-type systems as conjugates in immunological applications: Both $^{90}$Y and $^{111}$In could conceivably be attached to an antibody of choice using a functionalized texaphyrin. In this regard it is important to note that both the Y$^{3+}$ and In$^{3+}$ complexes of texaphyrin are formed rapidly (insertion and oxidation times are less than 3 hours) from the methylene-linked reduced precursor, and are hydrolytically stable in 1:1 methanol-water mixtures (the half-lives for decomplexation and/or ligand decomposition exceed 3 weeks in both cases.

A further advantage of having developed or developing a wide variety of solubilized texaphyrins, such as those shown in FIGS. 31 and 27, is that many of these would be suitable for further functionalization. For instance, treatment of texaphyrins $7_E$ or $26_D$ with thionyl chloride or p-nitrophenol acetate would generate activated acyl species suitable for attachment to monoclonal antibodies or other biomolecules of interest. Alternatively, standard in situ coupling methods (e.g. 1,1'-carbonyldiimidazole (CDI)[26a]) could be used to effect the same sort of conjugation. In either case, the ability to attach and deliver a potent photosensitizer directly to a tumor locus could have tremendous potential benefit in the treatment of neoplastic disorders. In addition, it is precisely this approach which will allow a variety of useful radioisotopes such as $^{90}$Y and $^{111}$In to be attached to a monoclonal antibody. This could prove to be of immense benefit in the development of this important approach to tumor detection and treatment.

Literature citations in the following list are incorporated by reference herein for the reasons cited.

REFERENCES

1. Pressman, D.; Korngold, L. Cancer 1953, 6, 619.
2. Clinical Nuclear Medicine, Matin, P., Ed., Medical Examination: New York; 1981.
3. Radioimmunoimaging and Radioimmunotherapy, Burchiel, S. W. and Rhodes, B. A., Eds., Elsevier: New York; 1983.
4. Nuclear Imaging in Oncology, Kim, E. E.; Haynie, T. P., Eds., Appleton-Century-Crofts: Norwalk, Connecticut; 1984.
5. Chevru, L. R.; Nunn, A. D.; Loberg, M. D. Semin. Nucl. Med. 1984, 12, 5.
6. Order, S. E. Compr. Therapy 1984, 10, 9.
7. Spencer, R. P. Nuclear Medicine, Medical Examination: New York; 1984.
8. Radiopharmaceuticals and Labelled Compounds 1984 (proceedings of a 1984 conference of the same name), International Atomic Energy Agency: Vienna, 1985.
9. DeLand, F. H.; Goldenberg, D. M. Semin. Nucl. Med. 1985, 15, 2.
10. Radiopharmaceuticals: Progress and Clinical Perspectives, Fritzberg, A. R., Ed., CRC Press: Boca Raton, Fla.; 1986.
11. Goldenberg, D. M.; Goldenberg, H.; Primus, F. J. in Immunoconjugates: Antibody Conjugates in Radioimaging and Therapy of Cancer, Vogel, C.-W., Ed., Oxford University Press: Oxford; 1987, pp. 259–280.
12. Eckelman, W. C.; Paik, C. H.; Reba, R. C. Cancer Res. 1980, 40, 3036.
13. Cole, W. C.; DeNardo, S. J.; Meares, C. F.; McCall, M. J.; DeNardo, G. L.; Epstein, A. L.; O'brien, H. A.; Moi, M. K. J. Nucl. Med. 1987, 28, 83.
14. Deshpande, S. V.; DeNardo, S. J.; Meares, C. F.; McCall, M. J.; Adams, G. P.; Moi, M. K.; DeNardo, G. L. J. Nucl. Med. 1988, 29, 217.
15. Mercer-Smith, J. A.; Roberts, J. C.; Figard, S. D.; Lavallee, D. K. in Antibody-Mediated Delivery Systems, Rodwell, J. D. Ed., Marcel Dekker: New York; 1988, pp. 317–352.
16. (a) O'Brien, H. A., Jr. in reference 119, pp. 161–169. (b) Wessels, B. W.; Rogus, R. D. Med. Phys. 1984, 11, 638. (c) Jungerman, J. A.; Yu, K.-H. P.; Zanelli, C. I. Int. J. Appl. Radiat. Isot. 1984, 9, 883. (d) Humm, J. L. J. Nucl. Med. 1986, 27, 1490.
17. See for instance: (a) Primus, F. J.; DeLand, F. H.; Goldenberg, D. M. in Monoclonal Antibodies and Cancer, "Wright, G. L. Ed., Marcel Dekker: New York; 1984, pp. 305–323. (b) Weinstein, J. N.; Black, C. D. V.; Keenan, A. M.; Holten, O. D., III; Larson, S. M.; Sieber, S. M.; Covell, D. G.; Carrasquillo, J.; Barbet, J.; Parker, R. J. in "Monoclonal Antibodies and Cancer Therapy," Reisfeld, R. A. and Sell, S., Eds., Alan R. Liss: New York; 1985, pp. 473–488.
18. Burns, H. D.; Worley, P.; Wagner, H. N., Jr.; Marzilli, L.; Risch, V. in The Chemistry of Radiopharmaceuticals, Heindel, N. D.; Burns, H. D.; Honda, T.; Brady, L. W., Eds., Masson: New York; 1978.
19. Paik, C. H.; Ebbert, M. A.; Murphy, P. R.; Lassman, C. R.; Reba, R. C.; Eckelman, W. C.; Pak, K. Y.; Powe, J.; Steplewski, Z.; Koprowski, H. J. Nucl. Med. 1983, 24, 1158.
20. See for instance: Hnatowich, D. J.; Childs, R. L.; Lanteigne, D.; Najafi, A. J. Immunol. Meth. 1983, 65, 147.
21. See for instance: Hnatowich, D. J.; Virzi, F.; Doherty, P. W. J. Nucl. Med. 1985, 26, 503.
22. Katagi, T.; Yamamura, T.; Saito, T.; Sasaki, Y. Chem. Lett. 1981, 503.
23. Sessler, J. L.; Johnson, M. R.; Lynch, V. J. Org. Chem. 1987, 52, 4394.
24. Niclas, H. J.; Bohle, M.; Rick, J.-D.; Zeuner, F.; Zolch, L. Z. Chem. 1985, 25, 137.
25. Beilstein 4th ed., 8and 14, p. 785.
26. (a) paul, R.; Anderson, G. W. J. Am. Chem. Soc. 1960, 82, 4596. (b) Davis, M.-T. B.; preston, J. F. Anal. Biochem. 1981, 116, 402. (c) Anderson, G. W.; Zimmerman, J. E; Callahan, F. M. J. Am. Chem. Soc. 1964, 86, 1839.

27. Vollhardt, K. p. C. Synthesis 1985, 765.

28. Kati, H. A.; Siddappa, S. Indian J. Chem. 1983, 22B, 1205.

29. Hove, E.; Horrocks, W. D. J. Am. Chem. Soc. 1978, 100, 4386.

30. Furhop, J.-H.; Smith, K. M. in Porphyrins and Metalloporphyrins, Smith, K. M., Ed., Elsevier: Amsterdam; 1975.

What is claimed is:

1. A method of magnetic resonance image enhancement comprising administering to a subject an effective amount of a texaphyrin-paramagnetic metal complex.

2. The method of claim 1 wherein the paramagnetic metal is $Gd^{+3}$.

3. A method of detection of neoplastic tissue in a patient comprising:
   administering to a patient a texaphyrin-paramagnetic metal complex in an amount effective to enhance a magnetic resonance image; and
   detecting neoplastic tissue by magnetic resonance imaging of said patient.

4. The method of claim 3 wherein the paramagnetic metal is $Gd^{+3}$.

5. A method for MRI enhancement comprising administering a diamagnetic metal ion complexed with texaphyrin or a texaphyrin derivative.

6. The method of claim 5 wherein the diamagnetic metal ion is gadolinium.

* * * * *

UNITED STATES PATENT AND TRADEMARK OFFICE
CERTIFICATE OF CORRECTION

PATENT NO. : 5,256,399
DATED : October 26, 1993
INVENTOR(S) : Jonathan L. Sessler, Gregory W. Hemmi and Toshiaki Murai It is certified that error appears in the above-identified patent and that said Letters Patent is hereby corrected as shown below:

Claim 5, col. 72, line 13, delete the word "diamagnetic" and substitute the word --paramagnetic--, therefore.

Claim 6, col. 72, line 15, delete the word "diamagnetic" and substitute the word --paramagnetic--, therefore.

Signed and Sealed this

Twenty-ninth Day of March, 1994

Attest:

BRUCE LEHMAN

Attesting Officer     Commissioner of Patents and Trademarks